(12) United States Patent
Endo

(10) Patent No.: US 7,812,157 B2
(45) Date of Patent: Oct. 12, 2010

(54) THIOL COMPOUND DERIVATIVE, CURABLE COMPOSITION CONTAINING THE DERIVATIVE, AND MOLDED PRODUCT THEREOF

(75) Inventor: Kiyoshi Endo, Kitaibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 772 days.

(21) Appl. No.: 11/711,692

(22) Filed: Feb. 28, 2007

(65) Prior Publication Data

US 2008/0227977 A1 Sep. 18, 2008

Related U.S. Application Data

(62) Division of application No. 10/479,627, filed as application No. PCT/JP02/05483 on Jun. 4, 2002, now Pat. No. 7,199,169.

(30) Foreign Application Priority Data

Jun. 4, 2001 (JP) ............................. 2001-168672
Jun. 4, 2001 (JP) ............................. 2001-168673

(51) Int. Cl.
*C07D 251/38* (2006.01)
*C08K 5/378* (2006.01)
*C08L 101/04* (2006.01)
*C08J 5/00* (2006.01)

(52) U.S. Cl. ...................... 544/219; 524/100
(58) Field of Classification Search ................. 544/219; 524/100
See application file for complete search history.

(56) References Cited

U.S. PATENT DOCUMENTS

| 4,096,206 A | 6/1978 | Boyer |
| 4,569,958 A | 2/1986 | Maeda et al. ............... 524/100 |
| 5,206,304 A | 4/1993 | Hellwig et al. |

| 7,199,169 B2 * | 4/2007 | Endo et al. .................. 524/100 |
| 7,384,995 B2 * | 6/2008 | Endo et al. .................. 524/100 |

FOREIGN PATENT DOCUMENTS

EP 0 347 524 12/1989

OTHER PUBLICATIONS

Abstract of JP 1236252, Sankyo Yuki Gosei Kabushiki Kaisha, Sep. 21, 1989.
Abstract of JP2002293815, Tamura Kaken Co Ltd., Oct. 9, 2002.

* cited by examiner

*Primary Examiner*—Venkataraman Balasubramanian
(74) *Attorney, Agent, or Firm*—Jacobson Holman PLLC

(57) ABSTRACT

The present invention relates to a thiol compound derivative represented by the following formula (1), a curable composition containing the derivative, and a molded product made of the composition. More particularly, the invention relates to a thiol compound derivative which is added to a polymer having reactivity to a thiol derivative substituent to provide a curable composition, a curable composition containing the derivative and a crosslinkable halogen-containing crosslinking polymer, and a crosslinked molded product of the composition.

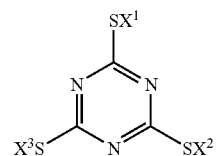

(1)

wherein $X^1$, $X^2$ and $X^3$ are each a group represented by the following formula (2).

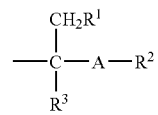

(2)

5 Claims, 18 Drawing Sheets

THIOL COMPOUND DERIVATIVE, CURABLE COMPOSITION CONTAINING THE DERIVATIVE, AND MOLDED PRODUCT THEREOF

This is a divisional of application Ser. No. 10/479,627 filed Dec. 4, 2003, now U.S. Pat. No. 7,199,169 which in turn is a nationalization of PCT/JP02/05483 filed Jun. 4, 2002 and published in Japanese.

TECHNICAL FIELD

The present invention relates to a thiol compound derivative, a curable composition containing the derivative, and a molded product made of the composition. More particularly, the invention relates to a thiol compound derivative which is added to a polymer having reactivity to a thiol derivative substituent to provide a curable composition, a curable composition containing the derivative and a crosslinkable halogen-containing crosslinking polymer, and a crosslinked molded product of the composition.

BACKGROUND ART

Epichlorohydrin rubber, chlorine-containing acrylic rubber, etc. have been heretofore widely used for molded articles, such as hoses and sealing parts, because they are excellent in various properties, such as oil resistance, heat resistance, weathering resistance, ozone resistance and compression set.

In general, halogen-containing crosslinking polymers, such as the epichlorohydrin rubber and the chlorine-containing acrylic rubber, are often stored in the form of compositions obtained by adding crosslinking additives, such as crosslinking agent and crosslinking accelerator, to the polymers.

When diene type rubber compositions or chlorine type rubber compositions containing vulcanizing additives, such as vulcanizing agent and vulcanization accelerator, are stored, vulcanization generally proceeds slowly, and as a result, changes, e.g., increase of viscosity, reduction of scorch time and decrease of vulcanizing rate, are brought about to thereby lower processability of the compositions into molded articles or properties of the vulcanization products. From the viewpoint of retention of storage stability, these changes are desired to be small. If the vulcanization additives are not added, these changes are small. From the viewpoint of productivity, however, curable compositions in which the vulcanization additives are added in advance are generally employed, and therefore, it becomes important to improve storage stability of the compositions containing the vulcanization additives.

As the vulcanization additives for the diene type rubbers or the chlorine type rubbers, polythiol compounds, such as dithiol compounds and trithiol compounds, are conventionally known.

These polythiol compounds, however, have high reactivity, so that when the rubbers and the vulcanization additives are kneaded and processed, premature vulcanization sometimes takes place, or even if kneading can be carried out smoothly without premature vulcanization, gelation sometimes takes place during the subsequent storing stage. Thus, the compositions have a problem of lack of storage stability even if the properties of the resulting cured products are excellent.

As the crosslinking additives for the halogen-containing crosslinking polymers, triazinethiols are known.

The triazinethiols, however, have high reactivity and high crosslinking rate, so that when the rubbers and the crosslinking additives are kneaded and processed, premature crosslinking sometimes takes place, or even if kneading can be carried out smoothly without premature crosslinking, gelation sometimes takes place to increase viscosity in the subsequent storing stage, or partial crosslinking is promoted. That is to say, scorching is liable to occur, and hence, molding troubles are sometimes brought about.

On this account, an attempt to use a premature vulcanization inhibitor in combination to improve storage stability has been made. By the use of the premature vulcanization inhibitor in combination, however, problems of decrease of vulcanizing rate and deterioration of heat resistance are brought about.

For controlling the crosslinking rate, there has been also made an attempt to add metal oxide, metal hydroxide, carbonate, organic acid salt or the like and to select the type of metal, type of counter ion, etc. according to the reactivity of the halogen-containing crosslinking polymers and the reactivity of the triazinethiols. However, if satisfactory crosslinking rate is intended to be obtained, the scorch time is sometimes shortened.

Accordingly, there has been desired development of a novel thiol compound derivative capable of providing a rubber composition or a resin composition having excellent storage stability, processability and curability without using a premature vulcanization inhibitor that exerts evil influences on the properties of a cured product of a diene type rubber composition, a chlorine type rubber (halogen-containing crosslinking polymer) composition or the like. There has been also desired development of a curable composition having storage stability and moderate crosslinking rate and capable of providing a crosslinked product having excellent physical properties with a good balance.

The present inventors have earnestly studied to solve such problems as mentioned above, and as a result, they have found that by the use of, as a crosslinking agent, a thiol compound derivative wherein a thiol compound is protected by a protective group of vinyl ether or the like, a curable composition having excellent storage stability and crosslinking rate and capable of providing a crosslinked product of excellent physical properties can be obtained without using a premature vulcanization inhibitor that exerts evil influences on the properties of a cured product of a halogen-containing crosslinking polymer composition or a diene type rubber composition. Based on the finding, the present invention has been accomplished.

It is an object of the present invention to provide a novel thiol compound derivative capable of providing a rubber composition or a resin composition having excellent storage stability, processability and curability. It is another object of the invention to provide a curable composition comprising a halogen-containing crosslinking polymer and having a good balance of storage stability, crosslinking rate and physical properties of its crosslinked product. It is a further object of the invention to provide a molded product of the curable composition.

DISCLOSURE OF THE INVENTION

The thiol compound derivative of the present invention is a thiol compound derivative represented by the following formula (1):

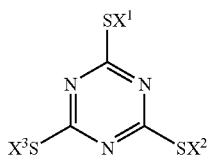
(1)

wherein $X^1$, $X^2$ and $X^3$ may be the same or different and are each a group represented by the following formula (2):

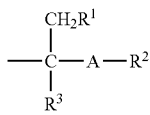
(2)

wherein A is an oxygen atom or a sulfur atom,
$R^1$ is a hydrogen atom, an alkyl group or a phenyl group,
$R^2$ is a group selected from the group consisting of the following groups (a) to (f),
$R^3$ is a hydrogen atom, an alkyl group or a phenyl group, and
$R^1$ and $R^2$ may form a ring;

(a) a group selected from an alkyl group, a halogenated alkyl group, an alkyl group having at least one hydroxyl group, an alkenyl group, an alkynyl group and an aralkyl group, (b) a residue wherein a hydroxyl group is removed from a hydroxyl group-containing compound selected from alkylene glycol, dialkylene glycol, trialkylene glycol, tetraalkylene glycol, allyl alcohols, ketooximes, alkanolamines, dialkanolamines, trialkanolamines, trialkylsilanol, alicyclic alcohol and naphthyl alcohols, (c) a group represented by the following formula (3):

—CHY—CH$_2$X (3)

wherein X is any one of a halogen atom, an alkoxy group, an alkoxyalkoxy group, a dialkylamino group, a trialkylsilyl group, an acetoxy group and a piperidino group, and Y is a hydrogen atom or a halogen atom, (d) a group represented by the following formula (4):

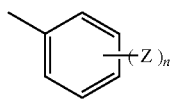
(4)

wherein Z is any one of a hydrogen atom, a halogen atom, a nitro group, an amino group, an alkoxy group, an alkylamino group, a dialkylamino group, an alkyl group and an acyl group, and n is an integer of 1 to 3 and is a number of substituents Z bonded to the phenyl group skeleton in the formula (4), (e) a group represented by —CH$_2$—C$_6$H$_5$ or —CHCH$_3$—C$_6$H$_5$, and (f) a group represented by the following formula (5) or (6):

—R$^4$-ACH═CH$_2$ (5)

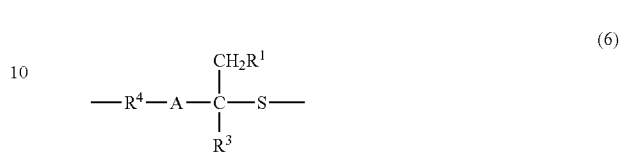
(6)

wherein $R^1$ and $R^3$ are the same as $R^1$ and $R^3$ in the formula (2), A is an oxygen atom or a sulfur atom, and $R^4$ is any one of —CH$_2$—, —CH$_2$CH$_2$—, —CH$_2$CH$_2$CH$_2$—, —CH$_2$CH$_2$CH$_2$CH$_2$—, CH$_2$CH$_2$OCH$_2$CH$_2$—, —CH$_2$CH$_2$OCH$_2$CH$_2$OCH$_2$CH$_2$—,

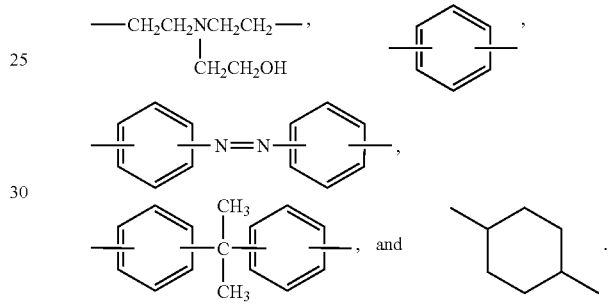

In the above thiol compound derivative, it is preferable that in the formula (2), A is an oxygen atom, $R^1$ is a hydrogen atom, $R^2$ is an alkyl group or a residue wherein a hydroxyl group is removed from (poly)alkylene glycol, and $R^3$ is a hydrogen atom.

The formula (2) is preferably represented by the following formula (7):

(7)

wherein n is 3 or 4.

The thiol compound derivative of the present invention is a thiol compound derivative represented by the following formula (8):

(8)

wherein $X^1$ and $X^2$ may be the same or different and are each a group represented by the following formula (2):

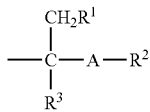
(2)

said formula (2) being the same as that previously described.

The thiol compound derivative of the present invention is a thiol compound derivative represented by the following formula (9):

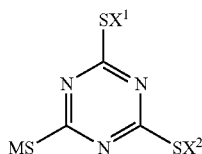
(9)

wherein $X^1$ and $X^2$ may be the same or different and are each a group represented by the following formula (2), and M is an alkali metal or an alkaline earth metal;

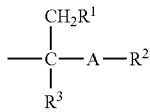
(2)

said formula (2) being the same as that previously described.

The thiol compound derivative of the present invention is a thiol compound derivative represented by the following formula (10):

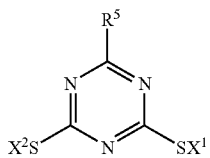
(10)

wherein $X^1$ and $X^2$ may be the same or different and are each a group represented by the following formula (2), and $R^5$ is a group selected from the following groups (g) to (k);

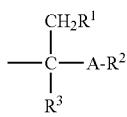
(2)

said formula (2) being the same as that previously described;

(g) a group selected from a hydrogen atom, an alkyl group, an alkenyl group, an alkynyl group, a phenyl group, an aralkyl group and $-NH_2$, (h) a dialkylamino group represented by the following formula (11):

(11)

wherein $R^6$ and $R^7$ are each a group selected from an alkyl group, an alkenyl group, an alkynyl group, an aralkyl group, a benzyl group, an allyl group, a cycloalkyl group, a fluoroalkyl group and a phenyl group, and $R^6$ and $R^7$ may be the same or different, (i) a monoalkylamino group represented by the following formula (12):

(12)

wherein $R^8$ is a group selected from an alkyl group, an alkenyl group, an alkynyl group, an aralkyl group, a benzyl group, an allyl group, a cycloalkyl group, a fluoroalkyl group, an anilino group, a hydroxyanilino group and a phenyl group, (j) a group represented by the following formula (13):

(13)

wherein $R^9$ is a group selected from an alkyl group, an alkenyl group, an aralkyl group, a halogenophenyl group, a naphthyl group, a cycloalkyl group and a phenyl group, and (k) a group represented by the following formula (14):

(14)

wherein $R^{10}$ is a group selected from an alkyl group, an alkenyl group, an alkynyl group, a phenyl group, an aralkyl group, a halogenophenyl group, a naphthyl group and a cycloalkyl group.

In the above thiol compound derivative, it is preferable that in the formula (2), A is an oxygen atom, $R^1$ is a hydrogen atom, $R^2$ is an alkyl group or a residue wherein a hydroxyl group is removed from (poly)alkylene glycol, and $R^3$ is a hydrogen atom.

In the above thiol compound derivative, it is also preferable that the formula (2) is represented by the following formula (7):

(7)

wherein n is 3 or 4.

The thiol compound derivative of the present invention is a thiol compound derivative represented by the following formula (15):

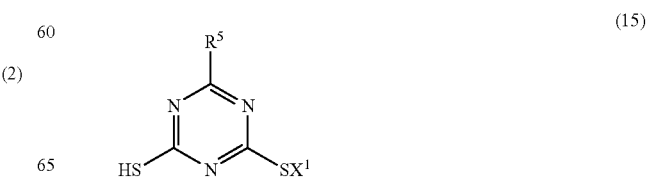
(15)

wherein $X^1$ is a group represented by the following formula (2), and $R^5$ is the same as $R^5$ in the formula (10);

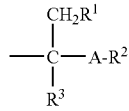
(2)

said formula (2) being the same as that previously described.

The thiol compound derivative of the present invention is a thiol compound derivative represented by the following formula (16):

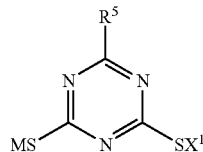
(16)

wherein $X^1$ is a group represented by the following formula (2), M is an alkali metal or an alkaline earth metal, and $R^5$ is the same as $R^5$ in the formula (10);

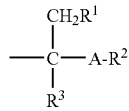
(2)

said formula (2) being the same as that previously described.

The curable composition of the present invention contains any one of the above-mentioned thiol compound derivatives of the present invention.

The curable composition of the present invention contains:

a halogen-containing crosslinking polymer, and a thiol compound derivative having, in one molecule, at least one functional group represented by the following formula (17):

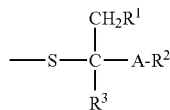
(17)

wherein A, $R^1$, $R^2$ and $R^3$ are the same as A, $R^1$, $R^2$ and $R^3$ in the formula (2).

The functional group represented by the formula (17) is preferably formed by reacting a compound having a thiol group (—SH) with a vinyl ether.

In the above curable composition, the thiol compound derivative is preferably a compound represented by the following formula (1):

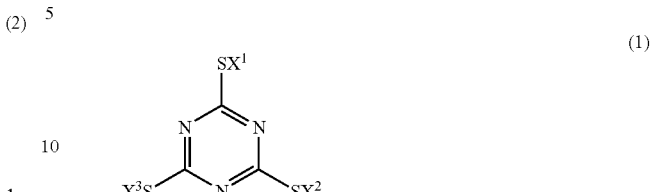
(1)

wherein $X^1$, $X^2$ and $X^3$ are each a group represented by the following formula (2):

(2)

said formulas (1) and (2) being the same as those previously described.

In the above curable composition, the thiol compound derivative is also preferably a compound represented by the following formula (8):

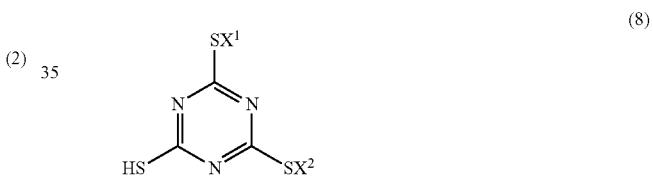
(8)

wherein $X^1$ and $X^2$ may be the same or different and are each a group represented by the following formula (2):

(2)

said formula (2) being the same as that previously described.

In the above curable composition, the thiol compound derivative is also preferably a compound represented by the following formula (9):

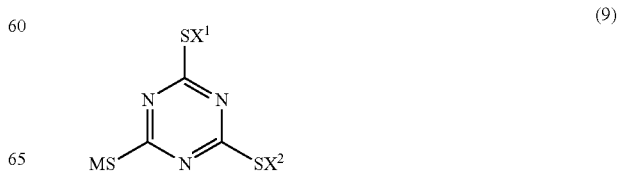
(9)

wherein $X^1$ and $X^2$ are each a group represented by the following formula (2):

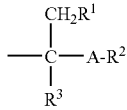

(2)

said formulas (9) and (2) being the same as those previously described.

In the above curable composition, the thiol compound derivative is also preferably a compound represented by the following formula (10):

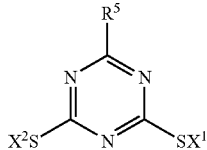

(10)

wherein $X^1$ and $X^2$ are each a group represented by the following formula (2):

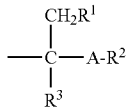

(2)

said formulas (10) and (2) being the same as those previously described.

In the above curable composition, the thiol compound derivative is also preferably a compound represented by the following formula (15):

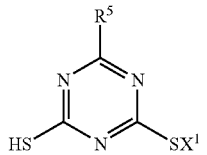

(15)

wherein $X^1$ is a group represented by the following formula (2):

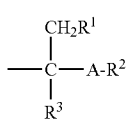

(2)

said formulas (15) and (2) being the same as those previously described.

In the above curable composition, the thiol compound derivative is also preferably a compound represented by the following formula (16):

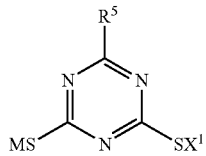

(16)

wherein $X^1$ is a group represented by the following formula (2):

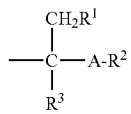

(2)

said formulas (16) and (2) being the same as those previously described.

In the curable compositions of the invention, it is preferable that in the formulas (2) and (17), A is an oxygen atom, $R^1$ is a hydrogen atom, $R^2$ is an alkyl group or a residue wherein a hydroxyl group is removed from (poly)alkylene glycol, and $R^3$ is a hydrogen atom.

The formulas (2) and (17) are each preferably represented by the following formula (7):

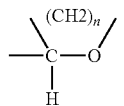

(7)

wherein n is 3 or 4.

The curable composition of the present invention contains a compound obtained by contacting triazinethiol with a polyvalent vinyl ether, and a halogen-containing crosslinking polymer.

The triazinethiol is preferably represented by the following formula (18):

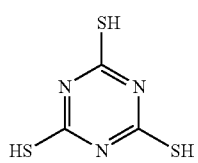

(18)

The triazinethiol is also preferably represented by the following formula (19):

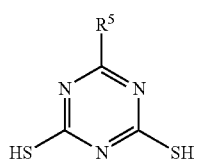

(19)

wherein $R^5$ is the same as $R^5$ in the formula (10).

The polyvalent vinyl ether is preferably at least one ether selected from divinyl ethers, trivinyl ethers and tetravinyl ethers.

In the curable compositions of the present invention, the halogen-containing crosslinking polymer is preferably an acrylic rubber, an epichlorohydrin rubber, a chloroprene rubber or chlorosulfonated polyethylene.

The curable compositions of the present invention preferably contain an organic acid metal salt, and the organic acid metal salt is preferably an organic acid alkali metal salt and/or an organic acid alkaline earth metal salt. The curable compositions of the present invention preferably further contain, in addition to the organic acid metal salt, a vulcanization supplement accelerator, and the vulcanization supplement accelerator is preferably an onium salt and/or polyalkylene oxide.

The curable compositions of the present invention preferably contain an amine type anti-aging agent, and a sulfur compound or a phosphorus compound.

The molded product of the present invention is obtained by crosslinking the curable composition of the present invention.

Figure 6:
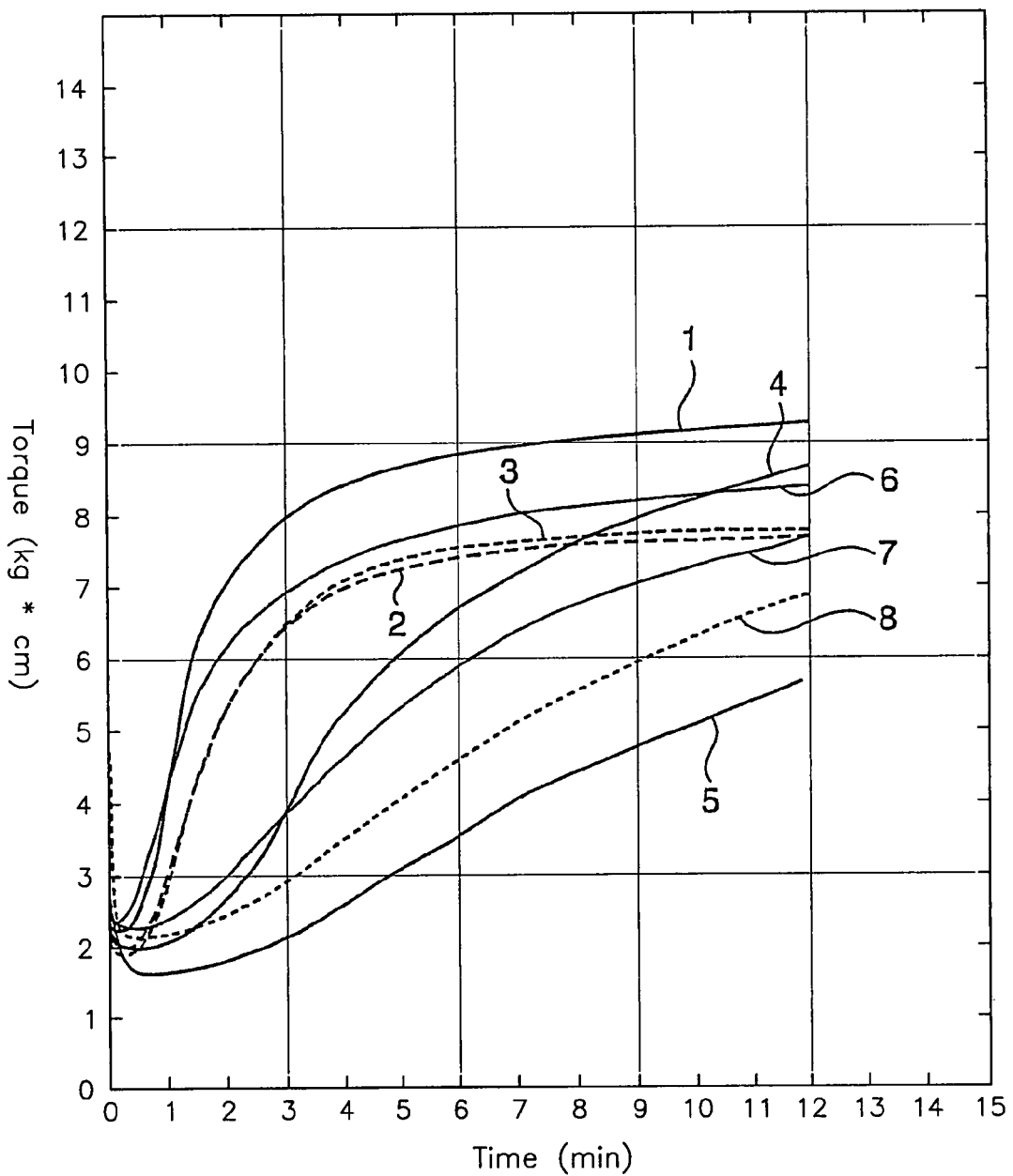
FIG. 6 shows curelastometer curves of Examples 3 to 7 and Comparative Examples 2, 4 and 5.

Numeral 1 in FIG. 6 designates a curelastometer curve of Example 3.

Numeral 2 in FIG. 6 designates a curelastometer curve of Example 4.

Numeral 3 in FIG. 6 designates a curelastometer curve of Example 5.

Numeral 4 in FIG. 6 designates a curelastometer curve of Example 6.

Numeral 5 in FIG. 6 designates a curelastometer curve of Example 7.

Numeral 6 in FIG. 6 designates a curelastometer curve of Comparative Example 2.

Numeral 7 in FIG. 6 designates a curelastometer curve of Comparative Example 4.

Numeral 8 in FIG. 6 designates a curelastometer curve of Comparative Example 5.

Figure 7:
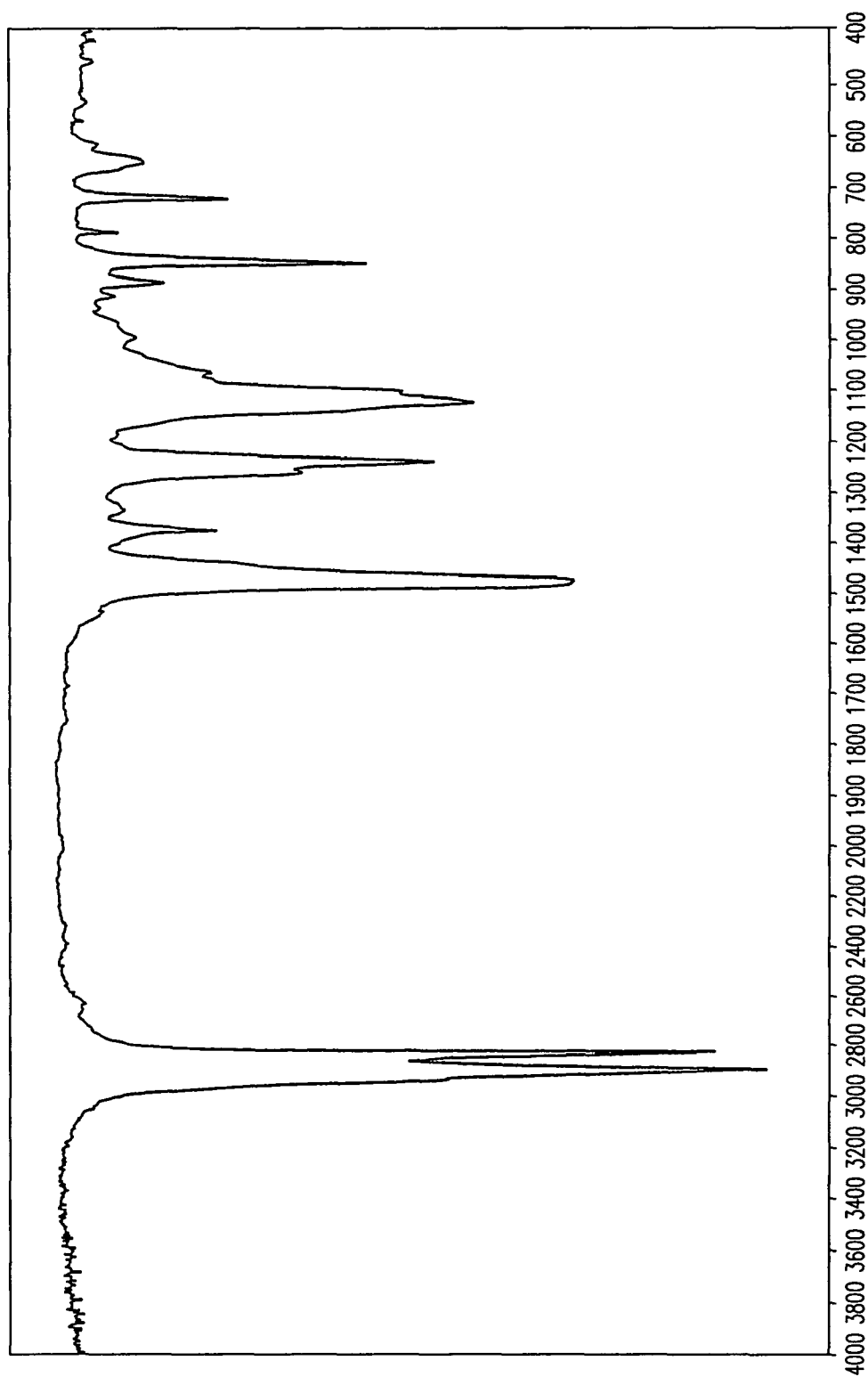

FIG. 7 is a chart of an IR absorption spectrum of a synthetic substance obtained in Example 34.

Figure 8:
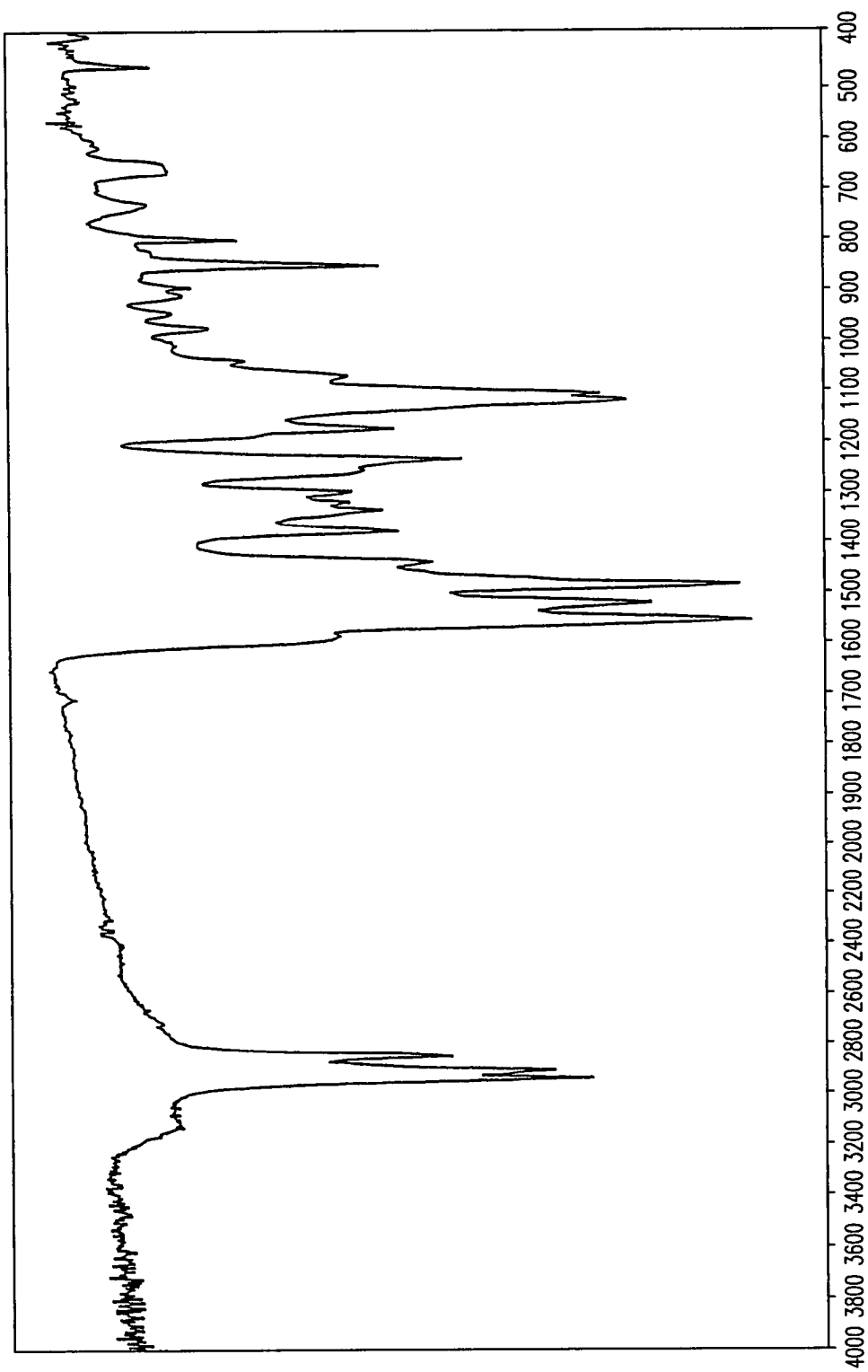

FIG. 8 is a chart of an IR absorption spectrum of a synthetic substance obtained in Example 35.

Figure 9:
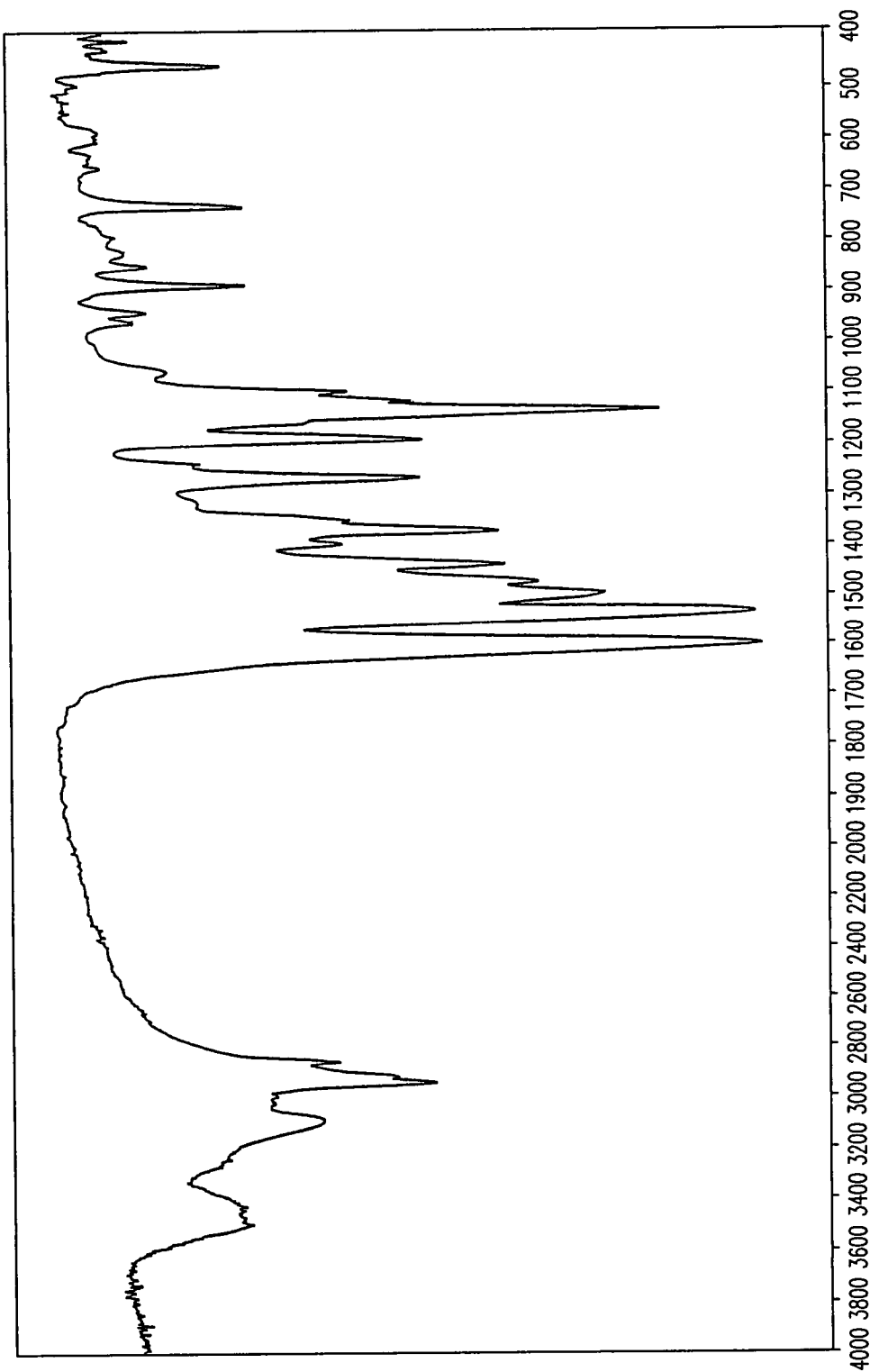

FIG. 9 is a chart of an IR absorption spectrum of 6-dibutylamino-S-triazine-2,4-dithiol that is a starting material for synthesis.

Figure 10:
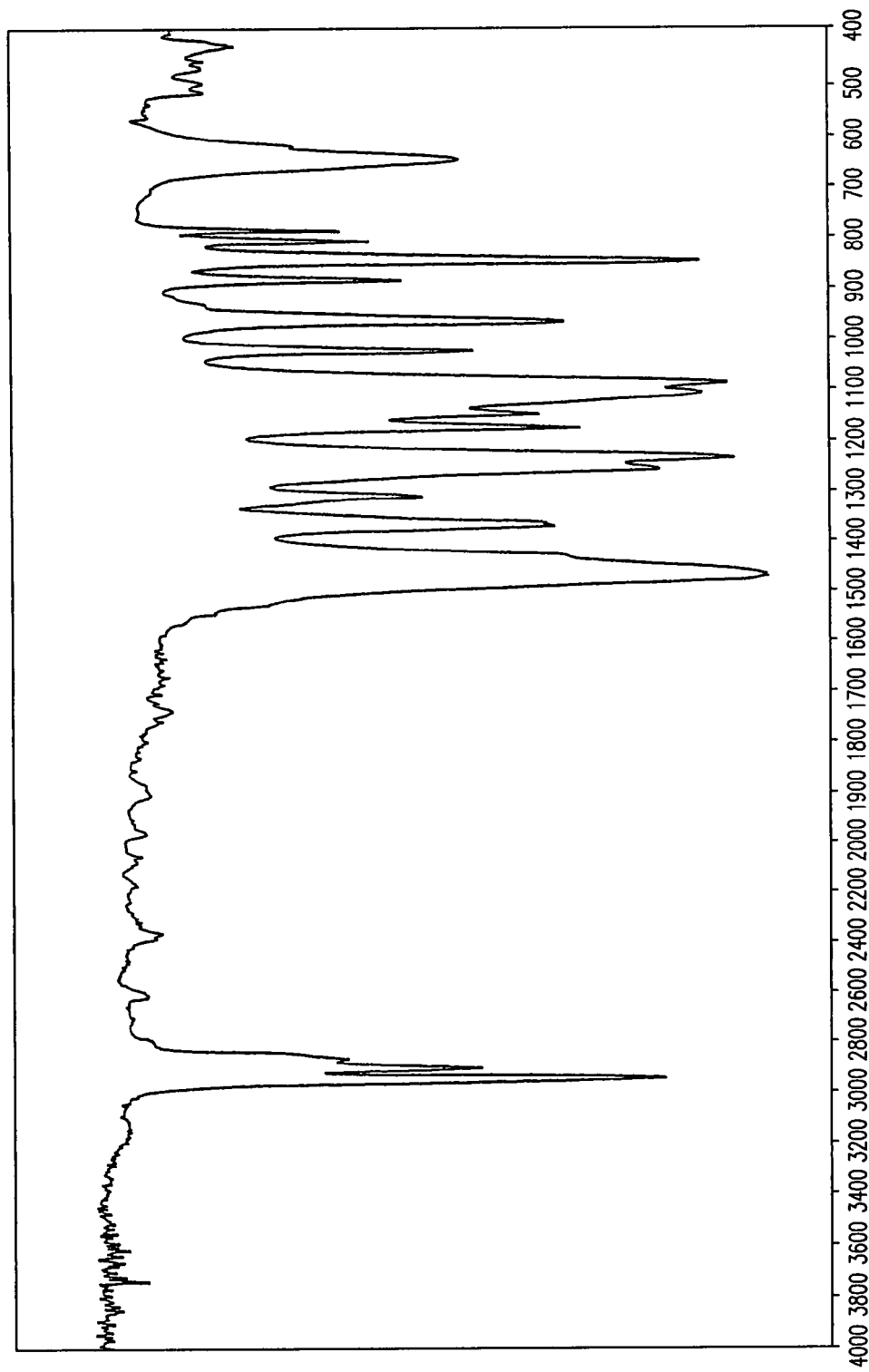

FIG. 10 is a chart of an IR absorption spectrum of a synthetic substance obtained in Example 36.

Figure 11:
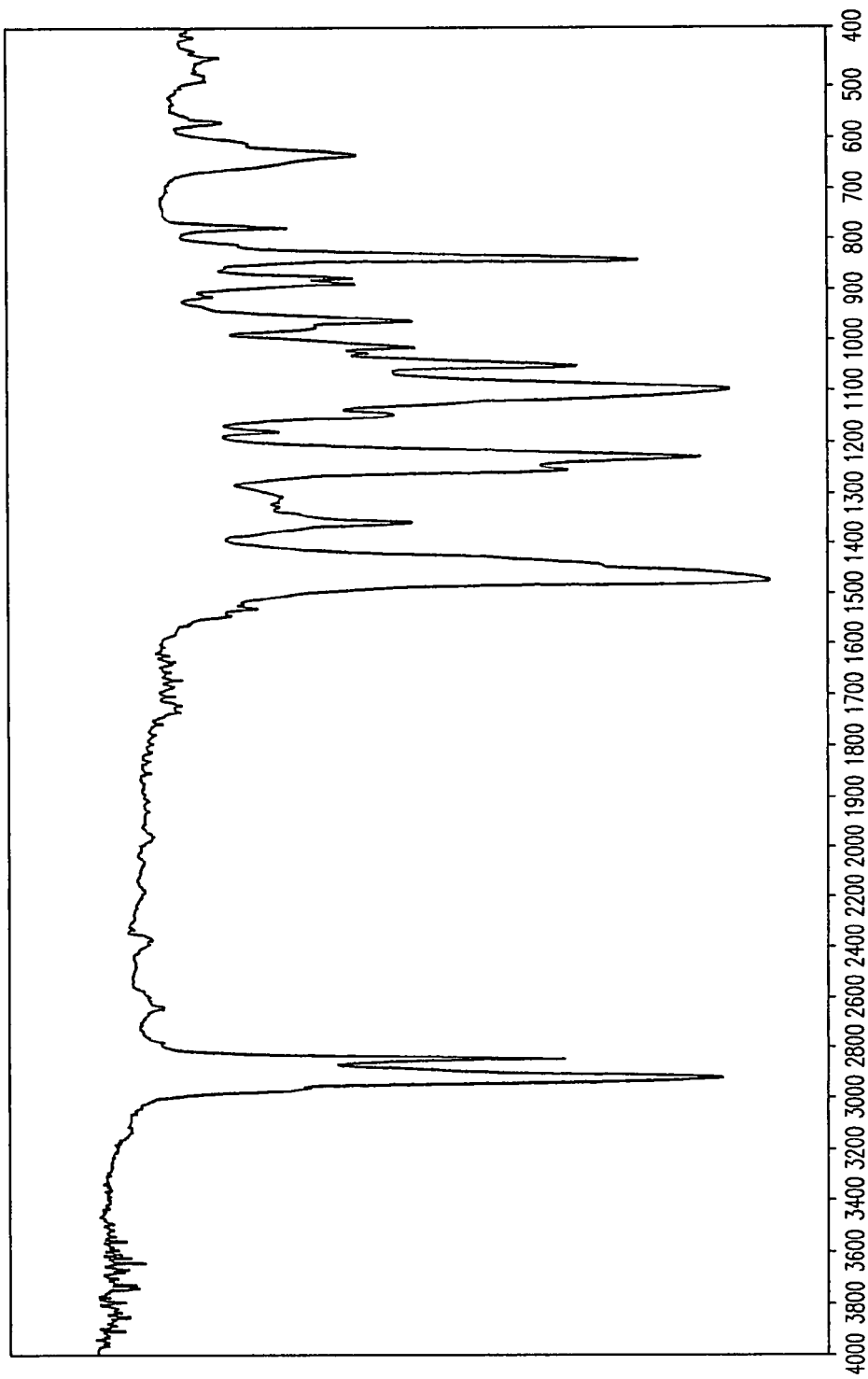

FIG. 11 is a chart of an IR absorption spectrum of a synthetic substance obtained in Example 37.

Figure 12:
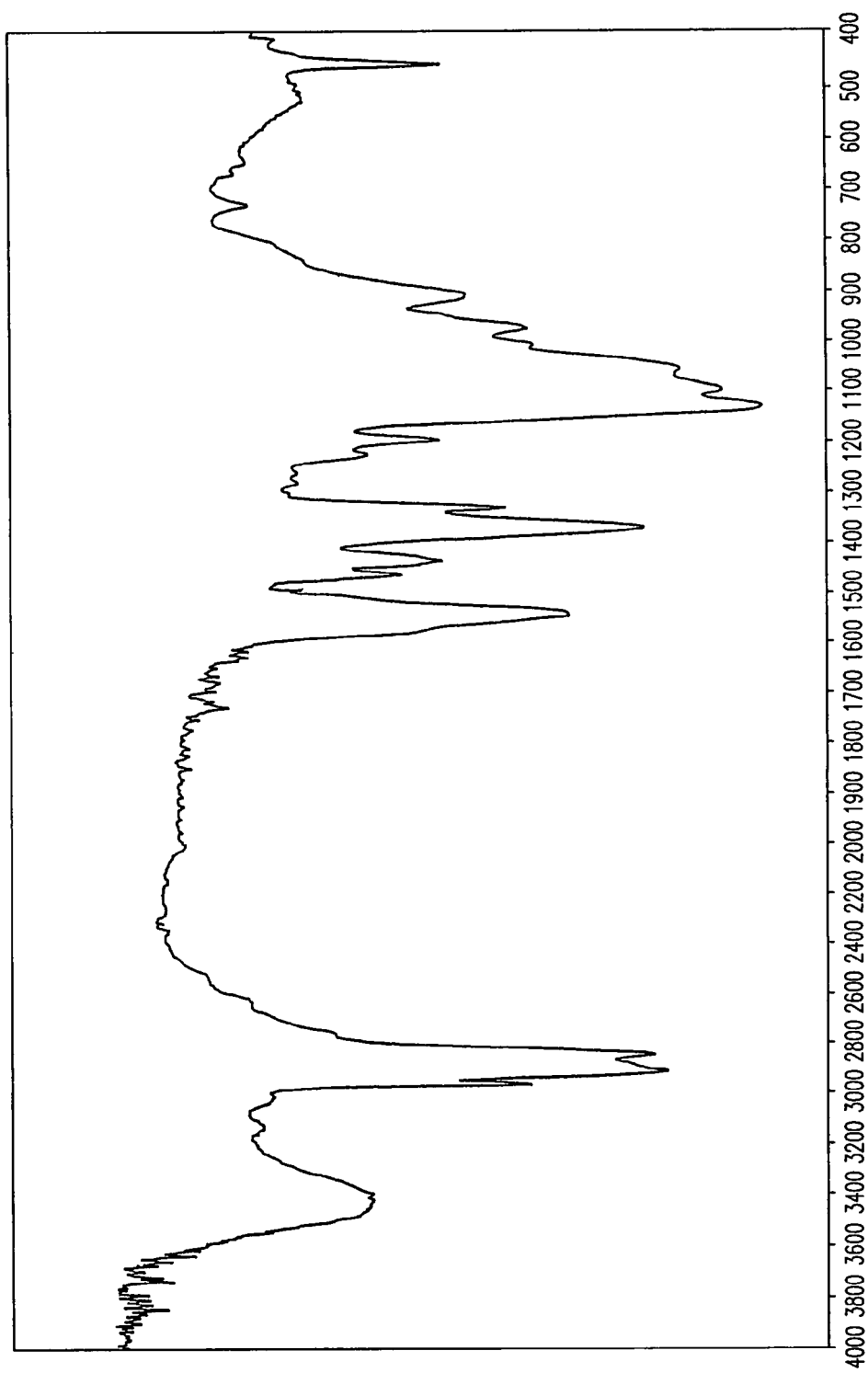

FIG. 12 is a chart of an IR absorption spectrum of a synthetic substance obtained in Example 38.

Figure 13:
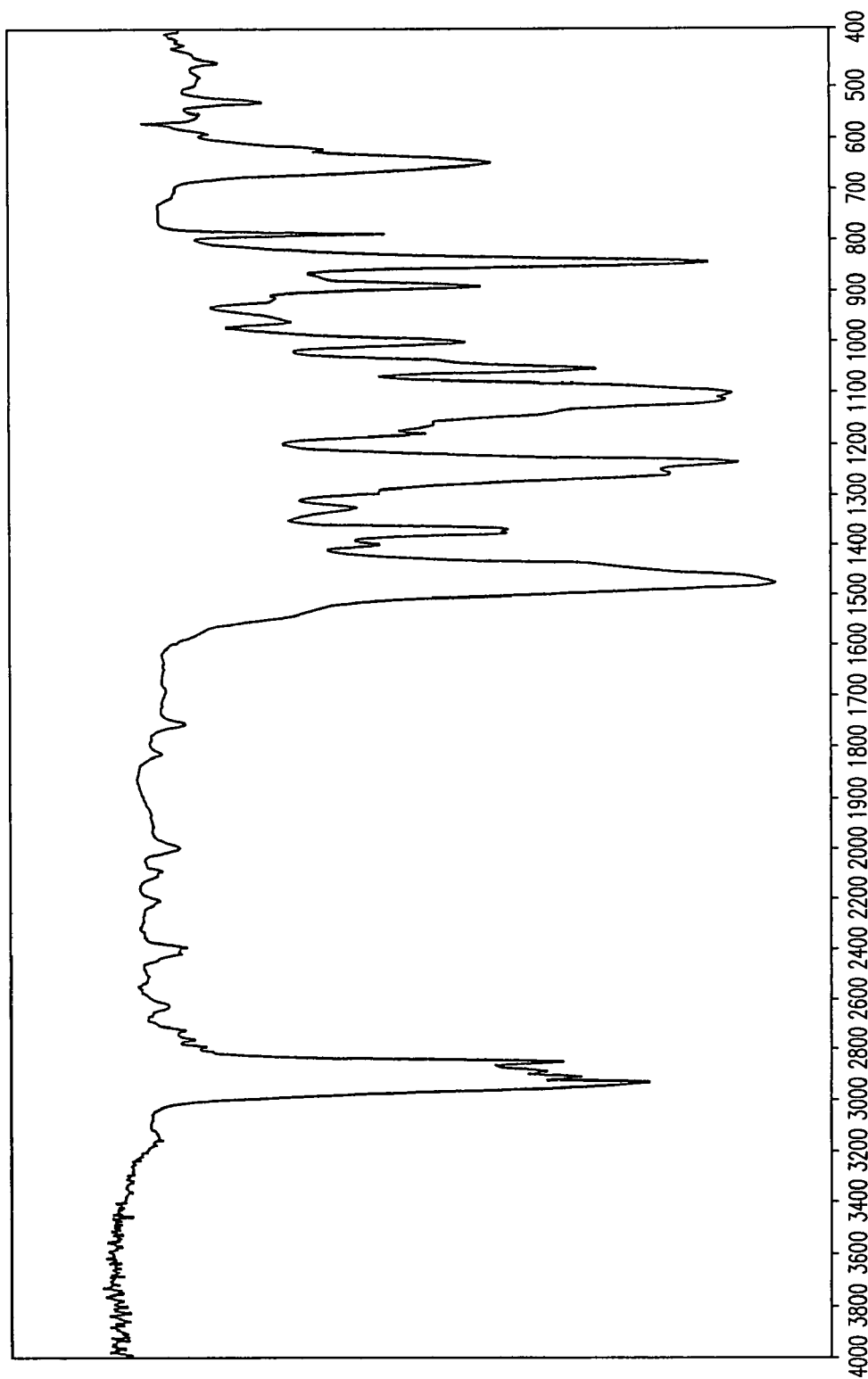

FIG. 13 is a chart of an IR absorption spectrum of a synthetic substance obtained in Example 39.

Figure 14:
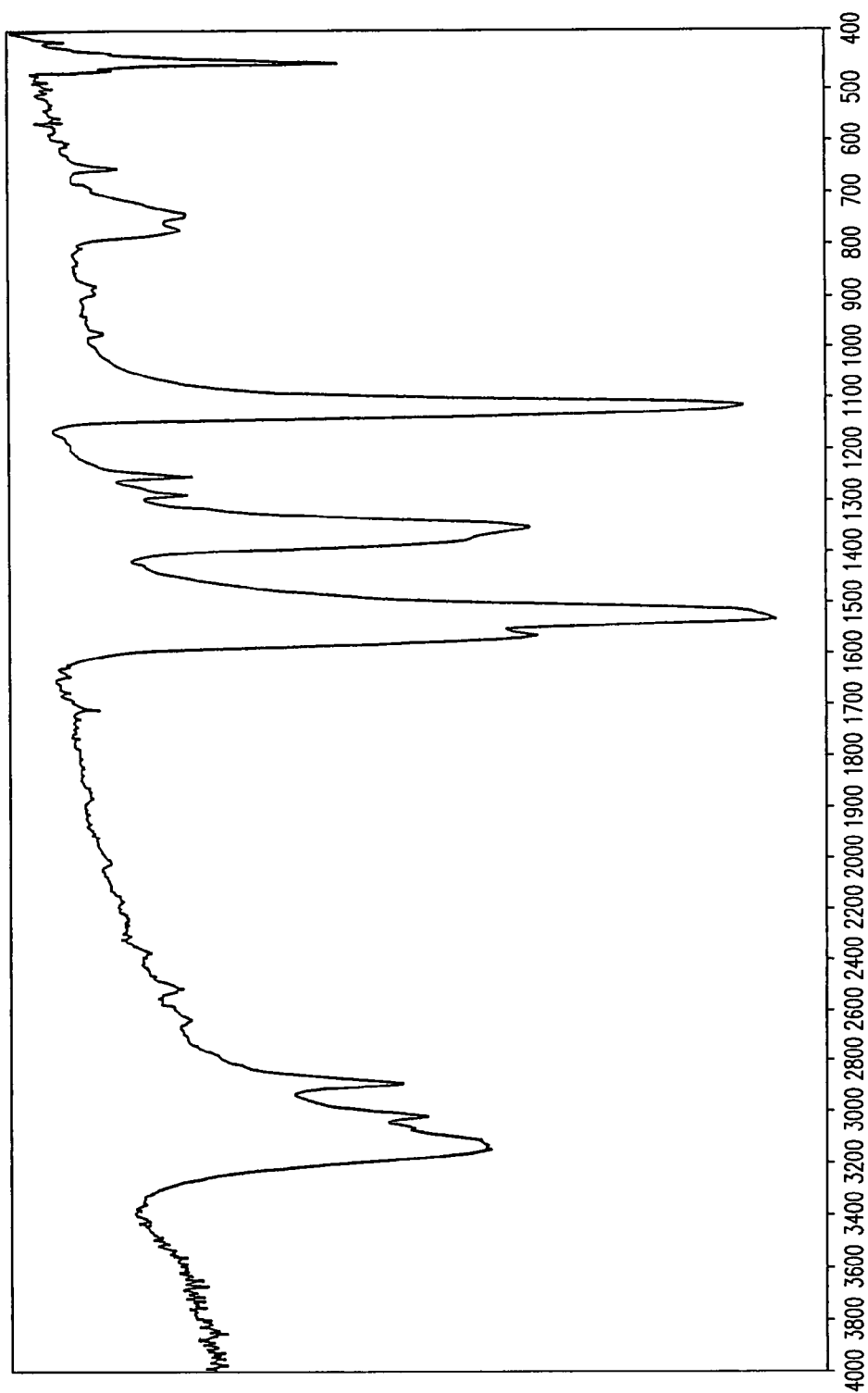

FIG. 14 is a chart of an IR absorption spectrum of a sample obtained by storing the synthetic substance obtained in Example 39, in the atmosphere.

Figure 15:
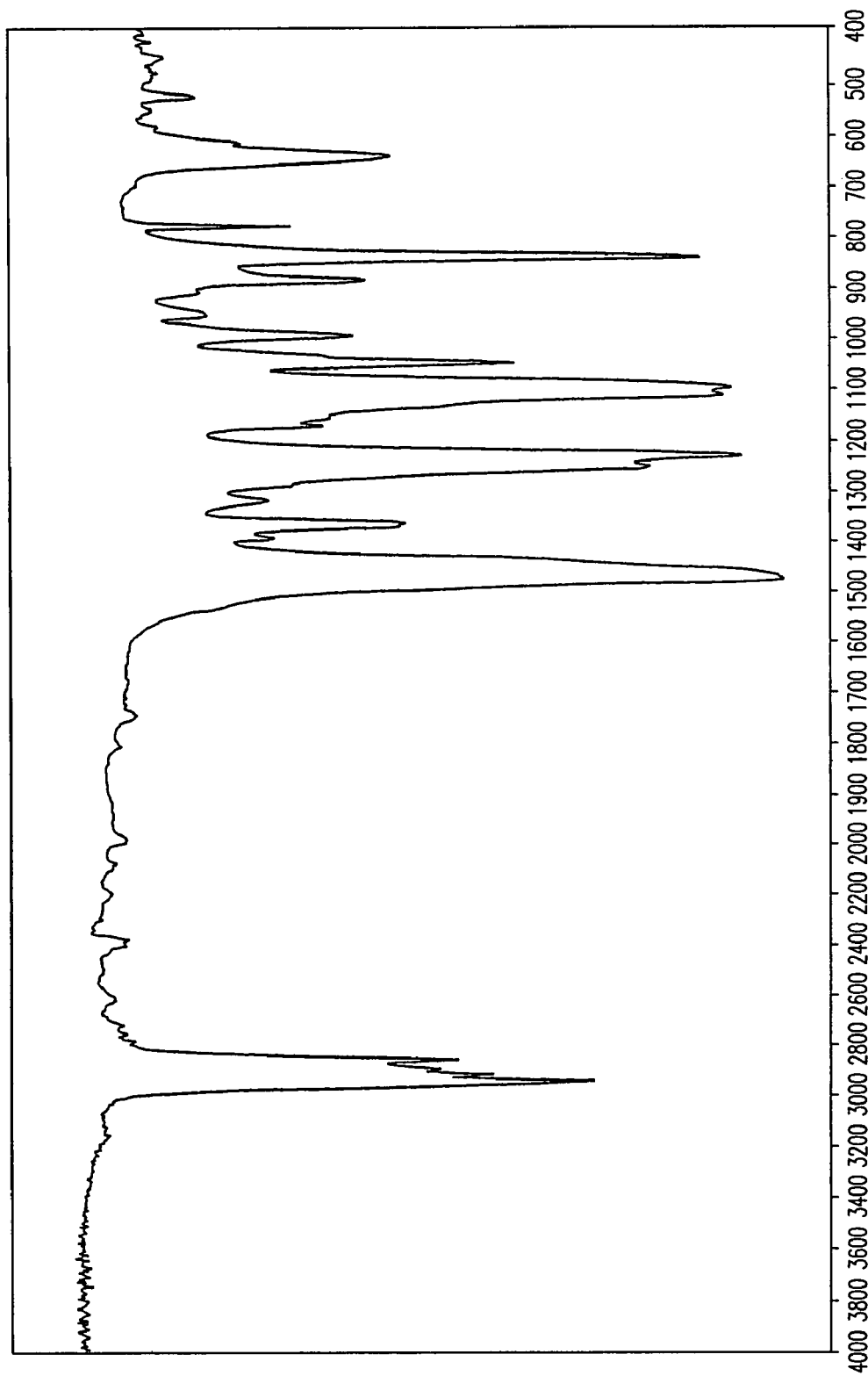

FIG. 15 is a chart of an IR absorption spectrum of a synthetic substance obtained in Example 40.

Figure 16:
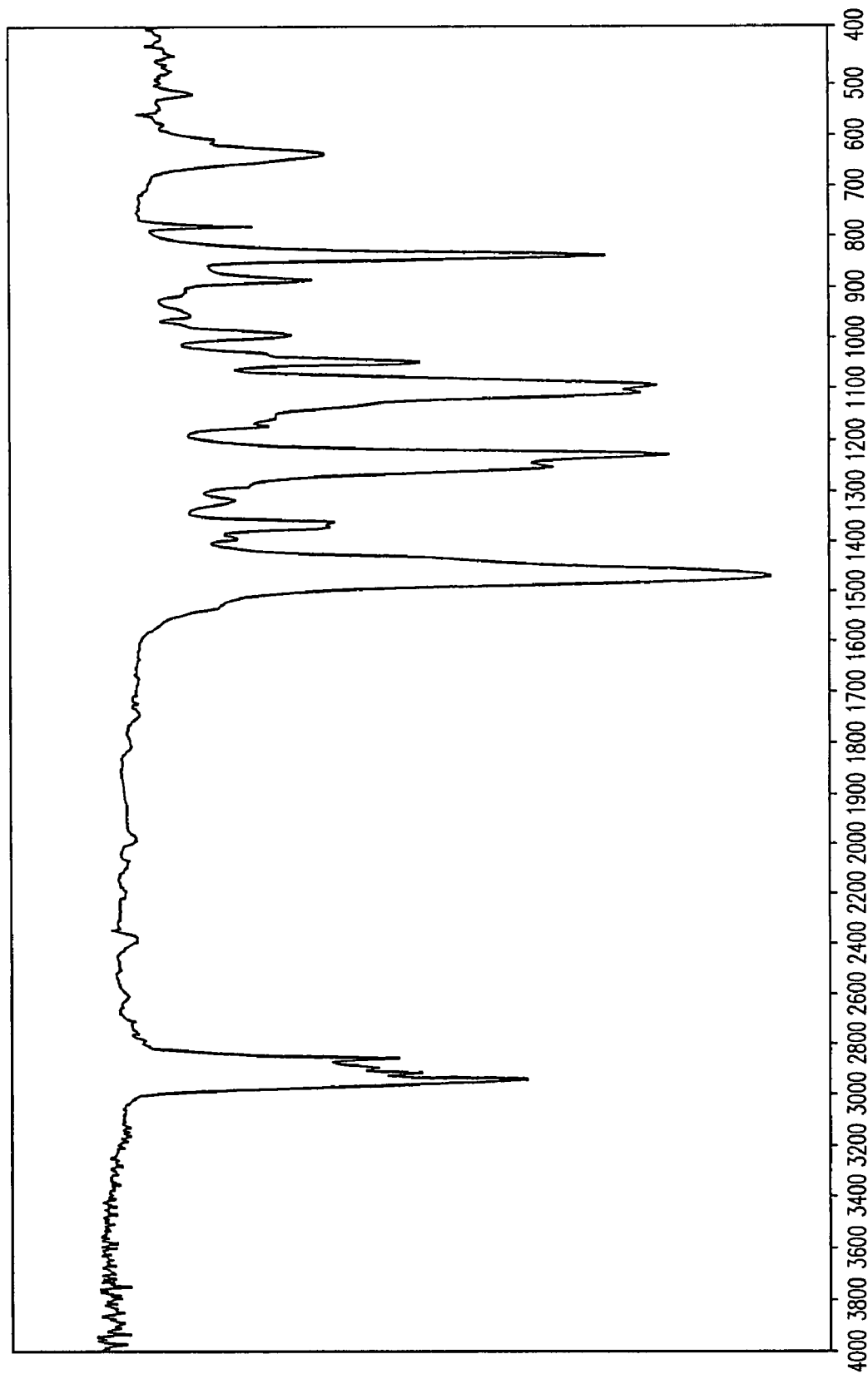

FIG. 16 is a chart of an IR absorption spectrum of a sample obtained by storing the synthetic substance obtained in Example 40, in the atmosphere.

Figure 17:
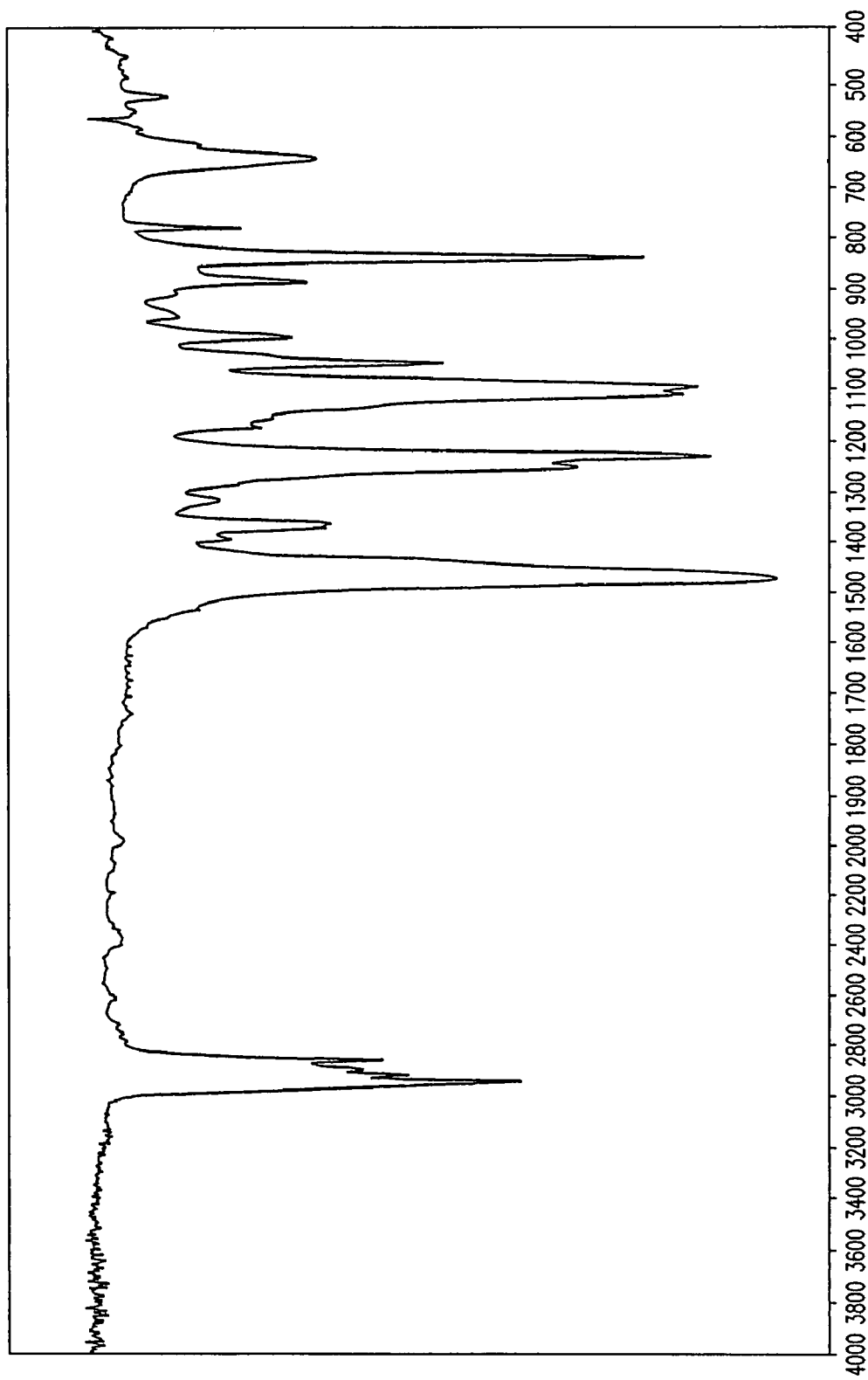

FIG. 17 is a chart of an IR absorption spectrum of a synthetic substance obtained in Example 41.

Figure 18:
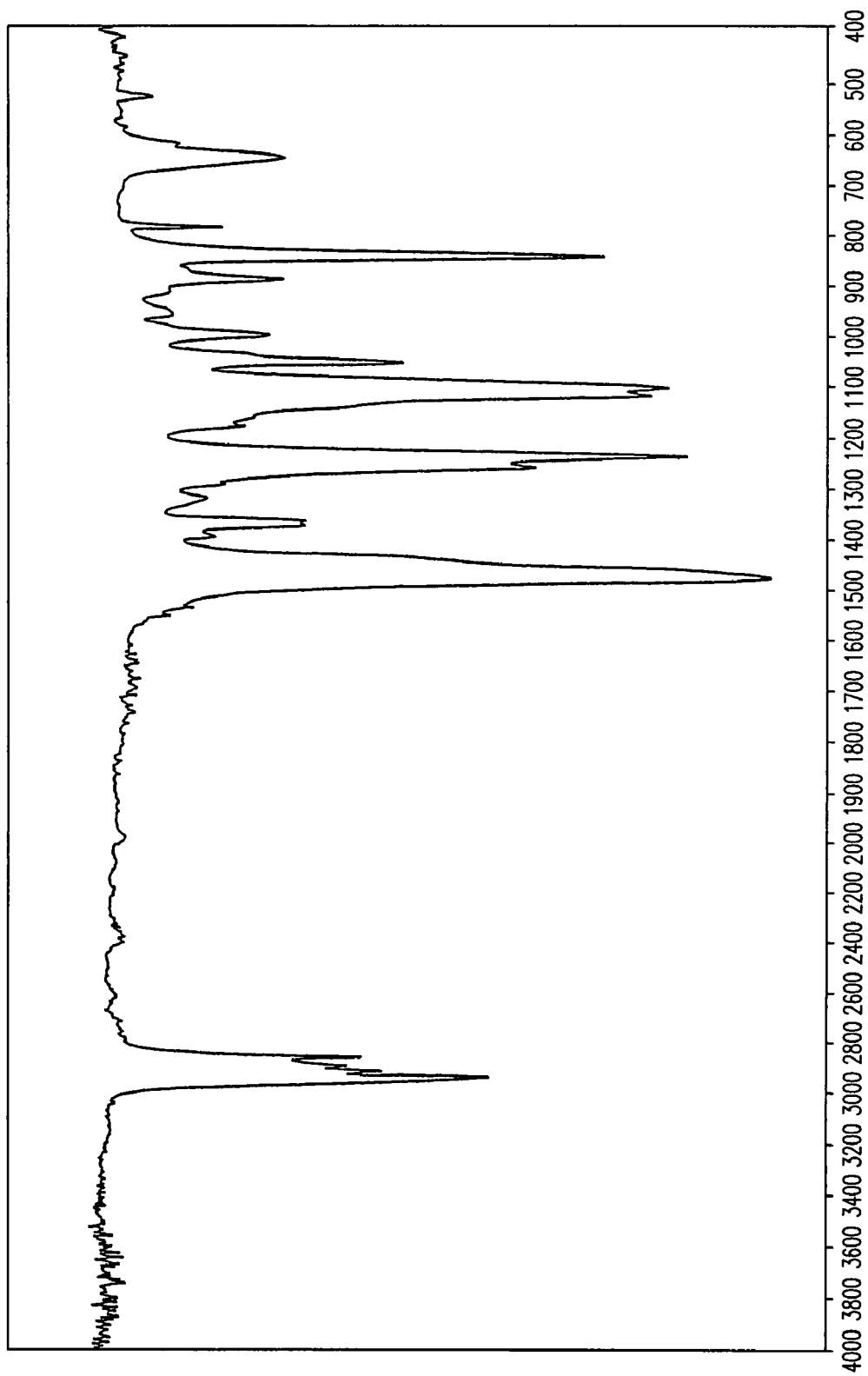

FIG. 18 is a chart of an IR absorption spectrum of a sample obtained by storing the synthetic substance obtained in Example 41, in the atmosphere.

BEST MODE FOR CARRYING OUT THE INVENTION

The present invention is described in detail hereinafter.

Thiol Compound Derivative

The thiol compound derivative according to the invention is a derivative of 1,3,5-triazene-2,4,6-trithiol, 1,3,5-triazine-2,4-dithiol or the like, and is a compound derivative wherein a hydrogen atom of a thiol group (—SH) of such a compound is replaced with a specific substituent. The thiol compound derivative can be obtained by reacting a thiol compound such as triazinethiol with a vinyl ether. Examples of the thiol compound derivatives are described below.

Trithiol Compound Derivative

The thiol compound derivative of the invention is, for example, a thiol compound derivative represented by the following formula (1), which is a derivative of a trithiol compound.

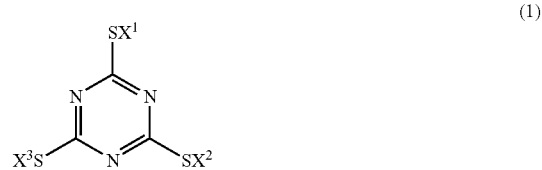

(1)

In the formula (1), $X^1$, $X^2$ and $X^3$ are each a group represented by the following formula (2).

(2)

In the formula (1), $X^1$, $X^2$ and $X^3$ may be the same or different, preferably the same.

In the formula (2), A is an oxygen atom or a sulfur atom.

$R^1$ is a hydrogen atom, an alkyl group or a phenyl group. $R^1$ is preferably a hydrogen atom or an alkyl group, more preferably a hydrogen atom.

$R^2$ is a group selected from the group consisting of the following groups (a) to (f). In the present invention, a group selected from the groups (a) to (e) is preferable.

(a) A group selected from an alkyl group, a halogenated alkyl group, an alkyl group having at least one hydroxyl group, an alkenyl group, an alkynyl group and an aralkyl group. Of these, preferable is an alkyl group or an alkenyl group.

The alkyl group is preferably an alkyl group of 1 to 25 carbon atoms, more preferably an alkyl group of 1 to 18 carbon atoms. The alkyl group may be any of straight-chain, branched and cyclic alkyl groups. Examples of such alkyl groups include methyl, ethyl, n-propyl, isopropyl, n-butyl, isobutyl, sec-butyl, tert-butyl, pentyl, hexyl, heptyl, octyl, 2-ethylhexyl, decyl, cetyl, stearyl and 1-menthyl. Of these, methyl, ethyl and n-propyl are preferable.

The halogenated alkyl group is, for example, a group wherein at least one hydrogen atom of the above alkyl group is replaced with halogen. Examples of the halogen atoms include a fluorine atom, a chlorine atom, a bromine atom and an iodine atom. Of these, a fluorine atom is preferable. Examples of the halogenated alkyl groups containing a fluorine atom include a perfluoroalkyl group wherein all hydrogen atoms of the above alkyl group are replaced with fluorine atoms, and a fluoroalkyl group represented by RfCH$_2$CH$_2$—. The Rf is, for example, perfluoromethyl, perfluoroethyl, perfluoropropyl or perfluorobutyl.

The alkyl group having one or more hydroxyl groups is, for example, a group wherein at least one hydrogen atom of the above alkyl group is replaced with a hydroxyl group. The alkyl group having one or more hydroxyl groups is preferably a group having one or two hydroxyl groups, more preferably a group having one hydroxyl group. The hydroxyl group may be any of primary, secondary and tertiary. Examples of the alkyl groups having such a hydroxyl group include alkyl groups having a primary hydroxyl group, such as 2-hydroxyethyl, 3-hydroxypropyl and 4-hydroxy-n-butyl, alkyl groups having a secondary hydroxyl group, such as 1-hydroxyethyl, 2-hydroxypropyl and 3-hydroxy-n-butyl, and alkyl groups having a tertiary hydroxyl group, such as 3-hydroxy-3-methyl-n-butyl.

The alkenyl group is preferably an alkenyl group of 1 to 20 carbon atoms, more preferably an alkenyl group of 1 to 10 carbon atoms. Examples of such alkenyl groups include propanedienyl, isopropenyl, 3-methyl-2-butenyl, allyl and 2-methylallyl. Of these, isopropenyl and allyl are preferable.

The alkynyl group is preferably an alkynyl group of 1 to 20 carbon atoms, more preferably an alkynyl group of 1 to 10 carbon atoms. Examples of such alkynyl groups include propargyl and 1-phenylpropargyl. Of these, propargyl is preferable.

The aralkyl group is preferably an aralkyl group of 1 to 20 carbon atoms, more preferably an aralkyl group of 1 to 10 carbon atoms. Examples of such aralkyl groups include 4-phenylbutyl and methylbenzyl. Of these, methylbenzyl is preferable.

(b) A residue wherein a hydroxyl group is removed from a hydroxyl group-containing compound selected from alkylene glycol, dialkylene glycol, trialkylene glycol, tetraalkylene glycol, allyl alcohols, ketooximes, trialkanolamines, dialkanolamines, alkanolamines, trialkylsilanol, alicyclic alcohol and naphthyl alcohols. Of these, polyalkylene glycols, such as dialkylene glycol, trialkylene glycol and tetraalkylene glycol, are preferable.

Examples of the glycols, such as dialkylene glycol, trialkylene glycol and tetraalkylene glycol, include ethylene glycol, propylene glycol, butylene glycol, diethylene glycol, dipropylene glycol, dibutylene glycol, diethylene glycol monobutyl ether, triethylene glycol, tripropylene glycol, tributylene glycol, tetraethylene glycol, tetrapropylene glycol and tetrabutylene glycol. Of these, ethylene glycol is preferable.

Examples of the ketooximes include acetone ketooxime and methyl ethyl ketone ketooxime.

Examples of the trialkanolamines include triethanolamine and tripropanolamine.

Examples of the dialkanolamines include diethanolamine and dipropanolamine.

Examples of the monoalkanolamines include 4-dimethylaminobutanol and 3-dimethylaminopropanol.

Examples of the trialkylsilanols include trimethylsilyl alcohol and triethylsilyl alcohol.

Examples of the alicyclic alcohols include cyclohexyl alcohol and menthol.

Examples of the naphthyl alcohols include naphthyl alcohol.

(c) A group represented by the following formula (3):

—CHY—CH$_2$X       (3)

wherein X is a halogen atom, an alkoxy group, an alkoxyalkoxy group, a dialkylamino group, a trialkylsilyl group, an acetoxy group, a piperidino group or the like, and Y is a hydrogen atom or a halogen atom.

X is preferably a halogen atom, an alkoxy group or a dialkylamino group.

Examples of the groups represented by the formula (3) include 1-chloroethyl, 2-chloroethyl, 1-bromoethyl, 2-bromoethyl, methoxyethyl, 2-butoxyethyl, methoxyethoxyethyl, dimethylaminoethyl, 2-(diethylamino)ethyl, aminoethyl, trimethylsilylethyl, trimethylsiloxyethyl, 2-acetoxyethyl and 2-piperidinoethyl. Of these, 2-chloroethyl and methoxyethyl are particularly preferable.

(d) A group represented by the following formula (4):

(4)

wherein n is an integer of 1 to 3, preferably 1, and is a number of substituents Z bonded to the phenyl group skeleton.

In the formula (4), Z is a hydrogen atom, a halogen atom, a nitro group, an amino group, an alkoxy group, an alkylamino group, a dialkylamino group, an alkyl group, an acyl group or the like.

Examples of the groups represented by the formula (4) include phenyl, methoxyphenyl, tolyl such as o-tolyl, isopropylphenyl, p-nitrophenyl, 2-nitrophenyl, 3-nitrophenyl, fluorophenyl such as p-fluorophenyl, methoxyphenyl such as p-methoxyphenyl, aminophenyl such as p-aminophenyl, N-methylaminophenyl, p-(dimethylamino)phenyl, 4-acetylphenyl, iodophenyl such as p-iodophenyl, chlorophenyl such as p-chlorophenyl, bromophenyl such as p-bromophenyl, 2,4,6-trichlorophenyl, 2,4,6-trimethylphenyl, 2,4,6-tribromophenyl, 2,4-dichlorophenyl, 2,4-dibromophenyl and 2,4-dimethylphenyl. Of these, phenyl and methoxyphenyl are preferable.

(e) A group represented by —CH$_2$—C$_6$H$_5$ or —CHCH$_3$—C$_6$H$_5$, namely, 1-phenylethyl or benzyl.

(f) A group represented by the following formula (5) or (6):

   (5)

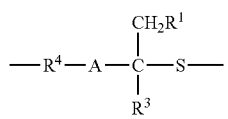   (6)

In the formula (6), R$^1$ and R$^3$ are the same as R$^1$ and R$^3$ in the formula (2). In the formulas (5) and (6), A is an oxygen atom or a sulfur atom, and R$^4$ is a divalent substituent, is any one of —CH$_2$—, —CH$_2$CH$_2$—, —CH$_2$CH$_2$CH$_2$—, CH$_2$CH$_2$CH$_2$CH$_2$—, —CH$_2$CH$_2$OCH$_2$CH$_2$—, —CH$_2$CH$_2$OCH$_2$CH$_2$OCH$_2$CH$_2$—,

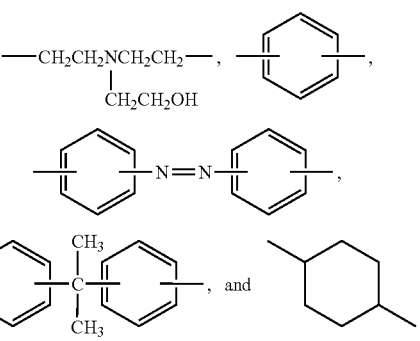

Particularly preferable is a thiol compound derivative wherein in the formula (2), A is an oxygen atom, R$^1$ is a hydrogen atom, R$^2$ is an alkyl group or a residue wherein a hydroxyl group is removed from (poly)alkylene glycol, and R$^3$ is a hydrogen atom.

In the thiol compound derivative of the invention, R$^1$ and R$^2$ in the formula (2) may form a ring. When R$^1$ and R$^2$ form a ring, R$^1$ and R$^2$ are each preferably an alkyl group, and the alkyl group may have a substituent.

In the above case, R$^3$ is preferably a hydrogen atom, and the ring formed from R$^1$ and R$^2$ is preferably represented by the following formula (7):

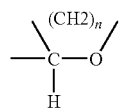   (7)

wherein n is 3 or 4.

The above-mentioned cyclic structure part may have a substituent.

Another thiol compound derivative according to the present invention is a thiol compound derivative represented by the following formula (8):

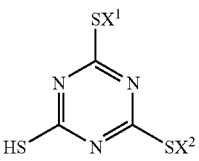   (8)

wherein X$^1$ and X$^2$ are each a group represented by the following formula (2):

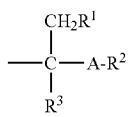   (2)

In the formula (8), X$^1$ and X$^2$ may be the same or different, preferably the same. The formula (2) is the same as that previously described.

Another thiol compound derivative according to the present invention is a thiol compound derivative represented by the following formula (9):

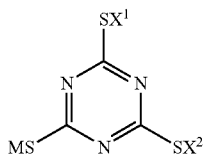   (9)

wherein X$^1$ and X$^2$ are each a group represented by the following formula (2):

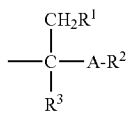   (2)

In the formula (9), X$^1$ and X$^2$ may be the same or different, preferably the same, and M is an alkali metal or an alkaline earth metal. The alkali metal is preferably sodium or potassium, more preferably sodium. The alkaline earth metal is preferably calcium, magnesium or barium. Of these, sodium is preferable. The formula (2) is the same as that previously described.

Examples of the thiol compound derivatives represented by the formula (1) (sometimes referred to as "derivative a" hereinafter) wherein X$^1$, X$^2$ and X$^3$ are the same and X$^1$ is represented by the following formula (2) include thiol compound derivatives shown in the following Table 1 (Tables 1-1 to 1-4).

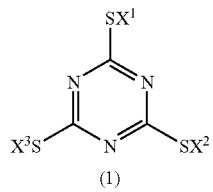

(1)

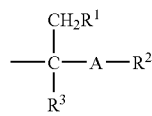

(2)

Tables 1-1

| Thiol compound derivative | Derivative | A | R³ | R¹ | R² |
|---|---|---|---|---|---|
| a1 | a | O | H | H | methyl group |
| a2 | a | O | H | H | ethyl group |
| a3 | a | O | H | H | n-propyl group |
| a4 | a | O | H | H | isopropyl group |
| a5 | a | O | H | H | n-butyl group |
| a6 | a | O | H | H | isobutyl group |
| a7 | a | O | H | H | sec-butyl group |
| a8 | a | O | H | H | tert-butyl group |
| a9 | a | O | H | H | pentyl group |
| a10 | a | O | H | H | hexyl group |
| a11 | a | O | H | H | heptyl group |
| a12 | a | O | H | H | octyl group |
| a13 | a | O | H | H | 2-ethylhexyl group |
| a14 | a | O | H | H | decyl group |
| a15 | a | O | H | H | cetyl group |
| a16 | a | O | H | H | stearyl group |
| a17 | a | O | H | H | 1-menthyl group |
| a18 | a | O | H | H | propanedienyl group |
| a19 | a | O | H | H | isopropenyl group |
| a20 | a | O | H | H | 3-butynyl group |
| a21 | a | O | H | H | 3-methyl-2-butenyl |
| a22 | a | O | H | H | allyl group |
| a23 | a | O | H | H | 2-methylallyl group |
| a24 | a | O | H | H | propargyl group |
| a25 | a | O | H | H | 3-phenylpropargyl |
| a26 | a | O | H | H | residue wherein one hydroxyl group of ethylene glycol is removed |
| a27 | a | O | H | H | residue wherein one hydroxyl group of propylene glycol is removed |
| a28 | a | O | H | H | residue wherein one hydroxyl group of butylene glycol is removed |
| a29 | a | O | H | H | residue wherein one hydroxyl group of diethylene glycol is removed |
| a30 | a | O | H | H | residue wherein one hydroxyl group of dipropylene glycol is removed |
| a31 | a | O | H | H | residue wherein one hydroxyl group of dibutylene glycol is removed |
| a32 | a | O | H | H | residue wherein one hydroxyl group of diethylene glycol monobutyl ether is removed |
| a33 | a | O | H | H | residue wherein one hydroxyl group of triethylene glycol is removed |
| a34 | a | O | H | H | residue wherein one hydroxyl group of tripropylene glycol is removed |
| a35 | a | O | H | H | residue wherein one hydroxyl group of tributylene glycol is removed |

Tables 1-2

| Thiol compound derivative | Derivative | A | R³ | R¹ | R² |
|---|---|---|---|---|---|
| a36 | a | O | H | H | residue wherein one hydroxyl group of tetraethylene glycol is removed |

-continued

| | | | | | |
|---|---|---|---|---|---|
| a37 | a | O | H | H | residue wherein one hydroxyl group of tetrapropylene glycol is removed |
| a38 | a | O | H | H | residue wherein one hydroxyl group of tetrabutylene glycol is removed |
| a39 | a | O | H | H | residue wherein one hydroxyl group of acetone oxime group is removed |
| a40 | a | O | H | H | residue wherein one hydroxyl group of triethanolamine is removed |
| a41 | a | O | H | H | residue wherein one hydroxyl group of diethanolamine is removed |
| a42 | a | O | H | H | residue wherein one hydroxyl group of dimethylaminoethanol is removed |
| a43 | a | O | H | H | residue wherein one hydroxyl group of trimethylsilyl alcohol is removed |
| a44 | a | O | H | H | residue wherein one hydroxyl group of triethylsilyl alcohol is removed |
| a45 | a | O | H | H | residue wherein one hydroxyl group of cyclohexyl alcohol is removed |
| a46 | a | O | H | H | residue wherein one hydroxyl group of menthol is removed |
| a47 | a | O | H | H | residue wherein one hydroxyl group of naphthyl alcohol is removed |
| a48 | a | O | H | H | 1-chloroethyl group |
| a49 | a | O | H | H | 2-chloroethyl group |
| a50 | a | O | H | H | 1-bromoethyl group |
| a51 | a | O | H | H | 2-bromoethyl group |
| a52 | a | O | H | H | methoxyethyl group |
| a53 | a | O | H | H | 2-butoxyethyl group |
| a54 | a | O | H | H | methoxyethoxyethyl group |
| a55 | a | O | H | H | dimethylaminoethyl group |
| a56 | a | O | H | H | 2-(diethylamino)ethyl group |
| a56 | a | O | H | H | 3-dimethylaminopropyl group |
| a57 | a | O | H | H | aminoethyl group |
| a58 | a | O | H | H | trimethylsilylethyl group |
| a59 | a | O | H | H | trimethylsiloxyethyl group |
| a60 | a | O | H | H | 2-acetoxyethyl group |
| a61 | a | O | H | H | 2-piperidinoethyl group |
| a62 | a | O | H | H | phenyl group |
| a63 | a | O | H | H | methoxyphenyl group |
| a64 | a | O | H | H | o-tolyl group |
| a65 | a | O | H | H | o-isopropylphenyl group |
| a66 | a | O | H | H | p-nitrophenyl group |
| a67 | a | O | H | H | 2-nitrophenyl group |
| a68 | a | O | H | H | 3-nitrophenyl group |
| a69 | a | O | H | H | p-fluorophenyl group |
| a70 | a | O | H | H | p-methoxyphenyl group |

Tables 1-3

| Thiol compound derivative | Derivative | A | $R^3$ | $R^1$ | $R^2$ |
|---|---|---|---|---|---|
| a71 | a | O | H | H | p-aminophenyl group |
| a72 | a | O | H | H | N-methylaminophenyl group |
| a73 | a | O | H | H | p-(dimethylamino)phenyl group |
| a74 | a | O | H | H | 4-acetylphenyl group |
| a75 | a | O | H | H | p-iodophenyl group |
| a76 | a | O | H | H | p-chlorophenyl group |
| a77 | a | O | H | H | p-bromophenyl group |
| a78 | a | O | H | H | 2,4,6-trichlorophenyl group |
| a79 | a | O | H | H | 2,4,6-tribromophenyl group |
| a80 | a | O | H | H | 2,4,6-trimethylphenyl group |
| a81 | a | O | H | H | 2,4-dichlorophenyl group |
| a82 | a | O | H | H | 2,4-dibromophenyl group |
| a83 | a | O | H | H | 2,4-dimethylphenyl group |
| a84 | a | O | H | H | —$CH_2OCH$=$CH_2$ |
| a85 | a | O | H | H | —$CH_2CH_2OCH$=$CH_2$ |
| a86 | a | O | H | H | —$CH_2CH_2CH_2OCH$=$C_2$ |
| a87 | a | O | H | H | —$CH_2CH_2CH_2CH_2OCH$=$CH_2$ |
| a88 | a | O | H | H | —$CH_2CH_2OCH_2CH_2OCH$=$CH_2$ |
| a89 | a | O | H | H | —$CH_2CH_2OCH_2CH_2OCH_2CH_2OCH$=$CH_2$ |
| a90 | a | O | H | H | —$CH_2CH_2N(CH_2CH_2OH)CH_2CH_2OCH$=$CH_2$ |
| a91 | a | O | H | H | —Ph—$OCH$=$CH_2$ |
| a92 | a | O | H | H | —Ph—N=N—Ph—$OCH$=$CH_2$ |
| a93 | a | O | H | H | —Ph—$C(CH_3)_2$—Ph—$OCH$=$CH_2$ |
| a94 | a | O | H | H | -cyclohexylene-$OCH$=$CH_2$ |

-continued

| | | | | | |
|---|---|---|---|---|---|
| a95 | a | O | H | H | 1-phenylethyl group |
| a96 | a | O | H | H | benzyl group |
| a97 | a | 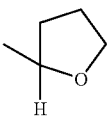 | | | |
| a98 | a | 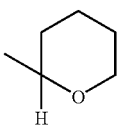 | | | |

Tables 1-4

| Thiol compound derivative | Derivative | A | $R^3$ | $R^1$ | $R^2$ |
|---|---|---|---|---|---|
| a99 | a | 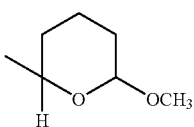 | | | |
| a100 | a | 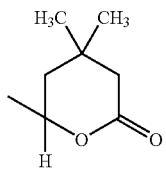 | | | |
| a101 | a | 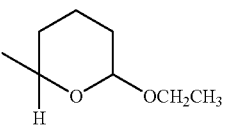 | | | |
| a102 | a | S | H | H | 3-(trimethylsilyl)propyl group |
| a103 | a | S | H | H | 2-hydroxyethyl group |
| a104 | a | S | H | H | 2-(N-morpholino)ethyl group |
| a105 | a | S | H | H | 2-(N-β-hydroxyethyl)aminoethyl group |
| a106 | a | S | H | H | 2-aminoethyl group |
| a107 | a | S | H | H | p-chlorophenyl group |
| a108 | a | S | H | H | phenyl group |
| a109 | a | S | H | H | vinyl group |
| a110 | a | O | Me | H | methyl group |
| a111 | a | O | Me | H | ethyl group |
| a112 | a | O | Et | H | methyl group |
| a113 | a | O | Et | H | ethyl group |
| a114 | a | O | Ph— | H | methyl group |
| a115 | a | O | Ph— | H | ethyl group |

In Table 1, "-Ph-" denotes a divalent aromatic substituent represented by $C_6H_4$; "cyclohexylene" denotes a divalent substituent having cyclohexylene skeleton represented by $C_6H_{10}$; "Ph-" denotes a monovalent aromatic substituent represented by $C_6H_5$; "Me" denotes a methyl group; "Et" denotes an ethyl group; and

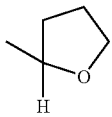

(thiol compound derivative a97) denotes a substituent $X^1$ wherein A is an oxygen atom, substituents $R^1$ and $R^2$ form a ring, and $R^3$ is a hydrogen atom. Each of the thiol compound derivatives a98 to a101 has the same meaning as that of the thiol compound derivative a97.

Examples of the thiol compound derivatives represented by the formula (8) (sometimes referred to as "derivative b" hereinafter) wherein $X^1$ and $X^2$ are the same and $X^1$ is represented by the following formula (2) include thiol compound derivatives shown in the following Table 2 (Tables 2-1 to 2-4).

(derivative b)

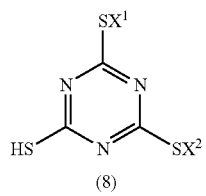

(8)

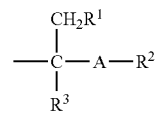

(2)

Tables 2-1

| Thiol compound derivative | Derivative | A | $R^3$ | $R^1$ | $R^2$ |
|---|---|---|---|---|---|
| b1 | b | O | H | H | methyl group |
| b2 | b | O | H | H | ethyl group |
| b3 | b | O | H | H | n-propyl group |
| b4 | b | O | H | H | isopropyl group |
| b5 | b | O | H | H | n-butyl group |
| b6 | b | O | H | H | isobutyl group |
| b7 | b | O | H | H | sec-butyl group |
| b8 | b | O | H | H | tert-butyl group |
| b9 | b | O | H | H | pentyl group |
| b10 | b | O | H | H | hexyl group |
| b11 | b | O | H | H | heptyl group |
| b12 | b | O | H | H | octyl group |
| b13 | b | O | H | H | 2-ethylhexyl group |
| b14 | b | O | H | H | decyl group |
| b15 | b | O | H | H | cetyl group |
| b16 | b | O | H | H | stearyl group |
| b17 | b | O | H | H | 1-menthyl group |
| b18 | b | O | H | H | propanedienyl group |
| b19 | b | O | H | H | isopropenyl group |
| b20 | b | O | H | H | 3-butynyl group |
| b21 | b | O | H | H | 3-methyl-2-butenyl group |
| b22 | b | O | H | H | allyl group |
| b23 | b | O | H | H | 2-methylallyl group |
| b24 | b | O | H | H | propargyl group |
| b25 | b | O | H | H | 3-phenylpropargyl group |
| b26 | b | O | H | H | residue wherein one hydroxyl group of ethylene glycol is removed |
| b27 | b | O | H | H | residue wherein one hydroxyl group of propylene glycol is removed |
| b28 | b | O | H | H | residue wherein one hydroxyl group of butylene glycol is removed |
| b29 | b | O | H | H | residue wherein one hydroxyl group of diethylene glycol is removed |

-continued

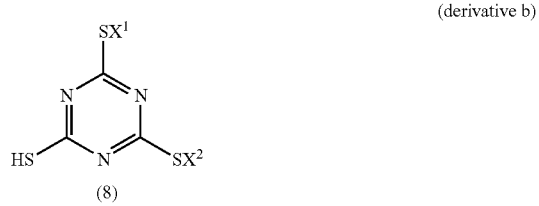

(derivative b)

(8)

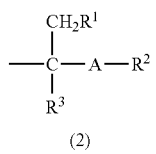

(2)

| Thiol compound derivative | Derivative | A | R³ | R¹ | R² |
|---|---|---|---|---|---|
| b30 | b | O | H | H | residue wherein one hydroxyl group of dipropylene glycol is removed |
| b31 | b | O | H | H | residue wherein one hydroxyl group of dibutylene glycol is removed |
| b32 | b | O | H | H | residue wherein one hydroxyl group of diethylene glycol monobutyl ether is removed |
| b33 | b | O | H | H | residue wherein one hydroxyl group of triethylene glycol is removed |
| b34 | b | O | H | H | residue wherein one hydroxyl group of tripropylene glycol is removed |
| b35 | b | O | H | H | residue wherein one hydroxyl group of tributylene glycol is removed |

Tables 2-2

| Thiol compound derivative | Derivative | A | R³ | R¹ | R² |
|---|---|---|---|---|---|
| b36 | b | O | H | H | residue wherein one hydroxyl group of tetraethylene glycol is removed |
| b37 | b | O | H | H | residue wherein one hydroxy group of tetrapropylene glycol is removed |
| b38 | b | O | H | H | residue wherein one hydroxyl group of tetrabutylene glycol is removed |
| b39 | b | O | H | H | residue wherein a hydroxyl group of acetone oxime group is removed |
| b40 | b | O | H | H | residue wherein one hydroxyl group of triethanolamine is removed |
| b41 | b | O | H | H | residue wherein one hydroxyl group of diethanolamine is removed |
| b42 | b | O | H | H | residue wherein a hydroxyl group of dimethylaminoethanol is removed |
| b43 | b | O | H | H | residue wherein a hydroxyl group of trimethylsilyl alcohol is removed |
| b44 | b | O | H | H | residue wherein a hydroxyl group of triethylsilyl alcohol is removed |
| b45 | b | O | H | H | residue wherein a hydroxyl group of cyclohexyl alcohol is removed |
| b46 | b | O | H | H | residue wherein a hydroxyl group of menthol is removed |
| b47 | b | O | H | H | residue wherein a hydroxyl group of naphthyl alcohol is removed |

-continued

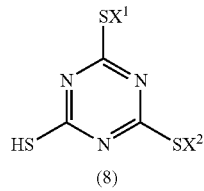

(derivative b)

(8)

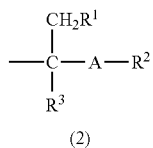

(2)

| | | | | | |
|---|---|---|---|---|---|
| b48 | b | O | H | H | 1-chloroethyl group |
| b49 | b | O | H | H | 2-chloroethyl group |
| b50 | b | O | H | H | 1-bromoethyl group |
| b51 | b | O | H | H | 2-bromoethyl group |
| b52 | b | O | H | H | methoxyethyl group |
| b53 | b | O | H | H | 2-butoxyethyl group |
| b54 | b | O | H | H | methoxyethoxyethyl group |
| b55 | b | O | H | H | dimethylaminoethyl group |
| b56 | b | O | H | H | 2-(diethylamino)ethyl group |
| b56 | b | O | H | H | 3-dimethylaminopropyl group |
| b57 | b | O | H | H | aminoethyl group |
| b58 | b | O | H | H | trimethylsilylethyl group |
| b59 | b | O | H | H | trimethylsiloxyethyl group |
| b60 | b | O | H | H | 2-acetoxyethyl group |
| b61 | b | O | H | H | 2-piperidinoethyl group |
| b62 | b | O | H | H | phenyl group |
| b63 | b | O | H | H | methoxyphenyl group |
| b64 | b | O | H | H | o-tolyl group |
| b65 | b | O | H | H | o-isopropylphenyl group |
| b66 | b | O | H | H | p-nitrophenyl group |
| b67 | b | O | H | H | 2-nitrophenyl group |
| b68 | b | O | H | H | 3-nitrophenyl group |
| b69 | b | O | H | H | p-fluorophenyl group |
| b70 | b | O | H | H | p-methoxyphenyl group |

Tables 2-3

| Thiol compound derivative | Derivative | A | $R^3$ | $R^1$ | $R^2$ |
|---|---|---|---|---|---|
| b71 | b | O | H | H | p-aminophenyl group |
| b72 | b | O | H | H | N-methylaminophenyl group |
| b73 | b | O | H | H | p-(dimethylamino)phenyl group |
| b74 | b | O | H | H | 4-acetylphenyl group |
| b75 | b | O | H | H | p-iodophenyl group |
| b76 | b | O | H | H | p-chlorophenyl group |
| b77 | b | O | H | H | p-bromophenyl group |
| b78 | b | O | H | H | 2,4,6-trichlorophenyl group |
| b79 | b | O | H | H | 2,4,6-tribromophenyl group |
| b80 | b | O | H | H | 2,4,6-trimethylphenyl group |
| b81 | b | O | H | H | 2,4-dichlorophenyl group |
| b82 | b | O | H | H | 2,4-dibromophenyl group |
| b83 | b | O | H | H | 2,4-dimethylphenyl group |
| b84 | b | O | H | H | —CH$_2$OCH=CH$_2$ |
| b85 | b | O | H | H | —CH$_2$CH$_2$OCH=CH$_2$ |
| b86 | b | O | H | H | —CH$_2$CH$_2$CH$_2$OCH=CH$_2$ |
| b87 | b | O | H | H | —CH$_2$CH$_2$CH$_2$CH$_2$OCH=CH$_2$ |
| b88 | b | O | H | H | —CH$_2$CH$_2$OCH$_2$CH$_2$OCH=CH$_2$ |
| b89 | b | O | H | H | —CH$_2$CH$_2$OCH$_2$CH$_2$OCH$_2$CH$_2$OCH=CH$_2$ |
| b90 | b | O | H | H | —CH$_2$CH$_2$N(CH$_2$CH$_2$OH)CH$_2$CH$_2$OCH=CH$_2$ |
| b91 | b | O | H | H | —Ph—OCH=CH$_2$ |
| b92 | b | O | H | H | —Ph—N=N—Ph—OCH=CH$_2$ |
| b93 | b | O | H | H | —Ph—C(CH$_3$)$_2$—Ph—OCH=CH$_2$ |
| b94 | b | O | H | H | -cyclohexylene-OCH=CH$_2$ |
| b95 | b | O | H | H | 1-phenylethyl group |
| b96 | b | O | H | H | benzyl group |

-continued

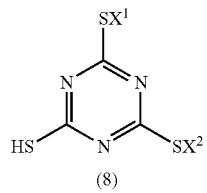

(8) (derivative b)

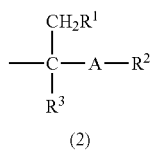

(2)

| | | |
|---|---|---|
| b97 | b | 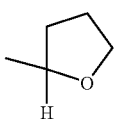 |
| b98 | b | 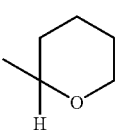 |
| b99 | b | 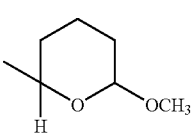 |

Tables 2-4

| Thiol compound derivative | Derivative | A | $R^3$ | $R^1$ | $R^2$ |
|---|---|---|---|---|---|
| b100 | b | | | |  |
| b101 | b | | | |  |
| b102 | b | S | H | H | 3-(trimethylsilyl)propyl group |
| b103 | b | S | H | H | 2-hydroxyethyl group |
| b104 | b | S | H | H | 2-(N-morpholino)ethyl group |
| b105 | b | S | H | H | 2-(N-β-hydroxyethyl)aminoethyl group |
| b106 | b | S | H | H | 2-aminoethyl group |
| b107 | b | S | H | H | p-chlorophenyl group |
| b108 | b | S | H | H | phenyl group |
| b109 | b | S | H | H | vinyl group |
| b110 | b | O | Me | H | methyl group |
| b111 | b | O | Me | H | ethyl group |
| b112 | b | O | Et | H | methyl group |
| b113 | b | O | Et | H | ethyl group |
| b114 | b | O | Ph— | H | methyl group |
| b115 | b | O | Ph— | H | ethyl group |

Examples of the thiol compound derivatives represented by the formula (9) (sometimes referred to as "derivative c" hereinafter) wherein $X^1$ and $X^2$ are the same and $X^1$ is represented by the following formula (2) include thiol compound derivatives shown in the following Table 3 (Tables 3-1 to 3-4).

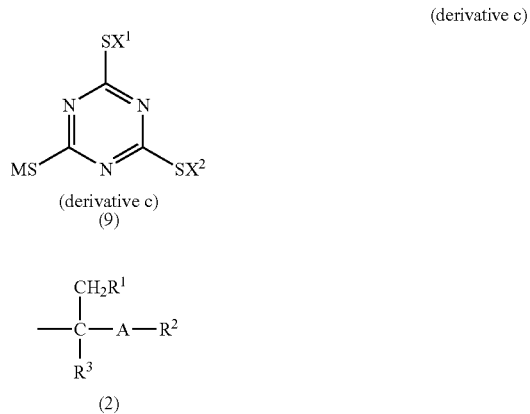

(derivative c)
(9)

(2)

Tables 3-1

| Thiol compound derivative | Derivative | M | A | $R^3$ | $R^1$ | $R^2$ |
|---|---|---|---|---|---|---|
| c1 | c | Na | O | H | H | methyl group |
| c2 | c | Na | O | H | H | ethyl group |
| c3 | c | Na | O | H | H | n-propyl group |
| c4 | c | Na | O | H | H | isopropyl group |
| c5 | c | Na | O | H | H | n-butyl group |
| c6 | c | Na | O | H | H | isobutyl group |
| c7 | c | Na | O | H | H | sec-butyl group |
| c8 | c | Na | O | H | H | tert-butyl group |
| c9 | c | Na | O | H | H | pentyl group |
| c10 | c | Na | O | H | H | hexyl group |
| c11 | c | Na | O | H | H | heptyl group |
| c12 | c | Na | O | H | H | octyl group |
| c13 | c | Na | O | H | H | 2-ethylhexyl group |
| c14 | c | Na | O | H | H | decyl group |
| c15 | c | Na | O | H | H | cetyl group |
| c16 | c | Na | O | H | H | stearyl group |
| c17 | c | Na | O | H | H | 1-methyl group |
| c18 | c | Na | O | H | H | propanedienyl group |
| c19 | c | Na | O | H | H | isopropenyl group |
| c20 | c | Na | O | H | H | 3-butynyl group |
| c21 | c | Na | O | H | H | 3-methyl-2-butenyl group |
| c22 | c | Na | O | H | H | allyl group |
| c23 | c | Na | O | H | H | 2-methylallyl group |
| c24 | c | Na | O | H | H | propargyl group |
| c25 | c | Na | O | H | H | 3-phenylpropargyl group |
| c26 | c | Na | O | H | H | residue wherein one hydroxyl group of ethylene glycol is removed |
| c27 | c | Na | O | H | H | residue wherein one hydroxyl group of propylene glycol is removed |
| c28 | c | Na | O | H | H | residue wherein one hydroxyl group of butylene glycol is removed |
| c29 | c | Na | O | H | H | residue wherein one hydroxyl group of diethylene glycol is removed |
| c30 | c | Na | O | H | H | residue wherein one hydroxyl group of dipropylene glycol is removed |
| c31 | c | Na | O | H | H | residue wherein one hydroxyl group of dibutylene glycol is removed residue wherein one hydroxyl group |

-continued

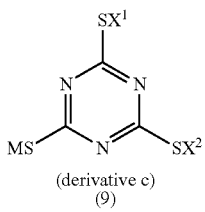

(derivative c)
(9)

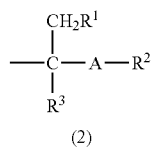

(2)

| | | | | | | |
|---|---|---|---|---|---|---|
| c32 | c | Na | O | H | H | of diethylene glycol monobutyl ether is removed |

Tables 3-2

| Thiol compound derivative | Derivative | M | A | R³ | R¹ | R² |
|---|---|---|---|---|---|---|
| c33 | c | Na | O | H | H | residue wherein one hydroxyl group of triethylene glycol is removed |
| c34 | c | Na | O | H | H | residue wherein one hydroxyl group of tripropylene glycol is removed |
| c35 | c | Na | O | H | H | residue wherein one hydroxyl group of tributylene glycol is removed |
| c36 | c | Na | O | H | H | residue wherein one hydroxyl group of tetraethylene glycol is removed |
| c37 | c | Na | O | H | H | residue wherein one hydroxyl group of tetrapropylene glycol is removed |
| c38 | c | Na | O | H | H | residue wherein one hydroxyl group of tetrabutylene glycol is removed |
| c39 | c | Na | O | H | H | residue wherein a hydroxyl group of acetone oxime group is removed |
| c40 | c | Na | O | H | H | residue wherein one hydroxyl group of triethanolamine is removed |
| c41 | c | Na | O | H | H | residue wherein one hydroxyl group of diethanolamine is removed |
| c42 | c | Na | O | H | H | residue wherein a hydroxyl group of dimethylaminoethanol is removed |
| c43 | c | Na | O | H | H | residue wherein a hydroxyl group of trimethylsilyl alcohol is removed |
| c44 | c | Na | O | H | H | residue wherein a hydroxyl group of triethyisilyl alcohol is removed |
| c45 | c | Na | O | H | H | residue wherein a hydroxyl group of cyclohexyl alcohol is removed |
| c46 | c | Na | O | H | H | residue wherein a hydroxyl group of menthol is removed |
| c47 | c | Na | O | H | H | residue wherein a hydroxyl group of naphthyl alcohol is removed |
| c48 | c | Na | O | H | H | 1-chloroethyl group |
| c49 | c | Na | O | H | H | 2-chloroethyl group |
| c50 | c | Na | O | H | H | 1-bromoethyl group |
| c51 | c | Na | O | H | H | 2-bromoethyl group |
| c52 | c | Na | O | H | H | methoxyethyl group |
| c53 | c | Na | O | H | H | 2-butoxyethyl group |
| c54 | c | Na | O | H | H | methoxyethoxyethyl group |
| c55 | c | Na | O | H | H | dimethylaminoethyl group |
| c56 | c | Na | O | H | H | 2-(diethylamino)ethyl group |
| c56 | c | Na | O | H | H | 3-dimethylaminopropyl group |
| c57 | c | Na | O | H | H | aminoethyl group |

-continued

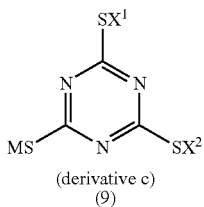

(derivative c)
(9)

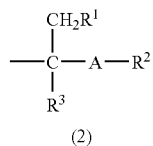

(2)

| | | | | | | |
|---|---|---|---|---|---|---|
| c58 | c | Na | O | H | H | trimethylsilylethyl group |
| c59 | c | Na | O | H | H | trimethylsiloxyethyl group |

Tables 3-3

| Thiol compound derivative | Derivative | M | A | $R^3$ | $R^1$ | $R^2$ |
|---|---|---|---|---|---|---|
| c60 | c | Na | O | H | H | 2-acetoxyethyl group |
| c61 | c | Na | O | H | H | 2-piperidinoethyl group |
| c62 | c | Na | O | H | H | phenyl group |
| c63 | c | Na | O | H | H | methoxyphenyl group |
| c64 | c | Na | O | H | H | o-tolyl group |
| c65 | c | Na | O | H | H | o-isopropylphenyl group |
| c66 | c | Na | O | H | H | p-nitrophenyl group |
| c67 | c | Na | O | H | H | 2-nitrophenyl group |
| c68 | c | Na | O | H | H | 3-nitrophenyl group |
| c69 | c | Na | O | H | H | p-fluorophenyl group |
| c70 | c | Na | O | H | H | p-methoxyphenyl group |
| c71 | c | Na | O | H | H | p-aminophenyl group |
| c72 | c | Na | O | H | H | N-methylaminophenyl group |
| c73 | c | Na | O | H | H | p-(dimethylamino)phenyl group |
| c74 | c | Na | O | H | H | 4-acetylphenyl group |
| c75 | c | Na | O | H | H | p-iodophenyl group |
| c76 | c | Na | O | H | H | p-chlorophenyl group |
| c77 | c | Na | O | H | H | p-bromophenyl group |
| c78 | c | Na | O | H | H | 2,4,6-trichlorophenyl group |
| c79 | c | Na | O | H | H | 2,4,6-tribromophenyl group |
| c80 | c | Na | O | H | H | 2,4,6-trimethylphenyl group |
| c81 | c | Na | O | H | H | 2,4-dichlorophenyl group |
| c82 | c | Na | O | H | H | 2,4-dibromophenyl group |
| c83 | c | Na | O | H | H | 2,4-dimethylphenyl group |
| c84 | c | Na | O | H | H | —$CH_2OCH=CH_2$ |
| c85 | c | Na | O | H | H | —$CH_2CH_2OCH=CH_2$ |
| c86 | c | Na | O | H | H | —$CH_2CH_2CH_2OCH=CH_2$ |
| c87 | c | Na | O | H | H | —$CH_2CH_2CH_2CH_2OCH=CH_2$ |
| c88 | c | Na | O | H | H | —$CH_2CH_2OCH_2CH_2OCH=CH_2$ |
| c89 | c | Na | O | H | H | —$CH_2CH_2OCH_2CH_2OCH_2CH_2OCH=CH_2$ |
| c90 | c | Na | O | H | H | —$CH_2CH_2N(CH_2CH_2OH)CH_2CH_2OCH=CH_2$ |
| c91 | c | Na | O | H | H | —Ph—$OCH=CH_2$ |
| c92 | c | Na | O | H | H | —Ph—N=N—Ph—$OCH=CH_2$ |
| c93 | c | Na | O | H | H | —Ph—$C(CH_3)_2$—Ph—$OCH=CH_2$ |
| c94 | c | Na | O | H | H | -cyclohexylene-$OCH=CH_2$ |

-continued

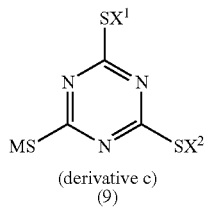

(derivative c)
(9)

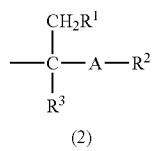

(2)

| | | | | | | |
|---|---|---|---|---|---|---|
| c95 | c | Na | O | H | H | 1-phenylethyl group |
| c96 | c | Na | O | H | H | benzyl group |

Tables 3-4

| Thiol compound derivative | Derivative | M | A | $R^3$ | $R^1$ | $R^2$ |
|---|---|---|---|---|---|---|
| c97 | c | Na | | | | 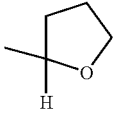 |
| c98 | c | Na | | | | 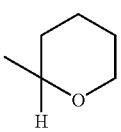 |
| c99 | c | Na | | | | 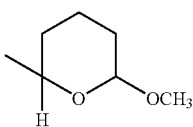 |
| c100 | c | Na | | | | 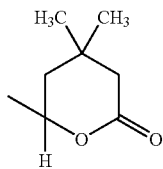 |
| c101 | c | Na | | | | 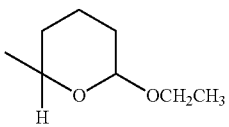 |
| c102 | c | Na | S | H | H | 3-(trimethylsilyl)propyl group |
| c103 | c | Na | S | H | H | 2-hydroxyethyl group |
| c104 | c | Na | S | H | H | 2-(N-morpholino)ethyl group |
| c105 | c | Na | S | H | H | 2-(N-β-hydroxyethyl)aminoethyl group |
| c106 | c | Na | S | H | H | 2-aminoethyl group |
| c107 | c | Na | S | H | H | p-chlorophenyl group |
| c108 | c | Na | S | H | H | phenyl group |
| c109 | c | Na | S | H | H | vinyl group |
| c110 | c | Na | O | Me | H | methyl group |
| c111 | c | Na | O | Me | H | ethyl group |
| c112 | c | Na | O | Et | H | methyl group |

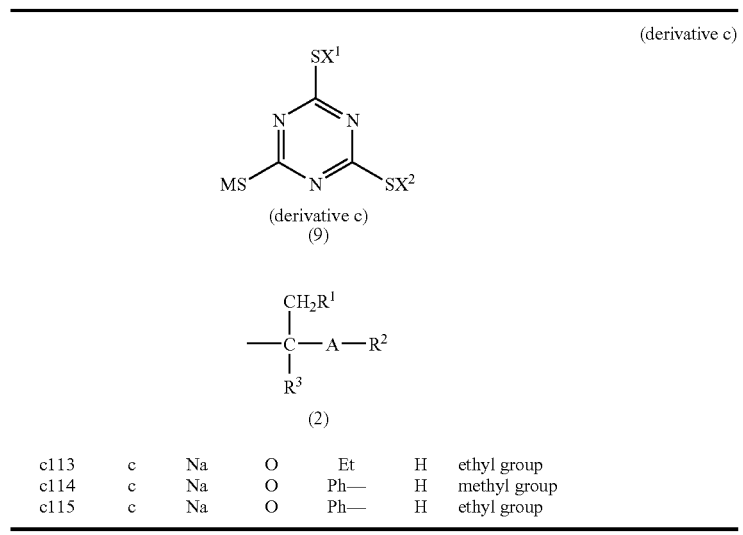

(derivative c)
(9)

| | | | | | | |
|---|---|---|---|---|---|---|
| c113 | c | Na | O | Et | H | ethyl group |
| c114 | c | Na | O | Ph— | H | methyl group |
| c115 | c | Na | O | Ph— | H | ethyl group |

Dithiol Compound Derivative

The thiol compound derivative according to the present invention is, for example, a dithiol compound derivative represented by the following formula (10) (sometimes referred to as "derivative d" hereinafter), which is a derivative of a dithiol compound.

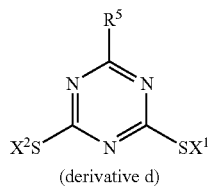

(derivative d)

In the formula (10), $X^1$ and $X^2$ are each a group represented by the following formula (2).

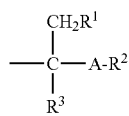

In the formula (10), $X^1$ and $X^2$ are each the same as $X^1$ in the formula (1), and $X^1$ and $X^2$ may be the same or different, preferably the same. The formula (2) is the same as that previously described.

In the formula (10), $R^5$ is a group selected from the following groups (g) to (k).

(g) A group selected from a hydrogen atom, an alkyl group, an alkenyl group, an alkynyl group, a phenyl group, an aralkyl group and —NH$_2$.

Of these, a hydrogen atom, an alkyl group and a phenyl group are preferable.

The alkyl group is preferably an alkyl group of 1 to 25 carbon atoms, more preferably an alkyl group of 1 to 18 carbon atoms. The alkyl group may be any of straight-chain, branched and cyclic alkyl groups. Examples of such alkyl groups include methyl, ethyl, n-propyl, isopropyl, n-butyl, isobutyl, sec-butyl, tert-butyl, pentyl, hexyl, heptyl, octyl, 2-ethylhexyl, decyl, cetyl, stearyl and 1-menthyl. Of these, methyl and ethyl are preferable.

The alkenyl group is preferably an alkenyl group of 1 to 20 carbon atoms, more preferably an alkenyl group of 1 to 10 carbon atoms. Examples of such alkenyl groups include propanedienyl, isopropenyl, 3-methyl-2-butenyl, allyl and 2-methylallyl. Of these, isopropenyl is preferable.

The alkynyl group is preferably an alkynyl group of 1 to 20 carbon atoms, more preferably an alkynyl group of 1 to 10 carbon atoms. Examples of such alkynyl groups include propargyl and 1-phenylpropargyl. Of these, propargyl is preferable.

The aralkyl group is preferably an aralkyl group of 1 to 20 carbon atoms, more preferably an aralkyl group of 1 to 10 carbon atoms. An example of such an aralkyl group is 4-phenylbutyl.

Examples of the phenyl groups include phenyl($C_6H_5$—), methoxyphenyl, o-tolyl, p-nitrophenyl, 2-nitrophenyl, 3-nitrophenyl, p-fluorophenyl, p-methoxyphenyl, p-aminophenyl, N-methylaminophenyl, p-(dimethylamino)phenyl, 4-acetylphenyl, p-iodophenyl, p-chlorophenyl, 2-piperidinoethyl, 2,4,6-trichlorophenyl, 2,4,6-trimethylphenyl, 2,4,6-tribromophenyl, 2,4-dichlorophenyl, 2,4-dibromophenyl and 2,4-dimethylphenyl. Of these, phenyl is preferable.

(h) A dialkylamino group represented by the following formula (11):

$$-NR^6R^7 \qquad (11)$$

wherein $R^6$ and $R^7$ are each a group selected from an alkyl group, an alkenyl group, an alkynyl group, an aralkyl group, a benzyl group, an allyl group, a cycloalkyl group, a fluoroalkyl group and a phenyl group, and $R^6$ and $R^7$ may be the same or different. Of these, an alkyl group and an alkenyl group are preferable.

The alkyl group is preferably an alkyl group of 1 to 25 carbon atoms, more preferably an alkyl group of 1 to 18 carbon atoms. The alkyl group may be any of straight-chain, branched and cyclic alkyl groups. Examples of such alkyl groups include methyl, ethyl, n-propyl, isopropyl, n-butyl, isobutyl, sec-butyl, tert-butyl, pentyl, hexyl, heptyl, octyl, 2-ethylhexyl, decyl, cetyl, stearyl and 1-menthyl. Of these, methyl and ethyl are preferable.

The alkenyl group is preferably an alkenyl group of 1 to 20 carbon atoms, more preferably an alkenyl group of 1 to 10 carbon atoms. Examples of such alkenyl groups include propanedienyl, isopropenyl, 3-methyl-2-butenyl, allyl and 2-methylallyl. Of these, isopropenyl is preferable.

The alkynyl group is preferably an alkynyl group of 1 to 20 carbon atoms, more preferably an alkynyl group of 1 to 10 carbon atoms. Examples of such alkynyl groups include propargyl and 1-phenylpropargyl. Of these, propargyl is preferable.

The aralkyl group is preferably an aralkyl group of 1 to 20 carbon atoms, more preferably an aralkyl group of 1 to 10 carbon atoms. An example of such an aralkyl group is methylbenzyl.

Examples of the benzyl groups include benzyl and 1-phenylethyl.

Examples of the cycloalkyl groups include cyclohexyl and cyclopentyl.

Examples of the fluoroalkyl groups include tetrafluoroethyl.

(i) A monoalkylamino group represented by the following formula (12)

$$-NHR^8 \qquad (12)$$

wherein $R^8$ is a group selected from an alkyl group, an alkenyl group, an alkynyl group, an aralkyl group, a benzyl group, an allyl group, a cycloalkyl group, a fluoroalkyl group, an anilino group, a hydroxyanilino group and a phenyl group. Of these, an alkyl group is preferable.

Examples of the alkyl groups, the alkenyl groups, the alkynyl groups, the aralkyl groups, the benzyl groups, the allyl groups, the cycloalkyl groups and the fluoroalkyl groups include the same groups as previously described with respect to $R^6$ and $R^7$.

Examples of the anilino groups include anilino and p-methylanilino.

Examples of the hydroxyanilino groups include groups derived from o-, m- and p-hydroxyaniline derivatives.

(j) A group represented by the following formula (13):

$$-OR^9 \qquad (13)$$

wherein $R^9$ is a group selected from an alkyl group, a phenyl group, an alkenyl group, an aralkyl group, a halogenophenyl group, a naphthyl group and a cycloalkyl group. Of these, preferable are an alkyl group and a phenyl group.

The alkyl group is preferably an alkyl group of 1 to 25 carbon atoms, more preferably an alkyl group of 1 to 18 carbon atoms. The alkyl group may be any of straight-chain, branched and cyclic alkyl groups. Examples of such alkyl groups include methyl, ethyl, n-propyl, isopropyl, n-butyl, isobutyl, sec-butyl, tert-butyl, pentyl, hexyl, heptyl, octyl, 2-ethylhexyl, decyl, cetyl, stearyl and 1-menthyl. Of these, methyl and ethyl are preferable.

The alkenyl group is preferably an alkenyl group of 1 to 20 carbon atoms, more preferably an alkenyl group of 1 to 10 carbon atoms. Examples of such alkenyl groups include propanedienyl, isopropenyl, 3-methyl-2-butenyl, allyl and 2-methylallyl. Of these, isopropenyl is preferable.

The aralkyl group is preferably an aralkyl group of 1 to 20 carbon atoms, more preferably an aralkyl group of 1 to 10 carbon atoms. An example of such an aralkyl group is 4-phenylbutyl.

Examples of the halogenophenyl groups include p-iodophenyl, p-chlorophenyl, p-bromophenyl, 2,4-dichlorophenyl, 2,4-dibromophenyl, 2,4-diiodophenyl, 2,4,6-trichlorophenyl and 2,4,6-tribromophenyl. Of these, p-chlorophenyl is preferable.

Examples of the cycloalkyl groups include cyclohexyl and cyclopentyl.

(k) A group represented by the following formula (14):

$$-SR^{10} \qquad (14)$$

wherein $R^{10}$ is a group selected from an alkyl group, an alkenyl group, an alkynyl group, a phenyl group, an aralkyl group, a halogenophenyl group, a naphthyl group and a cycloalkyl group. Of these, an alkyl group is preferable.

Examples of the alkyl groups, the alkenyl groups, the aralkyl groups, the halogenphenyl groups, the naphthyl groups and the cycloalkyl groups include those of the alkyl groups, the alkenyl groups, the aralkyl groups, the halogenphenyl groups, the naphthyl groups and the cycloalkyl groups previously described with respect to $R^9$.

The alkynyl group is preferably an alkynyl group of 1 to 20 carbon atoms, more preferably an alkynyl group of 1 to 10 carbon atoms. Examples of such alkynyl groups include propargyl and 1-phenylpropargyl. Of these, propargyl is preferable.

Examples of the phenyl groups include phenyl($C_6H_5-$), methoxyphenyl, o-tolyl, p-nitrophenyl, 2-nitrophenyl, 3-nitrophenyl, p-fluorophenyl, p-methoxyphenyl, p-aminophenyl, N-methylaminophenyl, p-(dimethylamino)phenyl, 4-acetylphenyl, p-iodophenyl, p-chlorophenyl, 2-piperidinoethyl, 2,4,6-trichlorophenyl, 2,4,6-trimethylphenyl, 2,4,6-tribromophenyl, 2,4-dichlorophenyl, 2,4-dibromophenyl and 2,4-dimethylphenyl. Of these, phenyl and methoxyphenyl are preferable.

In the thiol compound derivative of the invention, $R^1$ and $R^2$ in the formula (11) may form a ring. When $R^1$ and $R^2$ form a ring, $R^1$ and $R^2$ are each preferably an alkyl group, and the alkyl group may have a substituent.

In the above case, $R^3$ is preferably a hydrogen atom, and the ring formed from $R^1$ and $R^2$ is preferably represented by the following formula (7):

wherein n is 3 or 4.

The constituent of the above-mentioned cyclic structure may have a substituent.

Another dithiol compound derivative that is the thiol compound derivative according to the present invention is a thiol compound derivative represented by the following formula (15) (sometimes referred to as "derivative e" hereinafter):

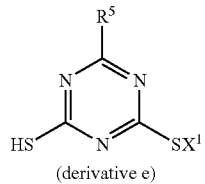

(derivative e)

wherein $X^1$ is a group represented by the following formula (2):

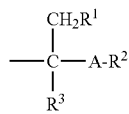

In the formula (15), $R^5$ is the same as $R^5$ in the formula (10). The formula (2) is the same as that previously described.

Another dithiol compound derivative that is the thiol compound derivative according to the present invention is a thiol compound derivative represented by the following formula (16) (sometimes referred to as "derivative f" hereinafter):

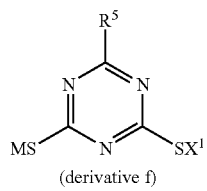

(derivative f)

wherein $X^1$ is a group represented by the following formula (2):

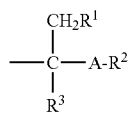

In the formula (16), M is an alkali metal or an alkaline earth metal. Examples of the alkali metals include sodium and potassium. Examples of the alkaline earth metals include calcium, magnesium and barium. Of these, sodium is preferable.

$R^5$ is the same as $R^5$ in the formula (10). The formula (2) is the same as that previously described.

Described below are examples of "preferred substituents $R^5$" in the thiol compound derivative represented by the formula (10):

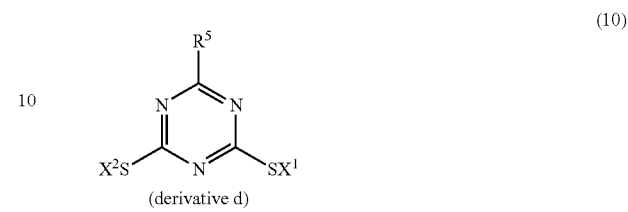

(derivative d)

wherein $X^1$ and $X^2$ are each a group represented by the following formula (2):

That is to say, there can be mentioned a hydrogen atom, a methyl group, a phenyl group, an amino group, a dihexylamino group, a bis(2-hexyl)amino group, a diethylamino group, a dicyclohexylamino group, a diphenylamino group, a dibenzylamino group, a diallylamino group, a didodecylamino group, a dibutylamino group, a dimethylamino group, a phenylamino group, a 3,5-di-tert-butyl-4-hydroxyanilino group, a stearylamino group, an ethylamino group, a hexylamino group, a cis-9-octadecenylamino group, a cyclohexylamino group, a 4-anilino-N-isopropylanilino group, a methoxy group, a 1-naphthyloxy group, a m-chlorophenoxy group, a 2,4-dimethylphenoxy group and a phenoxy group. Examples of "more preferred substituents $R^5$" include a hydrogen atom, a methyl group, a phenyl group, a dibutylamino group, a methoxy group and a phenoxy group.

Examples of preferred substituents $R^5$ and more preferred substituents $R^5$ in the derivative e represented by the formula (15) and the derivative f represented by the formula (16) are the same as those described above with respect to the thiol compound derivative d represented by the formula (10).

Particularly preferable is a thiol compound derivative wherein $R^5$ is any one of (g) to (k) and in the formula (2) A is an oxygen atom, $R^1$ is a hydrogen atom, $R^2$ is an alkyl group or a residue wherein a hydroxyl group is removed from (poly) alkylene glycol, and $R^3$ is a hydrogen atom.

Examples of the thiol compound derivatives d, e and f represented by the formulas (10), (15) and (16), respectively, include thiol compound derivatives d, e and f having, as A, $R^1$, $R^2$ and $R^3$ of $X^1$, substituents shown in the following Table 4 (Tables 4-1 to 4-4), Table 5 (Table 5-1 to 5-4) and Table 6 (Table 6-1 to 6-4).

Tables 4-1

| Thiol compound derivative | Derivative | A | $R^3$ | $R^1$ | $R^2$ |
|---|---|---|---|---|---|
| d1 | d | O | H | H | methyl group |
| d2 | d | O | H | H | ethyl group |

-continued

| | | | | | |
|---|---|---|---|---|---|
| d3  | d | O | H | H | n-propyl group |
| d4  | d | O | H | H | isopropyl group |
| d5  | d | O | H | H | n-butyl group |
| d6  | d | O | H | H | isobutyl group |
| d7  | d | O | H | H | sec-butyl group |
| d8  | d | O | H | H | tert-butyl group |
| d9  | d | O | H | H | pentyl group |
| d10 | d | O | H | H | hexyl group |
| d11 | d | O | H | H | heptyl group |
| d12 | d | O | H | H | octyl group |
| d13 | d | O | H | H | 2-ethylhexyl group |
| d14 | d | O | H | H | decyl group |
| d15 | d | O | H | H | cetyl group |
| d16 | d | O | H | H | stearyl group |
| d17 | d | O | H | H | 1-menthyl group |
| d18 | d | O | H | H | propanedienyl group |
| d19 | d | O | H | H | isopropenyl group |
| d20 | d | O | H | H | 3-butynyl group |
| d21 | d | O | H | H | 3-methyl-2-butenyl group |
| d22 | d | O | H | H | allyl group |
| d23 | d | O | H | H | 2-methylallyl group |
| d24 | d | O | H | H | propargyl group |
| d25 | d | O | H | H | 3-phenylpropargyl group |
| d26 | d | O | H | H | residue wherein one hydroxyl group of ethylene glycol is removed |
| d27 | d | O | H | H | residue wherein one hydroxyl group of propylene glycol is removed |
| d28 | d | O | H | H | residue wherein one hydroxyl group of butylene glycol is removed |
| d29 | d | O | H | H | residue wherein one hydroxyl group of diethylene glycol is removed |
| d30 | d | O | H | H | residue wherein one hydroxyl group of dipropylene glycol is removed |
| d31 | d | O | H | H | residue wherein one hydroxyl group of dibutylene glycol is removed |
| d32 | d | O | H | H | residue wherein one hydroxyl group of diethylene glycol monobutyl ether is removed |
| d33 | d | O | H | H | residue wherein one hydroxyl group of triethylene glycol is removed |
| d34 | d | O | H | H | residue wherein one hydroxyl group of tripropylene glycol is removed |
| d35 | d | O | H | H | residue wherein one hydroxyl group of tributylene glycol is removed |

Tables 4-2

| Thiol compound derivative | Derivative | A | $R^3$ | $R^1$ | $R^2$ |
|---|---|---|---|---|---|
| d36 | d | O | H | H | residue wherein one hydroxyl group of tetraethylene glycol is removed |
| d37 | d | O | H | H | residue wherein one hydroxyl group of tetrapropylene glycol is removed |
| d38 | d | O | H | H | residue wherein one hydroxyl group of tetrabutylene glycol is removed |
| d39 | d | O | H | H | residue wherein a hydroxyl group of acetone oxime group is removed |
| d40 | d | O | H | H | residue wherein one hydroxyl group of triethanolamine is removed |
| d41 | d | O | H | H | residue wherein one hydroxyl group of diethanolamine is removed |
| d42 | d | O | H | H | residue wherein a hydroxyl group of dimethylaminoethanol is removed |
| d43 | d | O | H | H | residue wherein a hydroxyl group of trimethylsilyl alcohol is removed |
| d44 | d | O | H | H | residue wherein a hydroxyl group of triethylsilyl alcohol is removed |
| d45 | d | O | H | H | residue wherein a hydroxyl group of cyclohexyl alcohol is removed |
| d46 | d | O | H | H | residue wherein a hydroxyl group of menthol is removed |
| d47 | d | O | H | H | residue wherein a hydroxyl group of naphthyl alcohol is removed |
| d48 | d | O | H | H | 1-chloroethyl group |
| d49 | d | O | H | H | 2-chloroethyl group |
| d50 | d | O | H | H | 1-bromoethyl group |
| d51 | d | O | H | H | 2-bromoethyl group |
| d52 | d | O | H | H | methoxyethyl group |

-continued

| | | | | | |
|---|---|---|---|---|---|
| d53 | d | O | H | H | 2-butoxyethyl group |
| d54 | d | O | H | H | methoxyethoxyethyl group |
| d55 | d | O | H | H | dimethylaminoethyl group |
| d56 | d | O | H | H | 2-(diethylamino)ethyl group |
| d56 | d | O | H | H | 3-dimethylaminopropyl group |
| d57 | d | O | H | H | aminoethyl group |
| d58 | d | O | H | H | trimethylsilylethyl group |
| d59 | d | O | H | H | trimethylsiloxyethyl group |
| d60 | d | O | H | H | 2-acetoxyethyl group |
| d61 | d | O | H | H | 2-piperidinoethyl group |
| d62 | d | O | H | H | phenyl group |
| d63 | d | O | H | H | methoxyphenyl group |
| d64 | d | O | H | H | o-tolyl group |
| d65 | d | O | H | H | o-isopropylphenyl group |
| d66 | d | O | H | H | p-nitrophenyl group |
| d67 | d | O | H | H | 2-nitrophenyl group |
| d68 | d | O | H | H | 3-nitrophenyl group |
| d69 | d | O | H | H | p-fluorophenyl group |
| d70 | d | O | H | H | p-methoxyphenyl group |

Tables 4-3

| Thiol compound derivative | Derivative | A | $R^3$ | $R^1$ | $R^2$ |
|---|---|---|---|---|---|
| d71 | d | O | H | H | p-aminophenyl group |
| d72 | d | O | H | H | N-methylaminophenyl group |
| d73 | d | O | H | H | p-(dimethylamino)phenyl group |
| d74 | d | O | H | H | 4-acetylphenyl group |
| d75 | d | O | H | H | p-iodophenyl group |
| d76 | d | O | H | H | p-chlorophenyl group |
| d77 | d | O | H | H | p-bromophenyl group |
| d78 | d | O | H | H | 2,4,6-trichlorophenyl group |
| d79 | d | O | H | H | 2,4,6-tribromophenyl group |
| d80 | d | O | H | H | 2,4,6-trimethylphenyl group |
| d81 | d | O | H | H | 2,4-dichlorophenyl group |
| d82 | d | O | H | H | 2,4-dibromophenyl group |
| d83 | d | O | H | H | 2,4-dimethylphenyl group |
| d84 | d | O | H | H | —CH$_2$OCH=CH$_2$ |
| d85 | d | O | H | H | —CH$_2$CH$_2$OCH=CH$_2$ |
| d86 | d | O | H | H | —CH$_2$CH$_2$CH$_2$OCH=CH$_2$ |
| d87 | d | O | H | H | —CH$_2$CH$_2$CH$_2$CH$_2$OCH=CH$_2$ |
| d88 | d | O | H | H | —CH$_2$CH$_2$OCH$_2$CH$_2$OCH=CH$_2$ |
| d89 | d | O | H | H | —CH$_2$CH$_2$OCH$_2$CH$_2$OCH$_2$CH=CH$_2$ |
| d90 | d | O | H | H | —CH$_2$CH$_2$N(CH$_2$CH$_2$OH)CH$_2$CH$_2$OCH=CH$_2$ |
| d91 | d | O | H | H | —Ph—OCH=CH$_2$ |
| d92 | d | O | H | H | —Ph—N=N—Ph—OCH=CH$_2$ |
| d93 | d | O | H | H | —Ph—C(CH$_3$)$_2$—Ph—OCH=CH$_2$ |
| d94 | d | O | H | H | -cyclohexylene-OCH=CH$_2$ |
| d95 | d | O | H | H | 1-phenylethyl group |
| d96 | d | O | H | H | benzyl group |
| d97 | d | | | | 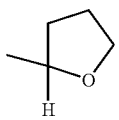 |
| d98 | d | | | | 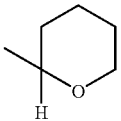 |

Tables 4-4

| Thiol compound derivative | Derivative | A | $R^3$ | $R^1$ | $R^2$ |
|---|---|---|---|---|---|
| d99 | d | | | | 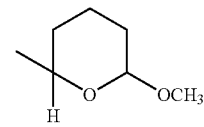 |

-continued

| | | | | | |
|---|---|---|---|---|---|
| d100 | d | | | | (structure: 4,4,6-trimethyl-tetrahydropyran-2-one) |
| d101 | d | | | | (structure: 2-ethoxy-6-methyl-tetrahydropyran) |
| d102 | d | S | H | H | 3-(trimethylsilyl)propyl group |
| d103 | d | S | H | H | 2-hydroxyethyl group |
| d104 | d | S | H | H | 2-(N-morpholino)ethyl group |
| d105 | d | S | H | H | 2-(N-β-hydroxyethyl)aminoethyl group |
| d106 | d | S | H | H | 2-aminoethyl group |
| d107 | d | S | H | H | p-chlorophenyl group |
| d108 | d | S | H | H | phenyl group |
| d109 | d | S | H | H | vinyl group |
| d110 | d | O | Me | H | methyl group |
| d111 | d | O | Me | H | ethyl group |
| d112 | d | O | Et | H | methyl group |
| d113 | d | O | Et | H | ethyl group |
| d114 | d | O | Ph- | H | methyl group |
| d115 | d | O | Ph- | H | ethyl group |

Tables 5-1

| Thiol compound derivative | Derivative | A | $R^3$ | $R^1$ | $R^2$ |
|---|---|---|---|---|---|
| e1 | e | O | H | H | methyl group |
| e2 | e | O | H | H | ethyl group |
| e3 | e | O | H | H | n-propyl group |
| e4 | e | O | H | H | isopropyl group |
| e5 | e | O | H | H | n-butyl group |
| e6 | e | O | H | H | isobutyl group |
| e7 | e | O | H | H | sec-butyl group |
| e8 | e | O | H | H | tert-butyl group |
| e9 | e | O | H | H | pentyl group |
| e10 | e | O | H | H | hexyl group |
| e11 | e | O | H | H | heptyl group |
| e12 | e | O | H | H | octyl group |
| e13 | e | O | H | H | 2-ethylhexyl group |
| e14 | e | O | H | H | decyl group |
| e15 | e | O | H | H | cetyl group |
| e16 | e | O | H | H | stearyl group |
| e17 | e | O | H | H | 1-methyl group |
| e18 | e | O | H | H | propanedienyl group |
| e19 | e | O | H | H | isopropenyl group |
| e20 | e | O | H | H | 3-butynyl group |
| e21 | e | O | H | H | 3-methyl-2-butenyl group |
| e22 | e | O | H | H | allyl group |
| e23 | e | O | H | H | 2-methylallyl group |
| e24 | e | O | H | H | propargyl group |
| e25 | e | O | H | H | 3-phenylpropargyl group |
| e26 | e | O | H | H | residue wherein one hydroxyl group of ethylene glycol is removed |
| e27 | e | O | H | H | residue wherein one hydroxyl group of propylene glycol is removed |
| e28 | e | O | H | H | residue wherein one hydroxyl group of butylene glycol is removed |
| e29 | e | O | H | H | residue wherein one hydroxyl group of diethylene glycol is removed |
| e30 | e | O | H | H | residue wherein one hydroxyl group of dipropylene glycol is removed |
| e31 | e | O | H | H | residue wherein one hydroxyl group of dibutylene glycol is removed |
| e32 | e | O | H | H | residue wherein one hydroxyl group of diethylene glycol monobutyl ether is removed |
| e33 | e | O | H | H | residue wherein one hydroxyl group of triethylene glycol is removed |

-continued

| Thiol compound derivative | Derivative | A | R³ | R¹ | R² |
|---|---|---|---|---|---|
| e34 | e | O | H | H | residue wherein one hydroxyl group of tripropylene glycol is removed |
| e35 | e | O | H | H | residue wherein one hydroxyl group of tributylene glycol is removed |

Tables 5-2

| Thiol compound derivative | Derivative | A | R³ | R¹ | R² |
|---|---|---|---|---|---|
| e36 | e | O | H | H | residue wherein one hydroxyl group of tetraethylene glycol is removed |
| e37 | e | O | H | H | residue wherein one hydroxyl group of tetrapropylene glycol is removed |
| e38 | e | O | H | H | residue wherein one hydroxyl group of tetrabutylene glycol is removed |
| e39 | e | O | H | H | residue wherein a hydroxyl group of acetone oxime group is removed |
| e40 | e | O | H | H | residue wherein one hydroxyl group of triethanolamine is removed |
| e41 | e | O | H | H | residue wherein one hydroxyl group of diethanolamine is removed |
| e42 | e | O | H | H | residue wherein a hydroxyl group of dimethylaminoethanol is removed |
| e43 | e | O | H | H | residue wherein a hydroxyl group of trimethylsilyl alcohol is removed |
| e44 | e | O | H | H | residue wherein a hydroxyl group of triethylsilyl alcohol is removed |
| e45 | e | O | H | H | residue wherein a hydroxyl group of cyclohexyl alcohol is removed |
| e46 | e | O | H | H | residue wherein a hydroxyl group of menthol is removed |
| e47 | e | O | H | H | residue wherein a hydroxyl group of naphthyl alcohol is removed |
| e48 | e | O | H | H | 1-chloroethyl group |
| e49 | e | O | H | H | 2-chloroethyl group |
| e50 | e | O | H | H | 1-bromoethyl group |
| e51 | e | O | H | H | 2-bromoethyl group |
| e52 | e | O | H | H | methoxyethyl group |
| e53 | e | O | H | H | 2-butoxyethyl group |
| e54 | e | O | H | H | methoxyethoxyethyl group |
| e55 | e | O | H | H | dimethylaminoethyl group |
| e56 | e | O | H | H | 2-(diethylamino)ethyl group |
| e56 | e | O | H | H | 3-dimethylaminopropyl group |
| e57 | e | O | H | H | aminoethyl group |
| e58 | e | O | H | H | trimethylsilylethyl group |
| e59 | e | O | H | H | trimethylsiloxyethyl group |
| e60 | e | O | H | H | 2-acetoxyethyl group |
| e61 | e | O | H | H | 2-piperidinoethyl group |
| e62 | e | O | H | H | phenyl group |
| e63 | e | O | H | H | methoxyphenyl group |
| e64 | e | O | H | H | o-tolyl group |
| e65 | e | O | H | H | o-isopropylphenyl group |
| e66 | e | O | H | H | p-nitrophenyl group |
| e67 | e | O | H | H | 2-nitrophenyl group |
| e68 | e | O | H | H | 3-nitrophenyl group |
| e69 | e | O | H | H | p-fluorophenyl group |
| e70 | e | O | H | H | p-methoxyphenyl group |
| e71 | e | O | H | H | p-aminophenyl group |
| e72 | e | O | H | H | N-methylaminophenyl group |

Tables 5-3

| Thiol compound derivative | Derivative | A | R³ | R¹ | R² |
|---|---|---|---|---|---|
| e73 | e | O | H | H | p-(dimethylamino)phenyl group |
| e74 | e | O | H | H | 4-acetylphenyl group |
| e75 | e | O | H | H | p-iodophenyl group |
| e76 | e | O | H | H | p-chlorophenyl group |
| e77 | e | O | H | H | p-bromophenyl group |
| e78 | e | O | H | H | 2,4,6-trichlorophenyl group |
| e79 | e | O | H | H | 2,4,6-tribromophenyl group |
| e80 | e | O | H | H | 2,4,6-trimethylphenyl group |
| e81 | e | O | H | H | 2,4-dichlorophenyl group |
| e82 | e | O | H | H | 2,4-dibromophenyl group |
| e83 | e | O | H | H | 2,4-dimethylphenyl group |
| e84 | e | O | H | H | —CH$_2$OCH=CH$_2$ |

| | | | | | |
|---|---|---|---|---|---|
| e85 | e | O | H | H | —CH$_2$CH$_2$OCH=CH$_2$ |
| e86 | e | O | H | H | —CH$_2$CH$_2$CH$_2$OCH=CH$_2$ |
| e87 | e | O | H | H | —CH$_2$CH$_2$CH$_2$CH$_2$OCH=CH$_2$ |
| e88 | e | O | H | H | —CH$_2$CH$_2$CH$_2$CH$_2$OCH=CH$_2$ |
| e89 | e | O | H | H | —CH$_2$CH$_2$OCH$_2$CH$_2$OCH$_2$CH$_2$OCH=CH$_2$ |
| e90 | e | O | H | H | —CH$_2$CH$_2$N(CH$_2$CH$_2$OH)CH$_2$CH$_2$OCH=CH$_2$ |
| e91 | e | O | H | H | —Ph—OCH=CH$_2$ |
| e92 | e | O | H | H | —Ph—N=N—Ph—OCH=CH$_2$ |
| e93 | e | O | H | H | —Ph—C(CH$_3$)$_2$—Ph—OCH=CH$_2$ |
| e94 | e | O | H | H | -cyclohexylene-OCH=CH$_2$ |
| e95 | e | O | H | H | 1-phenylethyl group |
| e96 | e | O | H | H | benzyl group |
| e97 | e | | | | [structure: 2-methyltetrahydrofuran] |
| e98 | e | | | | [structure: 2-methyltetrahydropyran] |
| e99 | a | | | | [structure: 2-methyl-6-methoxytetrahydropyran] |

Tables 5-4

| Thiol compound derivative | Derivative | A | R$^3$ | R$^1$ | R$^2$ |
|---|---|---|---|---|---|
| e100 | e | | | | [structure: 4,4-dimethyl-6-methyltetrahydropyran-2-one] |
| e101 | e | | | | [structure: 2-methyl-6-ethoxytetrahydropyran] |
| e102 | e | S | H | H | 3-(trimethylsilyl)propyl group |
| e103 | e | S | H | H | 2-hydroxyethyl group |
| e104 | e | S | H | H | 2-(N-morpholino)ethyl group |
| e105 | e | S | H | H | 2-(N-β-hydroxyethyl)aminoethyl group |
| e106 | e | S | H | H | 2-aminoethyl group |
| e107 | e | S | H | H | p-chlorophenyl group |
| e108 | e | S | H | H | phenyl group |
| e109 | e | S | H | H | vinyl group |
| e110 | e | O | Me | H | methyl group |
| e111 | e | O | Me | H | ethyl group |
| e112 | e | O | Et | H | methyl group |
| e113 | e | O | Et | H | ethyl group |
| e114 | e | O | Ph— | H | methyl group |
| e115 | e | O | Ph— | H | ethyl group |

Tables 6-1

| Thiol compound derivative | Derivative | A | R$^3$ | R$^1$ | R$^2$ |
|---|---|---|---|---|---|
| f1 | f | Na | O | H | H methylgroup |
| f2 | f | Na | O | H | H ethylgroup |
| f3 | f | Na | O | H | H n-propyl group |
| f4 | f | Na | O | H | H isopropyl group |

-continued

| Thiol compound derivative | Derivative | A | R³ | R¹ | R² | |
|---|---|---|---|---|---|---|
| f5 | f | Na | O | H | H | n-butyl group |
| f6 | f | Na | O | H | H | isobutyl group |
| f7 | f | Na | O | H | H | sec-butyl group |
| f8 | f | Na | O | H | H | tert-butyl group |
| f9 | f | Na | O | H | H | pentyl group |
| f10 | f | Na | O | H | H | hexyl group |
| f11 | f | Na | O | H | H | heptyl group |
| f12 | f | Na | O | H | H | octyl group |
| f13 | f | Na | O | H | H | 2-ethylhexyl group |
| f14 | f | Na | O | H | H | decyl group |
| f15 | f | Na | O | H | H | cetyl group |
| f16 | f | Na | O | H | H | stearyl group |
| f17 | f | Na | O | H | H | 1-methyl group |
| f18 | f | Na | O | H | H | propanedienyl group |
| f19 | f | Na | O | H | H | isopropenyl group |
| f20 | f | Na | O | H | H | 3-butynyl group |
| f21 | f | Na | O | H | H | 3-methyl-2-butenyl group |
| f22 | f | Na | O | H | H | allyl group |
| f23 | f | Na | O | H | H | 2-methylallyl group |
| f24 | f | Na | O | H | H | propargyl group |
| f25 | f | Na | O | H | H | 3-phenylpropargyl group |
| f26 | f | Na | O | H | H | residue wherein one hydroxyl group of ethylene glycol is removed |
| f27 | f | Na | O | H | H | residue wherein one hydroxyl group of propylene glycol is removed |
| f28 | f | Na | O | H | H | residue wherein one hydroxyl group of butylene glycol is removed |
| f29 | f | Na | O | H | H | residue wherein one hydroxyl group of diethylene glycol is removed |
| f30 | f | Na | O | H | H | residue wherein one hydroxyl group of dipropylene glycol is removed |
| f31 | f | Na | O | H | H | residue wherein one hydroxyl group of dibutylene glycol is removed |
| f32 | f | Na | O | H | H | residue wherein one hydroxyl group of diethylene glycol monobutyl ether is removed |

Tables 6-2

| Thiol compound derivative | Derivative | A | R³ | R¹ | R² | |
|---|---|---|---|---|---|---|
| f33 | f | Na | O | H | H | residue wherein one hydroxyl group of triethylene glycol is removed |
| f34 | f | Na | O | H | H | residue wherein one hydroxyl group of tripropylene glycol is removed |
| f35 | f | Na | O | H | H | residue wherein one hydroxyl group of tributylene glycol is removed |
| f36 | f | Na | O | H | H | residue wherein one hydroxyl group of tetraethylene glycol is removed |
| f37 | f | Na | O | H | H | residue wherein one hydroxyl group of tetrapropylene glycol is remove |
| f38 | f | Na | O | H | H | residue wherein one hydroxyl group of tetrabutylene glycol is remove |
| f39 | f | Na | O | H | H | residue wherein a hydroxyl group of acetone oxime group is removed |
| f40 | f | Na | O | H | H | residue wherein one hydroxyl group of triethanolamine is removed |
| f41 | f | Na | O | H | H | residue wherein one hydroxyl group of diethanolamine is removed |
| f42 | f | Na | O | H | H | residue wherein a hydroxyl group of dimethylaminoethanol is removed |
| f43 | f | Na | O | H | H | residue wherein a hydroxyl group of trimethylsilyl alcohol is removed |
| f44 | f | Na | O | H | H | residue wherein a hydroxyl group of triethylsilyl alcohol is removed |
| f45 | f | Na | O | H | H | residue wherein a hydroxyl group of cyclohexyl alcohol is removed |
| f46 | f | Na | O | H | H | residue wherein a hydroxyl group of menthol is removed |
| f47 | f | Na | O | H | H | residue wherein a hydroxyl group of naphthyl alcohol is removed |
| f48 | f | Na | O | H | H | 1-chloroethyl group |
| f49 | f | Na | O | H | H | 2-chloroethyl group |
| f50 | f | Na | O | H | H | 1-bromoethyl group |
| f51 | f | Na | O | H | H | 2-bromoethyl group |
| f52 | f | Na | O | H | H | methoxyethyl group |
| f53 | f | Na | O | H | H | 2-butoxyethyl group |
| f54 | f | Na | O | H | H | methoxyethoxyethyl group |

-continued

| Thiol compound derivative | Derivative | A | R³ | R¹ | R² |
|---|---|---|---|---|---|
| f55 | f | Na | O | H | H | dimethylaminoethyl group |
| f56 | f | Na | O | H | H | 2-(diethylamino)ethyl group |
| f56 | f | Na | O | H | H | 3-dimethylaminopropyl group |
| f57 | f | Na | O | H | H | aminoethyl group |
| f58 | f | Na | O | H | H | trimethylsilylethyl group |
| f59 | f | Na | O | H | H | trimethylsiloxyethyl group |

Tables 6-3

| Thiol compound derivative | Derivative | A | R³ | R¹ | R² |
|---|---|---|---|---|---|
| f60 | f | Na | O | H | H | 2-acetoxyethyl group |
| f61 | f | Na | O | H | H | 2-piperidinoethyl group |
| f62 | f | Na | O | H | H | phenyl group |
| f63 | f | Na | O | H | H | methoxyphenyl group |
| f64 | f | Na | O | H | H | o-tolyl group |
| f65 | f | Na | O | H | H | o-isopropylphenyl group |
| f66 | f | Na | O | H | H | p-nitrophenyl group |
| f67 | f | Na | O | H | H | 2-nitrophenyl group |
| f68 | f | Na | O | H | H | 3-nitrophenyl group |
| f69 | f | Na | O | H | H | p-fluorophenyl group |
| f70 | f | Na | O | H | H | p-methoxyphenyl group |
| f71 | f | Na | O | H | H | p-aminophenyl group |
| f72 | f | Na | O | H | H | N-methylaminophenyl group |
| f73 | f | Na | O | H | H | p-(dimethylamino)phenyl group |
| f74 | f | Na | O | H | H | 4-acetylphenyl group |
| f75 | f | Na | O | H | H | p-iodophenyl group |
| f76 | f | Na | O | H | H | p-chlorophenyl group |
| f77 | f | Na | O | H | H | p-bromophenyl group |
| f78 | f | Na | O | H | H | 2,4,6-trichlorophenyl group |
| f79 | f | Na | O | H | H | 2,4,6-tribromophenyl group |
| f80 | f | Na | O | H | H | 2,4,6-trimethylphenyl group |
| f81 | f | Na | O | H | H | 2,4-dichlorophenyl group |
| f82 | f | Na | O | H | H | 2,4-dibromophenyl group |
| f83 | f | Na | O | H | H | 2,4-dimethylphenyl group |
| f84 | f | Na | O | H | H | —CH$_2$OCH=CH$_2$ |
| f85 | f | Na | O | H | H | —CH$_2$CH$_2$OCH=CH$_2$ |
| f86 | F | Na | O | H | H | —CH$_2$CH$_2$CH$_2$OCH=CH$_2$ |
| f87 | F | Na | O | H | H | —CH$_2$CH$_2$CH$_2$CH$_2$OCH=CH$_2$ |
| f88 | F | Na | O | H | H | —CH$_2$CH$_2$OCH$_2$CH$_2$OCH=CH$_2$ |
| f89 | f | Na | O | H | H | —CH$_2$CH$_2$OCH$_2$CH$_2$OCH$_2$CH$_2$OCH=CH$_2$ |
| f90 | f | Na | O | H | H | —CH$_2$CH$_2$N(CH$_2$CH$_2$OH)CH$_2$CH$_2$OCH=CH$_2$ |
| f91 | f | Na | O | H | H | —Ph—OCH=CH$_2$ |
| f92 | f | Na | O | H | H | —Ph—N=N—Ph—OCH=CH$_2$ |
| f93 | F | Na | O | H | H | —Ph—C(CH$_3$)$_2$—Ph—OCH=CH$_2$ |
| f94 | F | Na | O | H | H | -cyclohexylene-OCH=CH$_2$ |
| f95 | F | Na | O | H | H | 1-phenylethyl group |
| f96 | f | Na | O | H | H | benzyl group |

Tables 6-4

| Thiol compound derivative | Derivative | A | R³ | R¹ | R² |
|---|---|---|---|---|---|
| f97 | f | Na | 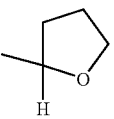 |
| f98 | f | Na | 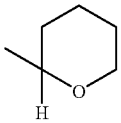 |
| f99 | f | Na | 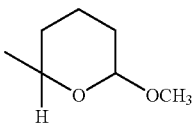 |

-continued

| | | | | | | |
|---|---|---|---|---|---|---|
| f100 | f | Na | | | | (structure: 6-methyl-4,4-dimethyl tetrahydropyran-2-one) |
| f101 | f | Na | | | | (structure: 6-methyl-2-ethoxy tetrahydropyran) |
| f102 | f | Na | S | H | H | 3-(trimethylsilyl)propyl group |
| f103 | f | Na | S | H | H | 2-hydroxyethyl group |
| f104 | f | Na | S | H | H | 2-(N-morpholino)ethyl group |
| f105 | f | Na | s | H | H | 2-(N-β-hydroxyethyl)aminoethyl group |
| f106 | f | Na | S | H | H | 2-aminoethyl group |
| f107 | f | Na | S | H | H | p-chlorophenyl group |
| f108 | f | Na | S | H | H | phenyl group |
| f109 | f | Na | S | H | H | vinyl group |
| f110 | f | Na | O | Me | H | methyl group |
| f111 | f | Na | O | Me | H | ethyl group |
| f112 | f | Na | O | Et | H | methyl group |
| f113 | f | Na | O | Et | H | ethyl group |
| f114 | f | Na | O | Ph— | H | methyl group |
| f115 | f | Na | O | Ph— | H | ethyl group |

As the thiol compound derivative of the invention, a monothiol compound derivative wherein one of the substituents —$SX^1$ and —$SX^2$ of the dithiol compound derivative represented by the formula (10) is further substituted with —$R^5$ is also available in addition to the trithiol compound derivative and the dithiol compound derivative. In the monothiol compound derivative, $R^5$ and $X^1$ (or $X^2$) are the same of $R^5$ and $X^1$ of the dithiol compound derivative represented by the formula (10).

Process for Preparing Thiol Compound Derivative

The thiol compound derivative of the invention is obtained by bonding a part or all of thiol groups (—SH) of a thiol compound having 1 to 3 thiol groups in one molecule to a double bond part of a vinyl ether or the like. In other words, the thiol compound derivative can be obtained by replacing a hydrogen atom of a thiol group of a thiol compound with a substituent derived from a vinyl ether or the like.

There is no specific limitation on the process for preparing the thiol compound derivative, and publicly known processes capable of forming a desired substituent are employable.

For example, a thiol compound, such as triazinethiol or triazinedithiol, and monovinyl ether, aldehyde, ketone or the like are contacted in given amounts, whereby the thiol compound derivative wherein given amounts of thiol groups (—SH group) are substituted can be obtained.

The thiol compound derivative can also be obtained from a thiol compound and a polyvalent vinyl ether compound. In this case, a crosslinked product of the thiol compound is sometimes formed by virtue of the polyvalent vinyl ether.

In the contact of the thiol compound with the vinyl ether or the like, an acid catalyst can be used when needed.

Examples of the thiol compound derivatives thus obtained include derivatives wherein the thiol group and the vinyl group of the vinyl ethers are reacted in the same amounts and all of hydrogen atoms of the thiol groups are replaced with substituents derived from the vinyl ethers, derivatives wherein one thiol group remains, and derivatives wherein a salt is formed from the remaining thiol group with the aid of an alkali metal, a polyvalent metal or an onium base such as quaternary ammonium base, phosphonium base or pyridinium base.

Next, the thiol compound, the vinyl ethers, etc. are described. In addition, the catalyst that is optionally used for the reaction of the thiol compound with the vinyl ether or the like and the process for preparing the thiol compound derivative are also described in detail.

Thiol Compound

The thiol compound for use in the invention is preferably a compound wherein two or more thiol groups per molecule are bonded, and any of such thiol compounds is employable.

Examples of the thiol compounds include phenylthiol such as dimercaptobenzene, thiocarboxylic acids, thiol compounds such as thiadiazole, mercaptoalkyltrialkoxysilanes such as γ-mercaptopropyltrimethoxysilane, aliphatic dithiols such as 1,10-dimercaptodecane, 1,3,5-triazine-2,4,6-trithiol represented by the following formula (18), and triazinethiols represented by the following formula (19).

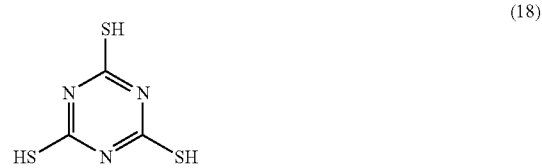

(18)

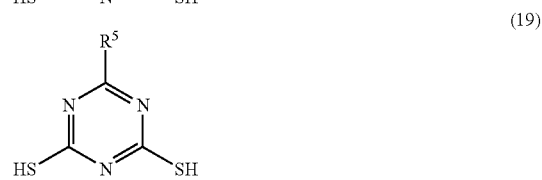

(19)

In addition to the trithiol compounds and the dithiol compounds, monothiol compounds wherein one of the thiol groups (—SH) in the above formula (19) is further substituted with $R^5$ are also employable.

$R^5$ in the formula (19) is the same as $R^5$ in the aforesaid formula (10).

Preferred examples of the dithiol compounds represented by the formula (19) include:
s-triazine-2,4-dithiol,
6-methyl-s-triazine-2,4-dithiol,
6-phenyl-s-triazine-2,4-dithiol,
6-amino-s-triazine-2,4-dithiol,
6-dihexylamino-s-triazine-2,4-dithiol,
6-[bis(2-hexyl)amino]-s-triazine-2,4-dithiol,
6-diethylamino-s-triazine-2,4-dithiol,
6-dicyclohexylamino-s-triazine-2,4-dithiol,
6-diphenylamino-s-triazine-2,4-dithiol,
6-dibenzylamino-s-triazine-2,4-dithiol,
6-diallylamino-s-triazine-2,4-dithiol,
6-didodecylamino-s-triazine-2,4-dithiol,
6-dibutylamino-s-triazine-2,4-dithiol,
6-dimethylamino-s-triazine-2,4-dithiol,
6-phenylamino-s-triazine-2,4-dithiol,
2-(3,5-di-tert-butyl-4-hydroxyanilino)-s-triazine-2,4-dithiol,
6-stearylamino-s-triazine-2,4-dithiol,
6-ethylamino-s-triazine-2,4-dithiol,
6-hexylamino-s-triazine-2,4-dithiol,
6-(cis-9-octadecenylamino)-s-triazine-2,4-dithiol,
6-cyclohexylamino-s-triazine-2,4-dithiol,
6-(4-anilino-N-isopropylanilino)-s-triazine-2,4-dithiol,
6-methoxy-s-triazine-2,4-dithiol,
6-(1-naphthyloxy)-s-triazine-2,4-dithiol,
6-(m-chlorophenoxy)-s-triazine-2,4-dithiol,
6-(2,44-dimethylphenoxy)-s-triazine-2,4-dithiol, and
6-phenoxy-s-triazine-2,4-dithiol.

Of these, 6-phenyl-2-triazine-2,4-dithiol is preferable.

Vinyl Ethers, etc.

Of the vinyl ethers, the aldehydes and the ketones employable for the preparation of the thiol compound derivatives of the invention, vinyl ethers are preferably employed from the viewpoint of reactivity. The vinyl ethers have only to contain at least one vinyl group per molecule, and monovinyl ethers, monovinyl thioethers and pyran derivatives or furan derivatives which are cyclic vinyl ethers are available. Also available are polyvalent vinyl ethers, such as divinyl ethers, trivinyl ethers and tetravinyl ethers.

Of these, preferable are monovinyl ethers, monovinyl thioethers and pyran derivatives or furan derivatives which are cyclic vinyl ethers.

The vinyl ether is, for example, a vinyl ether or a vinyl thioether represented by the following formula (20):

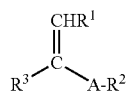
(20)

wherein $R^1$, $R^2$, $R^3$ and A are the same as $R^1$, $R^2$, $R^3$ and A in the aforesaid formula (2), and $R^1$ and $R^2$ may form a ring.

For the preparation of the thiol compound derivative of the invention, $R^1$ and $R^2$ in the formula (20) may form a ring. When $R^1$ and $R^2$ form a ring, $R^1$ and $R^2$ are each preferably an alkyl group, and the alkyl group may have a substituent. In this case, $R^3$ is preferably a hydrogen atom.

Examples of such vinyl ethers include the following compounds:
methyl-1-phenyl vinyl ether,
ethyl-1-phenyl vinyl ether,
methyl-1-methyl vinyl ether,
ethyl-1-ethyl vinyl ether,
ethyl-1-methyl vinyl ether,
methyl vinyl ether,
ethyl vinyl ether,
propyl vinyl ether,
isopropyl vinyl ether,
n-butyl vinyl ether,
isobutyl vinyl ether,
sec-butyl vinyl ether,
tert-butyl vinyl ether,
pentyl vinyl ether,
hexyl vinyl ether,
heptyl vinyl ether,
octyl vinyl ether,
2-ethylhexyl vinyl ether,
decyl vinyl ether,
cetyl vinyl ether,
stearyl vinyl ether,
propadienyl vinyl ether,
isopropenyl vinyl ether,
2-propynyl vinyl ether,
3-butynyl vinyl ether,
3-methyl-2-butenyl vinyl ether,
allyl vinyl ether,
ethylene glycol monovinyl ether,
diethylene glycol-monovinyl ether,
triethylene glycol monovinyl ether,
triethanolamine monovinyl ether,
1-chloroethyl vinyl ether,
2-chloroethyl vinyl ether,
acetone oxime vinyl ether,
2-methylallyl vinyl ether,
3-phenylpropargyl vinyl ether,
cyclohexyl vinyl ether,
2-bromoethyl vinyl ether,
methoxyethyl vinyl ether,
2-butoxyethyl vinyl ether,
diethylene glycol methyl vinyl ether,
2-acetoxyethyl vinyl ether,
dimethylaminoethyl vinyl ether,
2-(diethylamino)ethyl vinyl ether,
aminoethyl vinyl ether,
3-dimethylaminopropyl vinyl ether,
trimethylsiloxyethyl vinyl ether,
trimethylsilyl vinyl ether,
triethylsilyl vinyl ether,
1-menthyl vinyl ether,
2-methoxyphenyl vinyl ether,
o-tolyl vinyl ether,
p-nitrophenyl vinyl ether,
2-naphthyl vinyl ether,
phenyl vinyl ether,
p-fluorophenyl vinyl ether,
p-methoxyphenyl vinyl ether,
p-aminophenyl vinyl ether,
2,4,6-trichlorophenyl vinyl ether,
2,4,6-trimethylphenyl vinyl ether,
2,4-dichlorophenyl vinyl ether,
2,4,6-tribromophenyl vinyl ether,
N-methylaminophenyl vinyl ether,
p-(dimethylamino)phenyl vinyl ether,
4-acetylphenyl vinyl ether, 2-nitrophenyl vinyl ether,
3-nitrophenyl vinyl ether,
p-iodophenyl vinyl ether,
p-chlorophenyl vinyl ether,
1-phenylethyl vinyl ether,
benzyl vinyl ether, and
2-piperidinoethyl vinyl ether, Examples of the cyclic monovinyl ethers include:
2,3-dihydrofuran,
3,4-dihydrofuran,
2,3-dihydro-2H-pyran,
3,4-dihydro-2H-pyran,
3,4-dihydro-2-methoxy-2H-pyran,
3,4-dihydro-4,4-dimethyl-2H-pyran-2-one, and
3,4-dihydro-2-ethoxy-2H-pyran.

The polyvalent vinyl ethers include divinyl ethers, trivinyl ethers and tetravinyl ethers.

Examples of the divinyl ethers include:
divinyl ether,
divinyl formal,
ethylene glycol divinyl ether,
diethylene glycol divinyl ether,
triethylene glycol divinyl ether,
triethanolamine divinyl ether,
1,3-propanediol divinyl ether,
1,4-butanediol divinyl ether,
1,4-cyclohexanediol divinyl ether,
4,4'-dihydroxyazobenzene divinyl ether,
hydroquinone divinyl ether, and
bisphenol A divinyl ether.

Examples of the trivinyl ethers include glycerol trivinyl ether.

Examples of the tetravinyl ethers include pentaerythritol tetravinyl ether.

In the preparation using the polyvalent vinyl ether, the polyvalent vinyl ether is sometimes crosslinked with plural thiol compounds to form a high-molecular weight compound depending upon the preparation conditions.

The vinyl thioethers include vinyl thioethers corresponding to the aforesaid vinyl ethers and cyclic monovinyl ethers. Examples of such vinyl thioethers include:
3-(trimethylsilyl)propyl vinyl thioether,
2-hydroxyethyl vinyl thioether,
2 (N-morpholino) ethyl-5-vinyl thioether,
2-(N-β-hydroxyethyl)aminoethyl-5-vinyl thioether,
2-aminoethyl vinyl thioether,
p-chlorophenyl vinyl thioether,
phenyl vinyl thioether, and
divinyl thioether.

Of these, particularly preferable is a thiol compound derivative wherein in the formula (20), A is an oxygen atom, $R^1$ is a hydrogen atom, $R^2$ is an alkyl group or a residue wherein a hydroxyl group is removed from (poly)alkylene glycol, and $R^3$ is a hydrogen atom.

Catalyst

When the thiol compound derivative of the invention is prepared by the reaction of the thiol compound with a vinyl ether or the like, a catalyst can be used when needed. As the catalyst, an acid catalyst is preferable, and examples of the acid catalysts employable herein include an acid phosphoric ester, hydrogen chloride, thionyl chloride and zinc chloride. Of these, an acid phosphoric ester can be preferably employed.

The acid phosphoric ester is represented by, for example, the following formula (21):

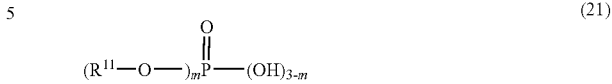

(21)

wherein $R^{11}$ is an alkyl group of 1 to 20 carbon atoms, a cycloalkyl group or an allyl group, and m is 1 or 2.

The acid phosphoric ester is a phosphoric acid monoester or diester of primary alcohol or secondary alcohol. Examples of the primary alcohols include 1-propanol, 1-butanol, 1-hexanol, 1-octanol and 2-ethylhexyl alcohol. Examples of the secondary alcohols include 2-propanol, 2-butanol, 2-hexanol, 2-octanol and cyclohexanol.

The acid phosphoric esters can be used singly or in combination of plural kinds.

When the acid phosphoric ester is used, the amount thereof is preferably in the range of about 0.05 to 5% by weight. If the amount of the acid phosphoric ester is small, the reaction rate sometimes becomes slow.

Reaction Solvent

The reaction of the thiol compound with the vinyl ether or the like can be carried out without a solvent or in a solvent. From the viewpoint of reaction rate and workability, the reaction is preferably carried out in a solvent. As the solvent, any of publicly known organic solvents is employable. For example, hydrocarbons, ethers, esters and ketones are employable. Specifically, there can be mentioned benzene, toluene, xylene, ethylbenzene, dioxane, tetrahydrofuran, diethyl ether, dipropyl ether, methyl acetate, ethyl acetate, butyl acetate, isopropyl acetate, acetone, methyl ethyl ketone, methyl isobutyl ketone, diethyl ketone and methyl propyl ketone.

Preparation of Thiol Compound Derivative

The thiol compound derivative of the invention can be obtained by contacting the thiol compound with the vinyl ethers at a temperature of preferably room temperature to 180° C. in a solvent or without a solvent and if necessary in the presence of an acid phosphoric ester. The reaction time is usually in the range of about 1 to 60 minutes.

The thiol compound derivative of the invention is a compound wherein all or a part of hydrogen atoms of thiol groups of the thiol compound that is a starting material are replaced with vinyl ethers or the like. By controlling the compounding ratio between the thiol compound and the vinyl ethers, a desired thiol compound derivative can be obtained. Specifically, they have only to be reacted in, for example, the following ratio.

When the trithiol compound (18) is used as a starting material and all of hydrogen atoms of three thiol groups (—SH) are replaced with a vinyl ether or the like to obtain the thiol compound derivative (1), the vinyl ether or the like is preferably used in an amount of 3 to 5 mol based on 1 mol of the trithiol compound (18).

When the trithiol compound (18) is used as a starting material and two of hydrogen atoms of three thiol groups (—SH) are replaced with a vinyl ether or the like to obtain the thiol compound derivative (8), the vinyl ether or the like is preferably used in an amount of 1.8 to 2.3 mol based on 1 mol of the trithiol compound (18).

When the thiol compound derivative (9) wherein a hydrogen atom of the thiol group is replaced with an alkali metal is obtained, 1.8 to 2.3 mol of the vinyl ether or the like is reacted with a salt obtained by reacting the trithiol compound (18) with an aqueous solution of sodium hydroxide or potassium hydroxide in an amount of 1 to 1.1 mol based on 1 mol of the trithiol compound (18).

When the dithiol compound (19) is used as a starting material and all of hydrogen atoms of two thiol groups (—SH) are replaced with a vinyl ether or the like to obtain the thiol compound derivative (10), the vinyl ether or the like is preferably used in an amount of 2 to 5 mol based on 1 mol of the dithiol compound (19).

When the dithiol compound (19) is used as a starting material and one of hydrogen atoms of two thiol groups (—SH) is replaced with a vinyl ether or the like to obtain the thiol compound derivative (15), the vinyl ether or the like is preferably used in an amount of 0.8 to 1.3 mol based on 1 mol of the dithiol compound (19).

When the thiol compound derivative (16) wherein a hydrogen atom of the thiol group is replaced with an alkali metal is obtained, 0.8 to 1.3 mol of the vinyl ether or the like is reacted with a salt obtained by reacting the dithiol compound (19) with an aqueous solution of sodium hydroxide or potassium hydroxide in an amount of 1 to 1.1 mol based on 1 mol of the dithiol compound (19).

Treatment

If a catalyst having activity is contained in the thiol compound derivative obtained, the thiol compound derivative sometimes undergoes hydrolysis depending upon the storage conditions, etc. Therefore, when the thiol compound derivative of the invention is prepared by the reaction of the thiol compound with the vinyl ethers in the presence of an acid catalyst, it is preferable to remove or deactivate the catalyst contained in the reaction product. When the catalyst contained is removed or deactivated, the thiol compound derivative is hardly decomposed and is stable even if it is stored in the atmosphere for a long period of time. Hence, the thiol compound derivative has excellent storage properties and is more practical.

When the thiol compound derivative is obtained by contacting the thiol compound with the vinyl ethers in the presence of an acid catalyst, particularly an acid phosphoric ester, it is desirable to treat the thiol compound derivative with hydrotalcite or metal alkoxide.

For the treatment using hydrotalcite, the reaction product containing an acid catalyst such as an acid phosphoric ester is contacted with hydrotalcite to allow the acid catalyst to be adsorbed on the hydrotalcite. The catalyst adsorbed on the hydrotalcide can be easily removed by, for example, filtration or precipitation.

In the treatment using metal alkoxide, the metal alkoxide is added to the reaction product containing an acid catalyst such as an acid phosphoric ester to break an acid group of the acid catalyst (e.g., phosphoric acid group of acid phosphoric ester) and thereby deactivate the catalyst contained in the reaction product. The metal of the metal alkoxide used is preferably a metal selected from the group consisting of Ti, Al and Zr.

Uses of Thiol Compound Derivative

The thiol compound derivative of the invention is useful as a crosslinking agent and can be used by adding it to various curable resins. In the thiol compound derivative of the invention, the thiol group (—SH) is protected by a group derived from vinyl ether or the like, so that when the thiol compound derivative is used as a vulcanizing agent for acrylic rubbers, etc., excellent storage stability is exhibited, and for example, gelation of rubbers in the processing stage or the subsequent storing stage can be inhibited. Further, in the vulcanization molding or the crosslinking, the thiol compound having —SH group can be readily regenerated by eliminating the protective group derived from the vinyl ether or the like by heating or other means. Therefore, the inherent reactivity can be easily restored to efficiently perform vulcanization or crosslinking of a chlorine-containing acrylic rubber or a resin containing an epoxy group, and hence a crosslinked product excellent in various properties can be obtained.

Elimination of the protective group derived from the vinyl ether or the like is preferably carried out by the use of an acid catalyst. Examples of the acid catalysts include halogenocarboxylic acid, sulfonic acid, sulfuric monoester, phosphoric monoester, phosphoric diester, boric monoester and boric diester.

After regeneration of the thiol group, the thiol compound derivative of the invention can be used for the addition to a double bond, addition to an epoxy ring or substitution of organic chlorine.

The thiol compound derivative can be used singly, or can be used in combination with an accelerator, a dehalogenating agent or the like.

Examples of the rubbers or the resins having a double bond include natural rubber (NR), isoprene rubber (IR), styrene-butadiene rubber (SBR), butadiene rubber (BR), nitrile rubber (NBR), ethylene-propylene rubber (EPDM), unsaturated polyester resin, and acrylic rubber wherein a double bond is introduced.

Example of the rubbers and the resins having an epoxy group include epoxy resin oligomer, and acrylic rubber containing an epoxy group.

Examples of the rubbers and the resins having organic chlorine include acrylic rubber, chloroprene rubber (CR), epichlorohydrin rubber (CO, ECO), chlorinated polyethylene, and Polyvinyl chloride.

The thiol compound derivative of the invention can be used by mixing it with one or more of the above rubbers or resins or adding it to a multi-layer structure of the above rubbers or resins.

The rubbers or the resins containing the thiol compound derivative of the invention are useful as materials for co-crosslinking molding or co-vulcanization molding, or they are vulcanization bonded to metals to form composite materials which are useful as molding materials.

Curable Composition

The curable composition of the invention contains the thiol compound derivative.

The curable composition of the invention contains a halogen-containing crosslinking polymer and the specific thiol compound derivative. The halogen-containing crosslinking polymer, the thiol compound derivative and other components are described below.

Halogen-Containing Crosslinking Polymer

The halogen-containing crosslinking polymer for use in the invention is a high-molecular weight compound which contains halogen and is crosslinkable. The halogen is a chlorine atom, a bromine atom or an iodine atom. Of these, a chlorine atom is preferable.

As the crosslinking polymer containing a chlorine atom, chlorine-containing acrylic rubber, epichlorohydrin rubber, chloroprene rubber, chlorosulfonated polyethylene or the like can be preferably employed. Of these, chlorine-containing acrylic rubber or epichlorohydrin rubber can be more preferably employed.

Halogen-Containing Acrylic Rubber

As the halogen-containing acrylic rubber, a copolymer of (A) at least one acrylate type monomer selected from alkyl (meth)acarylates and alkoxyalkyl (meth)acrylates, (B) a crosslinking point monomer, and if necessary, (C) an ethylenically unsaturated monomer copolymerizable with the acrylate type monomer can be preferably employed.

(A) Acrylate Type Monomer

The acrylate type monomer preferably employable is alkyl (meth)acrylate or alkoxyalkyl (meth)acrylate.

As the alkyl (meth)acarylate, alkyl (meth)acrylate in which the number of carbon atoms of the alkyl group is in the range of preferably 1 to 15, more preferably 1 to 10, can be desirably employed. Examples of such alkyl (meth)acrylates include acrylic esters and methacrylic esters, such as methyl (meth) acrylate, ethyl (meth)acrylate, n-propyl (meth)acrylate, isopropyl (meth)acrylate, n-butyl (meth)acrylate, isobutyl (meth)acrylate, n-amyl (meth)acrylate, n-hexyl (meth)acrylate, 2-ethylhexyl (meth)acrylate and n-octyl (meth)acrylate. These can be used singly or in combination of two or more kinds.

By the use of such alkyl (meth)acrylates, cured products having excellent low-temperature resistance and oil resistance can be obtained. A long alkyl chain is advantageous to the low-temperature resistance but is sometimes disadvantageous to the oil resistance. Contrary, a short alkyl chain indicates a opposite tendency. Therefore, of the above alkyl (meth)acrylates, ethyl acrylate and butyl acrylate are particularly preferable from the viewpoint of a balance between the oil resistance and the low-temperature resistance.

As the alkoxyalkyl (meth)acarylate, alkoxyalkyl (meth) acrylate in which the number of carbon atoms of the alkyl group on the alkoxy group is in the range of preferably 1 to 7, more preferably 1 to 4, and the number of carbon atoms of the alkyl group bonded to an oxygen atom of acrylate is in the range of preferably 1 to 15, more preferably 1 to 10, can be desirably employed. Examples of such alkoxyalkyl (meth) acrylates include methoxyethyl (meth)acrylate, 2-methoxyethyl (meth)acrylate, ethoxymethyl (meth)acrylate, 2-ethoxyethyl (meth)acrylate, 2-butoxyethyl (meth)acrylate and 2- or 3-ethoxypropyl (meth)acrylate. These can be used singly or in combination of two or more kinds.

Of these, 2-methoxyethyl (meth)acrylate and 2-ethoxyethyl (meth)acrylate are more preferably employed.

By the use of such alkoxyalkyl (meth)acrylates, cured products having excellent low-temperature resistance and oil resistance can be obtained.

The alkyl (meth)acrylate and the alkoxyalkyl (meth)acrylate mentioned above can be used independently or in combination. When the alkyl (meth)acrylate and the alkoxyalkyl (meth)acrylate are used in combination, the alkoxyalkyl (meth)acrylate is desirably used in an amount of preferably 10 to 40% by weight, more preferably 20 to 30% by weight, based on the alkyl (meth)acrylate. By the use of the alkyl (meth)acrylate and the alkoxyalkyl (meth)acrylate in such amounts, cured products excellent not only in low-temperature resistance and oil resistance but also in ordinary state properties such as heat resistance can be obtained.

(B) Crosslinking Point Monomer

The crosslinking point monomer (B) used for preparing the halogen-containing acrylic rubber for use in the invention is a polymerizable monomer having two or more functional groups and forms a crosslinking point of the halogen-containing acrylic rubber.

Examples of such bifunctional reactive monomers include a reactive halogen-containing vinyl monomer, an epoxy group-containing vinyl monomer, a carboxyl group-containing vinyl monomer, a diene type monomer, a hydroxyl group-containing monomer and an amide group-containing monomer.

Of these, at least one polymerizable monomer containing a reactive halogen atom is used in the invention. That is to say, as the crosslinking point monomer (B) for preparing the halogen-containing acrylic rubber for use in the invention, at least one reactive halogen-containing monomer selected from the above bifunctional monomers is used, and further a bifunctional monomer containing no halogen atom selected from the above bifunctional monomers may be used in combination.

The halogen is chlorine, bromine or iodine, and preferable is chlorine.

Of the above bifunctional reactive monomers, the polymerizable monomers containing a halogen atom include reactive halogen-containing monomers, such as chloroethyl vinyl ether, chloroethyl acrylate, vinylbenzyl chloride, vinyl chloroacetate, allyl chloroacetate and chloromethylstyrene.

When a combination of the reactive halogen-containing monomer and the bifunctional monomer containing no halogen atom is used as the crosslinking point monomer, it is preferable to use a carboxyl group-containing vinyl monomer of the above monomers.

Examples of the carboxyl group-containing vinyl monomers include monocarboxylic acids, such as acrylic acid and methacrylic acid; dicarboxylic acids, such as maleic acid, fumaric acid, itaconic acid and citraconic acid; and dicarboxylic monoesters, such as monomethyl maleate, monoethyl maleate, monobutyl maleate, monomethyl fumarate, monoethyl fumarate and monobutyl fumarate. These carboxyl group-containing vinyl monomers can be used singly or in combination of two or more kinds.

(C) Ethylenically Unsaturated Monomer

Examples of the ethylenically unsaturated monomers copolymerizable with the acrylate type monomer (A) include styrene, vinyltoluene, α-methylstyrene, vinylnaphthalene, acrylonitrile, methacrylonitrile, acrylamide, cyclohexyl acrylate, phenyl (meth)acrylate, benzyl acrylate, vinyl acetate, ethyl vinyl ether, butyl vinyl ether, ethylene, piperylene, isoprene, pentadiene, butadiene, 2-hydroxyethyl acrylate and 4-hydroxybutyl acrylate.

The above ethylenically unsaturated monomers (C) can be used singly or in combination of two or more kinds.

For the purpose of improving kneading processability, extrusion processability, etc., polyfunctional unsaturated monomers may be used when needed. Specifically, oligomers, e.g., di(meth)acrylates, such as ethylene glycol di(meth)acrylate, 1,4-butanediol di(meth)acrylate, 1,6-hexanediol di(meth)acrylate and 1,9-nonanediol di(meth)acrylate; alkylene glyols, such as neopentyl glycol di(meth)acrylate, tetraethylene glycol di(meth)acrylate, tripropylene glycol di(meth)acrylate and polypropylene glycol di(meth) acrylate; bisphenol A, EO adduct diacrylate, dimethyloltricyclodecane diacrylate, glycerol methacrylate acrylate and 3-acryloyloxyglycerol monomethacrylate may be used.

From the viewpoint of a balance between the low-temperature resistance, the oil resistance and the heat resistance, it is desirable that in the halogen-containing acrylic rubber for use in the invention, the component derived from the acrylate type monomer (A) is contained in an amount of preferably 20 to 85% by weight, more preferably 30 to 70% by weight, the component derived from the reactive halogen-containing polymerizable monomer as the crosslinking point monomer (B) is contained in an amount of preferably 0.1 to 15% by weight, more preferably 0.3 to 5% by weight, and the component derived from the ethylenically unsaturated monomer (C) is contained in an amount of preferably 0 to 79.9% by weight, more preferably 10 to 60% by weight, the total of said components (A), (B) and (C) being 100% by weight.

Although the molecular weight of the halogen-containing acrylic rubber is not specifically restricted, it is desirable that the weight-average molecular weight, as measured by gel permeation chromatography (GPC), is preferably not more than 1000000, more preferably 50000 to 500000, from the viewpoints of processability and mechanical properties such as rubber strength.

Preparation of Halogen-Containing Acrylic Rubber

The halogen-containing acrylic rubber can be prepared by a publicly known process. For example, the acrylate type monomer (A) in an amount of preferably 20 to 85% by weight, more preferably 30 to 70% by weight, the reactive halogen-containing polymerizable monomer as the crosslinking point monomer (B) in an amount of preferably 0.1 to 15% by weight, more preferably 0.3 to 5% by weight, and the ethylenically unsaturated monomer (C) in an amount of preferably 0 to 79.9% by weight, more preferably 10 to 60% by weight, the total of said components (A), (B) and (C) being 100% by weight, have only to be random polymerized in the presence of a radical polymerization initiator through various processes such as solution polymerization, bulk polymerization, emulsion polymerization and suspension polymerization.

Epichlorohydrin Rubber

The epichlorohydrin rubber employable in the invention can be obtained from a homopolymer of epichlorohydrin or by copolymerizing epichlorohydrin and alkylene oxide or unsaturated oxide.

The alkylene oxide preferably used is, for example, ethylene oxide or propylene oxide. The unsaturated oxide is, for example, allyl glycidyl ether.

The epichlorohydrin rubber can be prepared by a publicly known process. Commercially available epichlorohydrin rubber is also employable.

As the copolymer of epichlorohydrin and alkylene oxide or unsaturated oxide, a copolymer obtained by reacting epichlorohydrin with alkylene oxide or the like in equimolar amounts is preferably employed, and a copolymer containing the component derived from the alkylene oxide or the unsaturated oxide in an amount of preferably 10 to 90% by weight, more preferably 40 to 60% by weight, is desirable.

Although the molecular weight of the epichlorohydrin rubber is not specifically restricted, it is desirable that the weight-average molecular weight, as measured by gel permeation chromatography (GPC), is preferably not more than 200000, more preferably 5000 to 100000, from the viewpoints of processability and mechanical properties such as rubber strength.

Other Halogen-Containing Crosslinking Polymers

Examples of other halogen-containing crosslinking polymers employable in the invention include chloroprene rubber, chlorosulfonated polyethylene, chlorinated polyethylene and Polyvinyl chloride. As such polymers, commercially available ones can be employed.

Thiol Compound Derivative

The curable composition of the invention, which contains the halogen-containing crosslinking polymer, contains a thiol compound derivative having at least one functional group represented by the following formula (17) in one molecule.

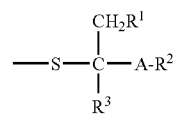

(17)

wherein A, $R^1$, $R^2$ and $R^3$ are the same as A, $R^1$, $R^2$ and $R^3$ in the aforesaid formula (2).

The compound having a functional group represented by the formula (17) for use in the invention is, for example, a derivative of 1,3,5-triazine-2,4,6-trithiol or 1,3,5-triazine-2,4-dithiol, and is a compound wherein the hydrogen atom of the thiol group (—SH) of the above thiol compound is substituted with a specific substituent. The thiol compound derivative can be obtained by reacting a compound having a thiol group (—SH), such as triazinethiol, with vinyl ethers.

Examples of the thiol compound derivatives include the aforesaid thiol compound derivatives of the invention, such as trithiol compound derivatives, dithiol compound derivatives and monothiol compound derivatives.

In addition to the above thiol compound derivatives, a thiol compound derivative obtained by contacting the trithiol compound or the dithiol compound with polyvalent vinyl ether is also available. The thiol compound derivative obtained by the reaction with polyvalent vinyl ether is a polymer-like compound.

In the above case, the resulting thiol compound derivative is a compound wherein all or a part of hydrogen atoms of thiol groups of triazinethiol that is a starting material are replaced with the polyvalent vinyl ether, and in general, the polyvalent vinyl ether reacts with another triazinethiol to form a crosslinked structure.

The thiol compound derivative contained in the curable composition of the invention is a compound wherein all or a part of hydrogen atoms of thiol groups of the thiol compound that is a starting material are replaced with vinyl ethers or the like, and by controlling the compounding ratio between the thiol compound and the vinyl ethers or the like, a desired thiol compound derivative can be obtained.

When monovinyl ether is used as the vinyl ether, the thiol compound derivative can be favorably obtained by the aforesaid process for preparing the thiol compound derivative of the invention.

When polyvalent vinyl ether is used as the vinyl ether, the thiol compound derivative can be obtained in the following manner.

The thiol compound represented by the aforesaid formula (18) or (19), namely, the thiol compound represented by the following formula (18) or (19) (wherein $R^5$ is the same as that of aforesaid), is contacted with the polyvalent vinyl ether to obtain a thiol compound derivative.

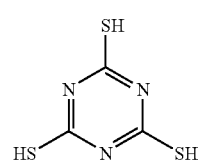

(18)

-continued

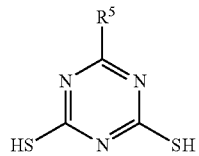
(19)

The thiol compound derivative thus obtained is a compound wherein all or a part of hydrogen atoms of thiol groups of the thiol compound that is a starting material are replaced with polyvalent vinyl ether, and in general, the polyvalent vinyl ether reacts with another thiol compound to form a crosslinked structure.

The compounding ratio between the thiol compound and the polyvalent vinyl ether usually varies depending upon the thiol compound and the polyvalent vinyl ether used, so that preferred compounding ratios, etc. due to the type of the thiol compound are described below.

(i) Reaction of Trithiol Compound (18) with Polyvalent Vinyl Ether (1) When the trithiol compound (18) is used as a starting material and all or a part of hydrogen atoms of three thiol groups (—SH) are replaced with divinyl ether to obtain a thiol compound derivative, the divinyl ether is desirably used in an amount of preferably 1.5 to 20 mol, more preferably 3 to 10 mol, based on 1 mol of the trithiol compound (18). In this case, though the divinyl ether may form a crosslinked structure together with the thiol compound, it is also possible that the divinyl ether does not form a crosslinked structure and a compound having a functional group represented by the aforesaid formula (5) is produced.

It is presumed that the divinyl ether having reacted with the thiol compound further reacts with another trithiol compound to form a crosslinked structure, as described above. More specifically, it is presumed that the end vinyl group of the functional group represented by, for example, the aforesaid formula (5) reacts with another thiol compound.

(2) When the trithiol compound (18) is used as a starting material and trivinyl ether is used as the polyvalent vinyl ether, the trivinyl ether is desirably used in an amount of preferably 1 to 15 mol, more preferably 3 to 10 mol, based on 1 mol of the trithiol compound (18). In this case, similarly to the case of using the divinyl ether, it is presumed that the trivinyl ether forms a crosslinked structure together with the thiol compound. In the resulting product, a thiol compound derivative wherein the trivinyl ether does not form a crosslinked structure may be present.

(3) When the trithiol compound (18) is used as a starting material and tetravinyl ether is used as the polyvalent vinyl ether, the tetravinyl ether is desirably used in an amount of preferably 0.75 to 10 mol, more preferably 3 to 7 mol, based on 1 mol of the trithiol compound (18). In this case, similarly to the case of using the divinyl ether, it is presumed that the tetravinyl ether forms a crosslinked structure together with the thiol compound. In the resulting product, a thiol compound derivative wherein the tetravinyl ether does not form a crosslinked structure may be present.

The thiol compound derivative obtained from the trithiol compound (18) and the polyvalent vinyl ether as described above is a composition having a crosslinked structure and having plural kinds of molecular weights, and is usually oligomer-like or polymer-like.

The viscosity of the thiol compound derivative is desired to be in the range of preferably 10 to 10000 cps, more preferably 1000 to 5000 cps.

The weight-average molecular weight of the thiol compound derivative is desired to be in the range of preferably 400 to 10000, more preferably 1000 to 5000.

(ii) Reaction of Dithiol Compound (19) with Polyvalent Vinyl Ether (1) When the dithiol compound (19) is used as a starting material and all or a part of hydrogen atoms of two thiol groups (—SH) are replaced with divinyl ether to obtain a thiol compound derivative, the divinyl ether is desirably used in an amount of preferably 1 to 20 mol, more preferably 3 to 10 mol, based on 1 mol of the dithiol compound (19). In this case, though the divinyl ether may form a crosslinked structure together with the thiol compound, a thiol compound derivative wherein the divinyl ether does not form a crosslinked structure may be produced.

(2) When the dithiol compound (19) is used as a starting material and trivinyl ether is used as the polyvalent vinyl ether, the trivinyl ether is desirably used in an amount of preferably 0.7 to 10 mol, more preferably 3 to 7 mol, based on 1 mol of the dithiol compound (19). In this case, similarly to the case of using the divinyl ether, it is presumed that the trivinyl ether forms a crosslinked structure together with the thiol compound. In the resulting product, a thiol compound derivative wherein the trivinyl ether does not form a crosslinked structure may be present.

(3) When the dithiol compound (19) is used as a starting material and tetravinyl ether is used as the polyvalent vinyl ether, the tetravinyl ether is desirably used in an amount of preferably 0.5 to 7 mol, more preferably 1 to 5 mol, based on 1 mol of the dithiol compound (19).

The thiol compound derivative obtained from the dithiol compound (19) and the polyvalent vinyl ether as described above is a composition having a crosslinked structure and having plural kinds of molecular weights, and is usually oligomer-like or polymer-like.

The viscosity of the thiol compound derivative is desired to be in the range of preferably 10 to 10000 cps, more preferably 100 to 1000 cps.

The weight-average molecular weight of the thiol compound derivative is desired to be in the range of preferably 400 to 10000, more preferably 1000 to 5000.

Vulcanization Accelerator

In the present invention, in addition to the halogen-containing crosslinking polymer and the thiol compound derivative, an organic acid metal salt is preferably used as the vulcanization accelerator, and an alkali metal salt of an organic carboxylic acid and/or an alkaline earth metal salt of an organic carboxylic acid is more preferably used.

Examples of the alkali metal salts of organic carboxylic acids employable herein include lithium salts, potassium salts and sodium salts of organic carboxylic acids such as saturated fatty acids of 3 to 18 carbon atoms, unsaturated fatty acids of 3 to 18 carbon atoms, aliphatic dicarboxylic acids and aromatic carboxylic acids. More specifically, there can be mentioned sodium stearate, potassium stearate, sodium oleate, potassium oleate, sodium 2-ethylhexanoate, sodium tartrate, potassium tartrate, sodium propionate and sodium acetate. Of these, potassium salts or sodium salts of fatty acids of 8 to 18 carbon atoms are particularly preferable. The potassium salts generally have a tendency to increase the vulcanizing rate as compared with the sodium salts.

Examples of the alkaline earth metal salts of organic carboxylic acids employable herein include magnesium salts, calcium salts, barium salts and zinc salts of organic carboxylic acids such as saturated fatty acids of 1 to 18 carbon atoms, unsaturated fatty acids of 3 to 18 carbon atoms, aliphatic dicarboxylic acids and aromatic carboxylic acids. More specifically, there can be mentioned magnesium stearate, calcium stearate, barium oleate, magnesium tartrate and calcium propionate. Of these, calcium salts or barium salts of fatty acids of 8 to 18 carbon atoms are particularly preferable.

Vulcanization Supplement Accelerator

The curable composition of the invention preferably contains a vulcanization supplement accelerator together with the vulcanization accelerator. As the vulcanization supplement accelerator, a publicly known vulcanization supplement accelerator is employable. Examples of such vulcanization supplement accelerators include oxides of metals such as Mg, Ca, Ba, Zn, Na, K, Li, Fe and Cu, hydroxides, carbonates, dialkyldithiocarbamates, borates, phosphates, silicates, hydrotalcite, quaternary ammonium salt, phosphonium salt, polyethylene glycol, polyethylene glycol monoalkyl ether and polyethylene glycol dialkyl ether.

More specifically, there can be mentioned magnesium oxide, magnesium hydroxide, barium hydroxide, magnesium carbonate, barium carbonate, calcium oxide, calcium hydroxide, calcium carbonate, calcium silicate, calcium phthalate, zinc oxide, tin oxide, lead oxide, zinc dibutylthiocarbamate, barium metaborate, cetyl trimethylammonium bromide and polyethylene glycol #600. The metal oxides, the metal hydroxides and the carbonates function as acid acceptors to increase the vulcanization acceleration effect. For controlling the crosslinking reaction rate, vulcanization retarders (premature crosslinking inhibitors), such as N-(cyclohexylthio) phthalimide, sulfonamide derivatives and organic acids, may be used.

They can be used singly or in combination of plural kinds.

In the present invention, it is desirable to use, as the vulcanization supplement accelerator, an onium compound, such as an ammonium compound, a phosphonium compound, an arsonium compound, a stibonium compound, a sulfonium compound, a selenonium compound, a stannonium compound or an iodonium compound.

Examples of the onium compounds preferably employable as the vulcanization supplement accelerator in the invention include quaternary ammonium compounds, such as methyltrioctylammonium chloride, laurylpyridinium chloride, tetraheptylammonium chloride, tetrabutylammonium stearate and cetylmethylammonium bromide; and quaternary phosphonium salts, such as methyltrioctylphosphonium tetrafluoroborate, benzyltrioctylphosphonium bromide, benzyltrioctylphosphonium chloride, methyltrioctylphosphonium acetate, methyltrioctylphosphonium dimethyl phosphate and methyltrioctylphosphonium chloride.

In the present invention, polyalkylene oxides such as polyethylene oxide and polypropylene oxide are also preferably used as the vulcanization supplement accelerator.

Anti-Aging Agent

It is also preferable that the curable composition of the invention contains an anti-aging agent in addition to the halogen-containing crosslinking polymer and the thiol compound derivative. As the anti-aging agent, an anti-aging agent of amine type, quinoline type, phenol type, phosphite ester type or thioether type is preferably employed.

In an acrylic rubber composition, a diphenylamine type anti-aging agent such as 4,4-bis($\alpha,\alpha$-dimethylbenzyl)diphenylamine is usually used singly, but in the present invention, it is desirable to use a diphenylamine-type anti-aging agent and a sulfur type anti-aging agent or a phosphorus type anti-aging agent in combination.

Preferred examples of the sulfur type anti-aging agents include thioether type compounds, such as dilauryl 3,3-thiodipropionate, distearyl 3,3-thiodipropionate and pentaerythritol tetrakis (3-laurylthiopropionate). Preferred examples of the phosphorus type anti-aging agents include phosphorous acid type compounds, such as tris(nonylphenyl) phosphite.

Other Compounding Ingredients

The curable composition of the invention may further contain, as compounding ingredients, additives other than the above-mentioned ones within limits not detrimental to the objects of the present invention. Examples of such compounding ingredients include a reinforcing agent, a filler, a plasticizer, a processing aid, a pigment, a lubricant and a resin other than the halogen-containing crosslinking polymer.

Curable Composition

The curable composition of the invention contains the halogen-containing crosslinking polymer and the thiol compound derivative, and can further contain an organic acid metal salt, a vulcanization supplement accelerator, an anti-aging agent, a reinforcing agent, a filler, a plasticizer, a pigment, a processing aid, a lubricant, etc., when needed.

The process for preparing the curable composition comprising the halogen-containing crosslinking polymer and the thiol compound derivative is not specifically restricted, and the composition can be prepared by a publicly known process. For example, the components are blended, kneaded by, for example, a roll or a closed kneader, and then vulcanization molded under the crosslinking conditions publicly known.

The amount of the thiol compound derivative in the curable composition is desired to be in the range of preferably 0.1 to 5% by weight, more preferably 1 to 3% by weight, based on the halogen-containing crosslinking polymer.

If the amount of the thiol compound derivative is less than 0.1% by weight, the crosslink density is sometimes decreased. If the amount thereof is more than 5% by weight, the crosslink density becomes so high that the molded product sometimes becomes brittle.

The curable composition obtained can be crosslinked by heating. The crosslinking molding temperature is preferably in the range of about 130 to 200° C. If the crosslinking temperature is lower than 130° C., the composition is not crosslinked or is insufficiently crosslinked in some cases. If the crosslinking temperature is higher than 200° C., the crosslinking reaction proceeds so rapidly that the molding failure may occur.

The crosslinking time varies depending upon the crosslinking method, temperature or the shape and is not restricted, but usually, it is in the range of 1 minute to 5 hours. The heating method is not specifically restricted, and heating can be carried out by means of press, steam, oven, hot air or the like.

The curable composition of the invention uses the specific compound derivative as a crosslinking agent. That is to say, the thiol group (—SH) of the thiol compound derivative is protected by a group derived from the vinyl ether or the like, so that when the thiol compound derivative is used as a vulcanizing agent for a chlorine-containing acrylic rubber, etc., excellent storage stability is exhibited, and for example, gelation of the rubber in the processing stage or the subsequent storing stage can be inhibited. Further, in the vulcanization molding or the crosslinking molding, the protective group derived from the vinyl ether or the like can be eliminated by heating or other means to easily regenerate the thiol compound having —SH group. Therefore, the inherent reactivity can be easily restored to efficiently perform vulcanization or crosslinking of a chlorine-containing acrylic rubber or a resin containing an epoxy group, and as a result, a crosslinked product excellent in various properties can be obtained.

Elimination of the protective group derived from the vinyl ether or the like is preferably carried out by the use of an acid catalyst. Examples of such acid catalysts include halogenocarboxylic acid, sulfonic acid, sulfuric monoester, phosphoric monoester, phosphoric diester, boric monoester and boric diester.

After regeneration of the thiol group, the thiol compound derivative of the invention participates in the addition to a double bond, addition to an epoxy ring or substitution of organic chlorine. The thiol compound derivative can be used singly, or can be used in combination with an accelerator, a dehalogenating agent or the like.

The molded product obtained as above through crosslinking has excellent hardness, tensile strength and compression set, and is useful for hoses, sealing parts and the like.

The thiol compound derivative of the invention is useful as a crosslinking agent of a curable composition consisting of rubber, resin, etc., and a composition containing the thiol compound derivative of the invention is excellent in storage stability before molding-cure because the reaction of the thiol compound is restrained. In the molding of the composition, the thiol compound having high reactivity can be easily regenerated by heat, and hence, curing can be carried out rapidly at any time. Further, by the use of the thiol compound derivative of the invention as a vulcanizing agent of a curable composition, it becomes unnecessary to add a premature vulcanization inhibitor for controlling storage properties or curability, which sometimes deteriorates various properties of a cured product. Hence, a cured product excellent in various properties can be obtained.

Furthermore, because the thiol compound derivative in the curable composition of the invention is protected by a specific protective group to thereby restrain the reaction, the curable composition exhibits excellent storage stability when stored before the molding-cure. In the molding of the curable composition, the thiol compound having high reactivity can be easily regenerated by heat, and hence, curing can be carried out rapidly at any time. By the use of the thiol compound derivative of the invention as a vulcanizing agent of a curable composition, it becomes unnecessary to add a premature vulcanization inhibitor for controlling storage properties or curability, which sometimes deteriorates various properties of a cured product. Hence, a cured product excellent in various properties can be obtained. Moreover, when the curable composition of the invention contains a specific vulcanization accelerator, a specific vulcanization supplement accelerator and a specific anti-aging agent, the composition is excellent in storage stability, crosslinking rate and physical properties of its crosslinked molded product with a better balance of those properties.

EXAMPLE

The present invention is further described with reference to the following examples, but it should be construed that the invention is in no way limited to those examples.

In the following examples and comparative examples, IR measurements were carried out by the use of FT/IR-7000 type Fourier transform infrared spectrophotometer (manufactured by Nippon Bunko Kogyo K. K.).

Example 1

In a four-necked flask equipped with a thermometer, a reflux condenser and a stirrer, 35.46 g (0.2 mol) of 1,3,5-triazine-2,4,6-trithiol, 0.3 g of acid butyl phosphate (AP-4, available from Daihachi Kagaku Kogyo K. K.), 72.1 g (0.72 mol) of n-butyl vinyl ether and 190 g of acetone were placed, and they were stirred and reacted at 70° C. until a homogeneous solution was obtained. After the reaction was completed, the reaction solution was cooled and concentrated to obtain a yellow liquid containing crystals. The crystals were separated by filtration to obtain 89.1 g of a viscous yellow liquid (thiol compound derivative A).

Figure 1:
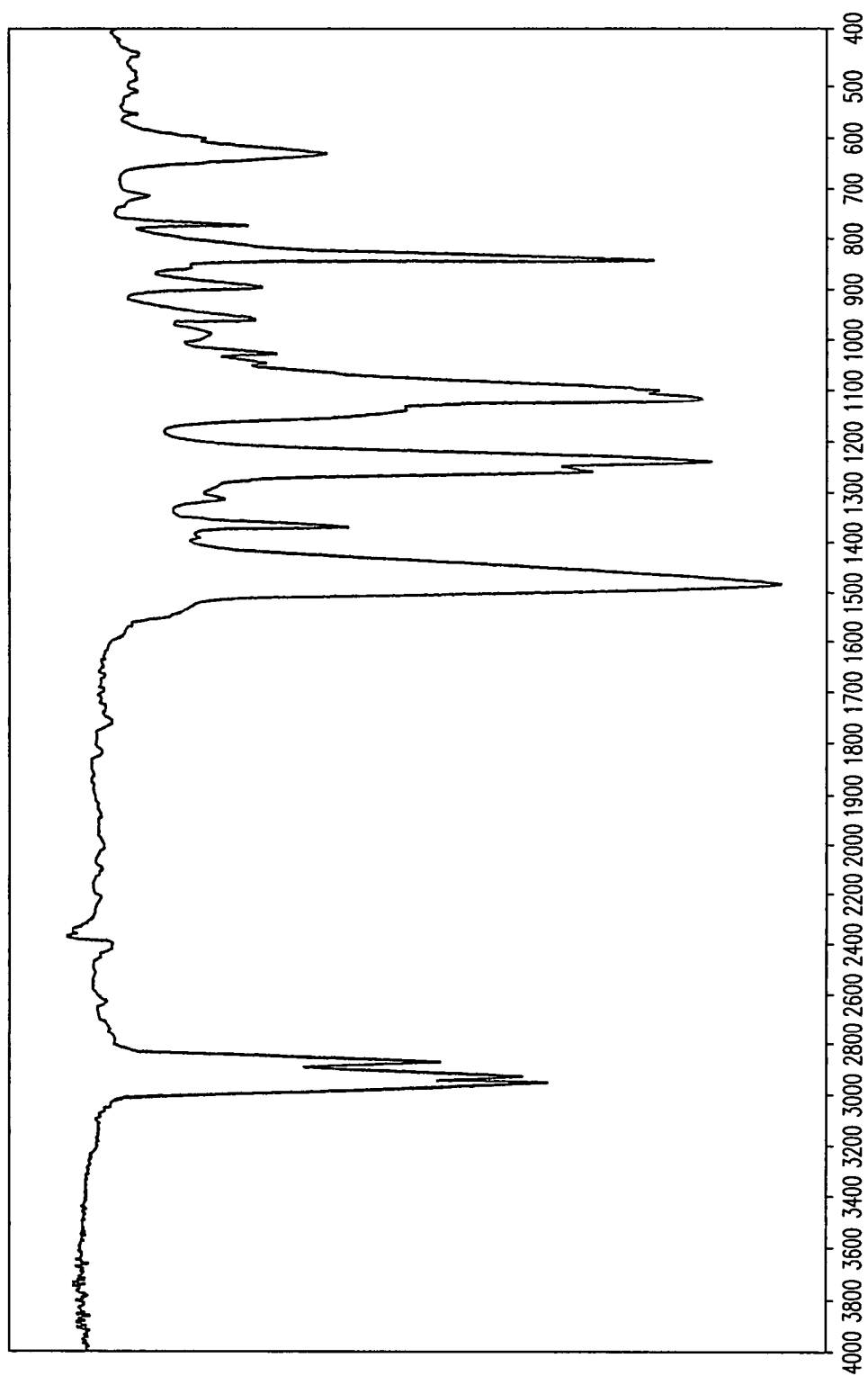
FIG. 1 is a chart of an IR absorption spectrum of a synthetic substance obtained in Example 1.
Figure 2:
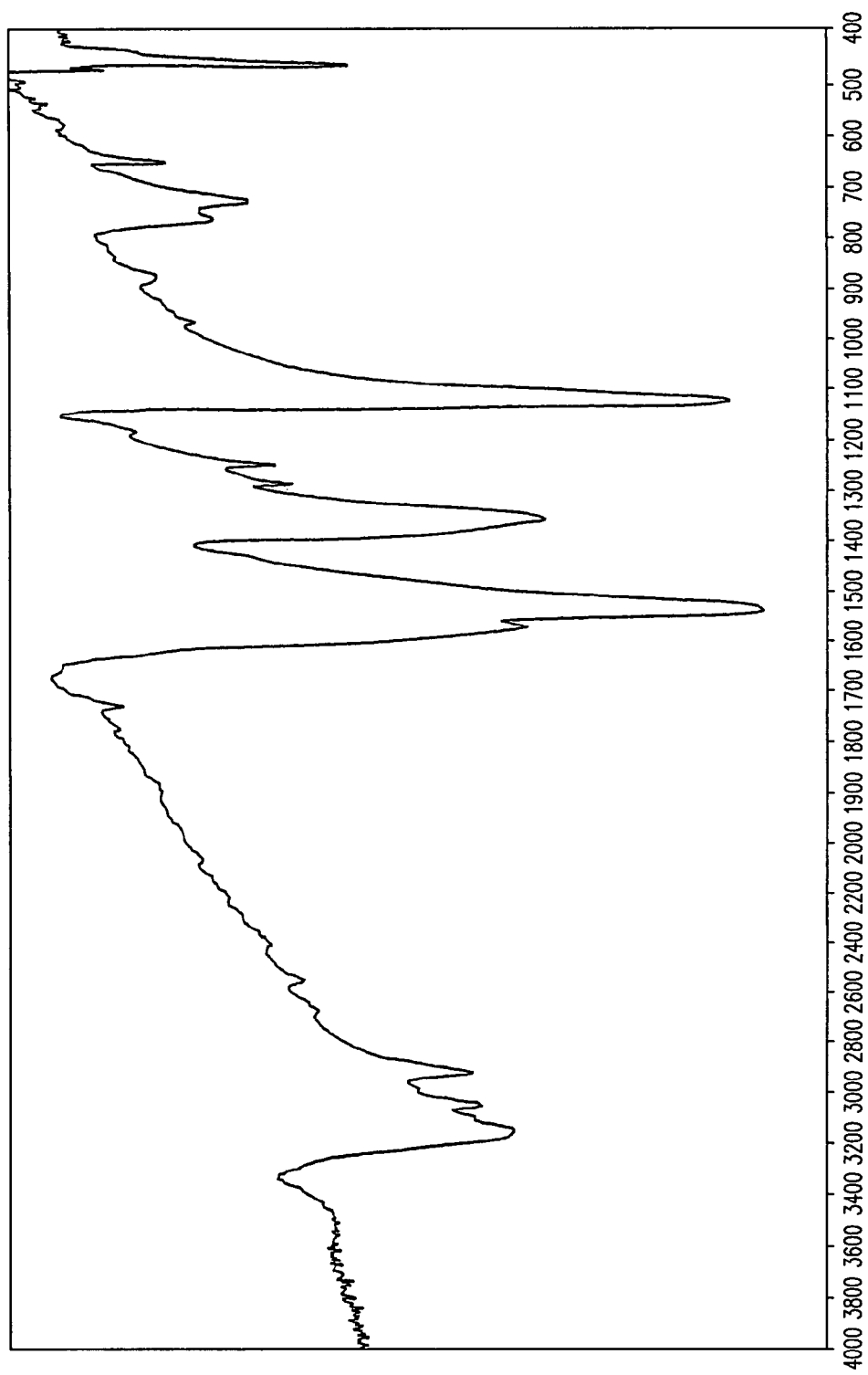
FIG. 2 is a chart of an IR absorption spectrum of 1,3,5-triazine-2,4,6-trithiol that is a starting material for synthesis.

The viscous yellow liquid thus obtained was applied to a KRS-5 cell to measure an IR absorption spectrum. A chart of the measurement result is shown in FIG. 1. An IR absorption spectrum of 1,3,5-triazine-2,4,6-trithiol which was a starting material was also measured by the KBr tablet method. A chart of the measurement result is shown in FIG. 2.

As can be seen from FIG. 1, absorption at about 1619 cm$^{-1}$, that is absorption by the double bond of n-butyl vinyl ether, disappears. As can be seen from FIG. 1, further, absorption at about 1590 cm$^{-1}$, that is absorption by the SH bond (enol structure) or the C=S bond (keto structure) of the 1,3,5-triazine-2,4,6-trithiol and appears in FIG. 2, also disappears. From the results, it has been confirmed that the viscous yellow liquid A, which was the resulting product, was an adduct of 1,3,5-triazine-2,4,6-trithiol with n-butyl vinyl ether, namely, a thiol compound derivative of the following formula wherein the thiol group was added to the vinyl group. The yield of the product (thiol compound derivative A) was 93% based on the 1,3,5-triazine-2,4,6-trithiol.

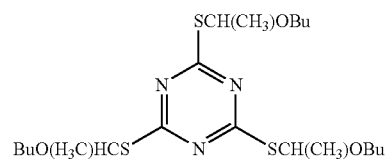

Figure 3:
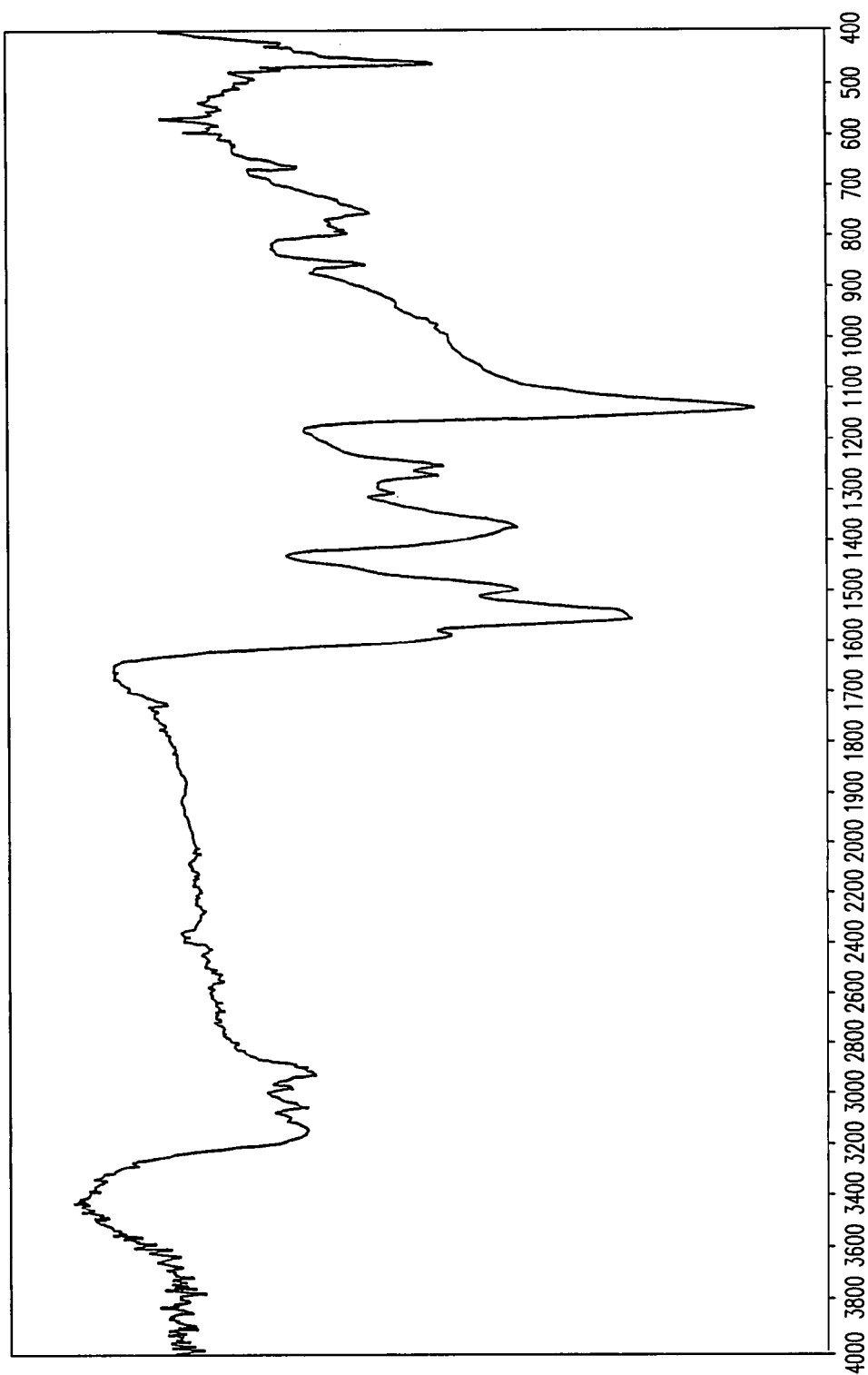
FIG. 3 is a chart of an IR absorption spectrum of a sample obtained by heating the synthetic substance obtained in Example 1, in the atmosphere.

Then, a part of the resulting viscous yellow liquid A was heated at a temperature of 180° C. for 5 minutes in the atmosphere. As a result, the liquid became a solid. When an IR absorption spectrum of the solid was measured by the KBr tablet method, a result shown in FIG. 3 was obtained. In the IR absorption spectrum of FIG. 3, there is absorption at about 1590 cm$^{-1}$ assigned to the 1,3,5-triazine-2,4,6-trithiol which was a starting material, and it has been confirmed that the protective group of the resulting compound represented by the aforesaid formula was eliminated by heat and the starting material compound was formed.

Example 2

A viscous yellow liquid (thiol compound derivative B) of 91.0 g was obtained in the same manner as in Example 1, except that instead of 72.1 g (0.72 mol) of n-butyl vinyl ether, isobutyl vinyl ether was used in the same amount. The viscous yellow liquid thus obtained was applied to a KRS-5 cell to measure an IR absorption spectrum. A chart of the measurement result is shown in FIG. 4.

Figure 4:
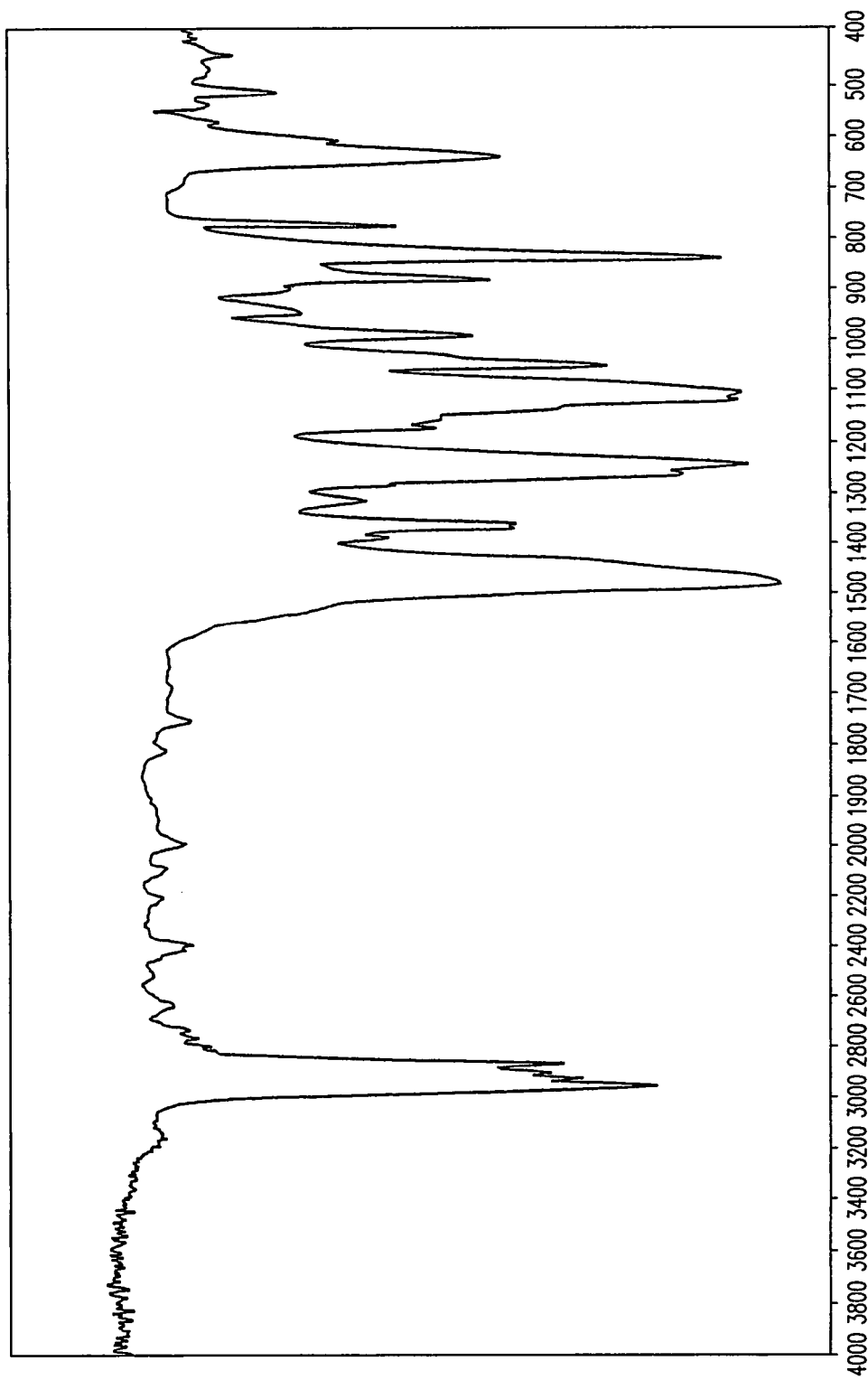
FIG. 4 is a chart of an IR absorption spectrum of a synthetic substance obtained in Example 2.

As can be seen from FIG. 4, absorption at about $1621\ cm^{-1}$ assigned to the double bond of isobutyl vinyl ether disappears. As can be seen from FIG. 4, further, absorption at about $1590\ cm^{-1}$, that is assigned to the SH bond (enol structure) or the C=S bond (keto structure) of the 1,3,5-triazine-2,4,6-trithiol and appears in FIG. 2, also disappears. From the results, it has been confirmed that the resulting product B was an adduct of 1,3,5-triazine-2,4,6-trithiol with isobutyl vinyl ether, namely, a thiol compound derivative wherein the thiol group was added to the vinyl group. The yield of the product (thiol compound derivative B) was 93% based on the 1,3,5-triazine-2,4,6-trithiol.

Figure 5:
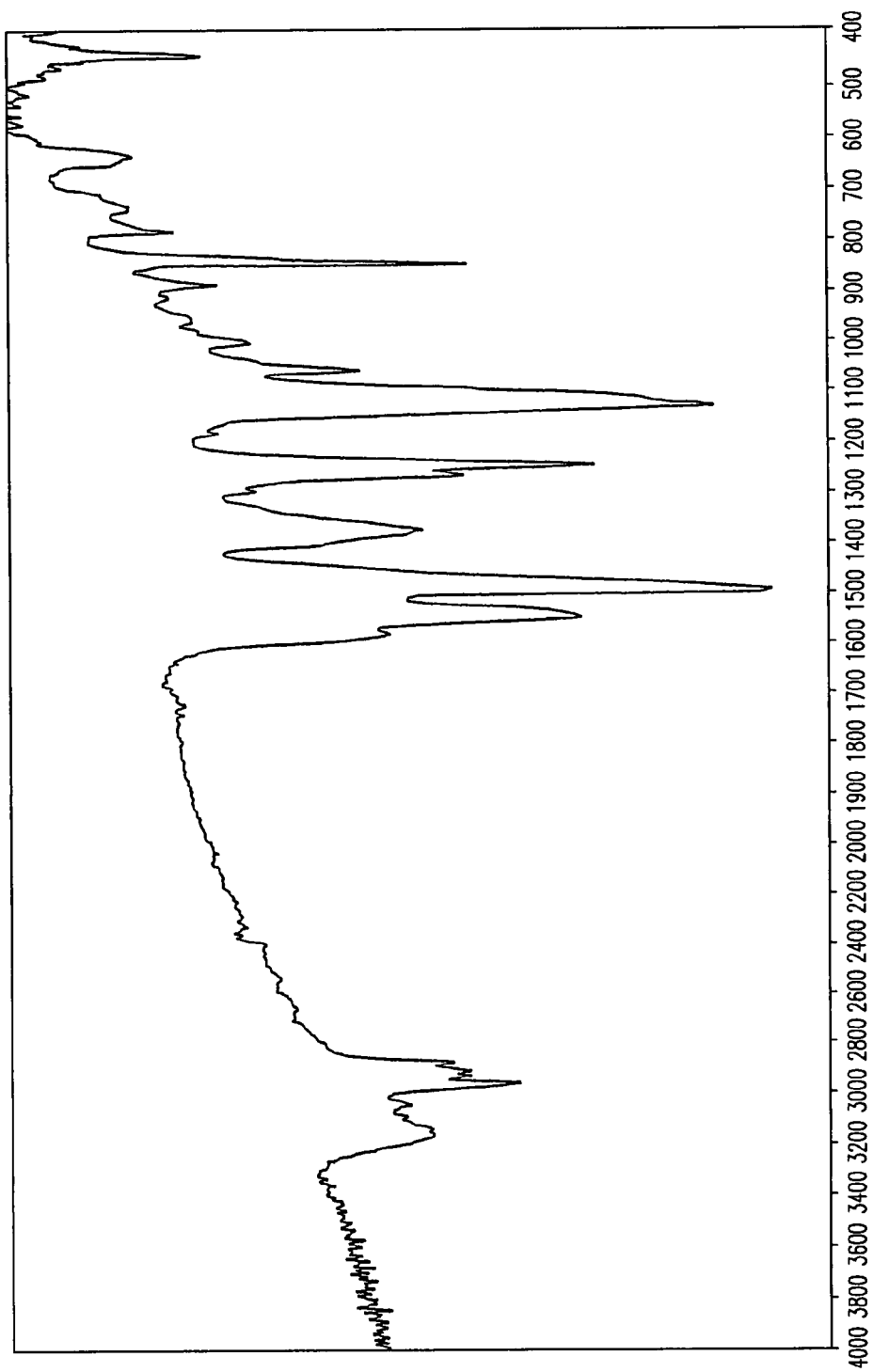
FIG. 5 is a chart of an IR absorption spectrum of a sample obtained by heating the synthetic substance obtained in Example 2, in the atmosphere.

Then, a part of the resulting viscous yellow liquid B was heated at a temperature of 180° C. for 5 minutes in the atmosphere. As a result, the liquid became a solid. When an IR absorption spectrum of the solid was measured by the KBr tablet method, a result shown in FIG. 5 was obtained. In the IR absorption spectrum of FIG. 5, there is absorption at about $1590\ cm^{-1}$ assigned to the 1,3,5-triazine-2,4,6-trithiol which was a starting material, and it has been confirmed that the protective group of the resulting compound was eliminated by heat and the starting material compound was formed.

Examples 3 to 7, Comparative Examples 1 to 5

The viscous yellow liquid A obtained in Example 1 and the viscous yellow liquid B obtained in Example 2 were each blended with the components shown in Table 7 in the proportions shown in Table 7 and kneaded by an 8-inch open roll to prepare curable compositions.

As the Mooney scorch of the resulting curable compositions before curing, values immediately after blending and values after storage for 7 days under the conditions of a temperature of 40° C. and a relative humidity (RH) of 40% were measured by the method of JIS K 6300.

The curable compositions were heated at 180° C. for 8 minutes to perform primary vulcanization and then further heated at 175° C. for 4 hours to perform secondary vulcanization and thereby cured. The resulting cured products were measured on the hardness, tensile strength, elongation and compression set. The secondary vulcanization products were further heated at 175° C. for 70 hours and then measured on the rate of change in hardness, rate of change in tensile strength and rate of change in elongation. Measurements of the properties were made in accordance with JIS K 6301. The results are set forth in Table 8.

Further, vulcanizing rates of the compositions obtained in the examples and the comparative examples were measured by the use of a curelastometer V type (manufactured by Orientech K. K.). The curelastometer curves obtained are shown in FIG. 6.

TABLE 7

|  | Ex. 3 | Ex. 4 | Ex. 5 | Ex. 6 | Ex. 7 | Comp. Ex. 1 | Comp. Ex. 2 | Comp. Ex. 3 | Comp. Ex. 4 | Comp. Ex. 5 |
|---|---|---|---|---|---|---|---|---|---|---|
| Acrylic rubber 1 | 100 |  |  |  |  | 100 | 100 |  |  |  |
| Acrylic rubber 2 |  | 100 | 100 |  |  |  |  | 100 |  |  |
| Acrylic rubber 3 |  |  |  | 100 |  |  |  |  | 100 |  |
| Epichlorohydrin rubber |  |  |  |  | 100 |  |  |  |  | 100 |
| Stearic acid | 1 | 1 | 1 | 1 | 2 | 1 | 1 | 1 | 1 | 2 |
| Diablack H | 60 | 55 | 55 | 55 |  | 60 | 60 | 55 | 55 |  |
| SEAST GSO |  |  |  |  | 40 |  |  |  |  | 40 |
| NOCRAC CD | 2 | 2 | 2 | 2 | 2 | 2 | 2 | 2 | 2 | 2 |
| TCY |  |  |  |  |  | 0.7 | 0.7 | 0.4 | 0.6 | 0.9 |
| TCYBVE | 1.5 | 0.9 |  | 1.3 | 2.0 |  |  |  |  |  |
| TCYIBVE |  |  | 0.9 |  |  |  |  |  |  |  |
| NS Soap | 3 | 3 | 3 | 3 |  | 3 | 3 | 3 | 3 |  |
| MgO #150 |  |  |  |  | 1.5 |  |  |  |  | 1.5 |
| PVI |  |  |  |  |  |  | 1 |  |  |  |

Notes:

In the table, a unit for each numerical value is part by weight.

Acrylic rubber 1: acrylic rubber obtained by polymerizing ethyl acrylate, butyl acrylate, methoxyethyl acrylate and chloromethylstyrene (charge weight ratio = 50:20:30:1.5) by conventional procedure Acrylic rubber 2: acrylic rubber obtained by polymerizing ethyl acrylate, butyl acrylate, methoxyethyl acrylate and vinyl chloroacetate (charge weight ratio = 40:40:50:2) by conventional procedure Acrylic rubber 3: acrylic rubber obtained by polymerizing ethyl acrylate, butyl acrylate, methoxyethyl acrylate and chloroethyl vinyl ether (charge weight ratio = 50:20:30:5) by conventional procedure Epichlorohydrin rubber: Epichlomer C (available from Osaka Soda K.K.)

Diablack H: available from Mitsubishi Chemical Corporation, HAF carbon black

SEAST GSO: available from Tokai Carbon K.K., FEF carbon black

NOCRAC CD: available from Ouchi Shiko Kagaku K.K., secondary amine type anti-aging agent TCY: 1,3,5-triazine-2,4,6-trithiol TCYBVE: thiol compound derivative prepared in Example 1

TCYIBVE: thiol compound derivative prepared in Example 2

NS Soap: available from Kao Soap Co., Ltd., semi-hard beef tallow fatty acid soda MgO #150: available from Kyowa Kagaku K.K., magnesium oxide PVI: available from Japan Monsant K.K., N-cyclohexylthiophthalimide (premature vulcanization inhibitor)

TABLE 8

|  | Ex. 3 | Ex. 4 | Ex. 5 | Ex. 6 | Ex. 7 | Comp. Ex. 1 | Comp. Ex. 2 | Comp. Ex. 3 | Comp. Ex. 4 | Comp. Ex. 5 |
|---|---|---|---|---|---|---|---|---|---|---|
| Mooney scorch (125° C.) | | | | | | | | | | |
| ML1 + 4 | 69 | 58 | 63 | 69 | 33 | impossible | 100 | impossible | 62 | 57 |
| t5 (min) | 5.8 | 12.1 | 13.0 | 20.4 | 15.7 | impossible | 2.9 | impossible | 10.4 | 10.8 |
| Mooney scorch (125° C.) after storage of 40° C., 40% RH and 7 days | | | | | | | | | | |
| ML1 + 4 | 53 | 46 | 40 | 34 | 48 | unmeasured | impossible | unmeasured | 38 | 92.5 |
| t5 (min) | 6.2 | 6.7 | 6.9 | 21.0 | 9.8 | unmeasured | impossible | unmeasured | 13.5 | 6.5 |
| Properties after secondary vulcanization | | | | | | | | | | |
| Hardness(JIS-A) | 7.4 | 63 | 62 | 69 | 60 | unmeasured | 73 | unmeasured | 67 | 63 |
| Tensile strength (MPa) | 12.4 | 10.8 | 11.3 | 11.0 | 7.3 | unmeasured | 12.1 | unmeasured | 11.7 | 9.5 |
| Elongation (%) | 160 | 220 | 240 | 220 | 360 | unmeasured | 190 | unmeasured | 210 | 410 |
| Compression set (%) (150° C., 70 hrs) | 13 | 11 | 10 | 12 | 26 | unmeasured | 19 | unmeasured | 17 | 32 |
| Properties after heating of secondary vulcanization product | | | | | | | | | | |
| Rate of change in hardness (%) | +3 | +5 | +7 | +7 | −23 | unmeasured | +5 | unmeasured | +6 | −25 |
| Rate of change in tensile strength (%) | −8 | −4 | +1 | −6 | −92 | unmeasured | −8 | unmeasured | −3 | −95 |
| Rate of change in elongation (%) | +5 | −18 | −4 | −9 | −56 | unmeasured | −5 | unmeasured | −10 | −76 |

Notes:
In the table, the term "impossible" means that the measurement is impossible.

When triazinetrithiol publicly known and the acrylic rubber 1 obtained by copolymerization with chloromethylstyrene as a crosslinking group were used (Comparative Example 1) or when triazinetrithiol publicly known and the acrylic rubber 2 obtained by copolymerization with vinyl chloroacetate as a crosslinking group were used (Comparative Example 3), curing proceeded so rapidly that the Mooney viscosity and the scorch time could not be measured. Even if the premature vulcanization inhibitor was added (Comparative Example 2), the Mooney scorch after storage for 7 days at 40° C. and 40% RH was immeasurable, and the long-term storage stability was poor.

On the other hand, when the thiol compound derivative obtained in Example 1 or 2 and the acrylic rubber 1 obtained by copolymerization with chloromethylstyrene as a crosslinking group or the acrylic rubber 2 obtained by copolymerization with vinyl chloroacetate as a crosslinking group were used (Examples 3 to 5), the long-term stability and the curability were both satisfactory, and besides, the properties were excellent.

When triazinetrithiol publicly known and the acrylic rubber 3 obtained by copolymerization with chloroethyl vinyl ether as a crosslinking group were used (Comparative Example 4), the compression set was poorer as compared with the case where the thiol compound derivative obtained in Example 1 and the acrylic rubber 3 were used (Example 6).

When triazinetrithiol publicly known and epichlorohydrin were used (Comparative Example 5), the storage properties, curability and compression set were poorer as compared with the case where the thiol compound derivative obtained in Example 1 and the epichlorohydrin rubber were used (Example 7).

When curelastometer curves of the compositions of Examples 3 to 7 and Comparative Examples 2, 4 and 5 at a crosslinking temperature of 180° C. were measured, results shown in FIG. 9 were obtained. Measurements of the curelastometer curves were made in accordance with JIS K 6300 using a curelastometer V type (manufactured by Orientech K. K.). The measurements were made under the conditions of an amplitude of ±1° and a frequency of 100 cps. In FIG. 6, the curelastometer curves of the compositions of Examples 3 to 7 and Comparative Examples 2, 4 and 5 are shown.

TABLE 9

|  | $tc_{10}$ (min) | $tc_{90}$ (min) | $t_{\Delta 80}$ (min) | $T_{10}$ (kg·cm) | $M_L$ (kg·cm) | $M_H$ (kg·cm) |
|---|---|---|---|---|---|---|
| Ex. 3 | 0.76 | 4.51 | 3.75 | 9.2 | 2.2 | 9.4 |
| Ex. 4 | 0.85 | 4.60 | 3.75 | 7.7 | 2.0 | 7.8 |
| Ex. 5 | 0.86 | 4.61 | 3.75 | 7.8 | 1.8 | 7.9 |
| Ex. 6 | 1.92 | 8.25 | 6.33 | 8.3 | 1.9 | 8.8 |
| Ex. 7 | 2.55 | 8.99 | 6.44 | 5.1 | 1.6 | 5.7 |
| Comp. Ex. 2 | 0.58 | 5.28 | 4.70 | 8.3 | 2.3 | 8.5 |
| Comp. | 1.83 | 8.41 | 6.58 | 7.3 | 2.2 | 7.8 |

TABLE 9-continued

| | $tc_{10}$ (min) | $tc_{90}$ (min) | $t_{\Delta 80}$ (min) | $T_{10}$ (kg·cm) | $M_L$ (kg·cm) | $M_H$ (kg·cm) |
|---|---|---|---|---|---|---|
| Ex. 4 Comp. Ex. 5 | 2.37 | 8.97 | 6.60 | 6.3 | 2.1 | 6.9 |

$tc_{10}$ (min): time required for torque to reach 10% of $(M_H - M_L)$; this means an induction period (scorch time).
$tc_{90}$ (min): time required for torque to reach 90% of $(M_H - M_L)$; this means the highest vulcanization point.
$t_{\Delta 80}$ (min): value of $tc_{90} - tc_{10}$; this is a vulcanizing rate index of a certain kind.
$T_{10}$ (kg·cm): value of torque after 10 minutes from the beginning of the test
$M_L$ (kg·cm): minimum value of torque
$M_H$ (kg·cm): maximum value of torque Examples 8 to 33, Comparative Example 6

The viscous yellow liquid B obtained in Example 2, the acrylic rubber of ethyl acrylate/butyl acrylate/methoxyethyl acrylate/vinyl chloroacetate (40/40/20/2) and the components shown in Table 10, Table 11 and Table 12 except the vulcanizing agent and the vulcanization accelerator were kneaded by a 3.6-liter Banbury mixer (manufactured by Kobe Steel, Ltd.), then the vulcanizing agent and the vulcanization accelerator were added, and they were kneaded by an open roll to prepare curable compositions shown in Table 10, Table 11 and Table 12.

As the Mooney scorch of the resulting curable compositions before curing, values immediately after blending and values after storage for 7 days under the conditions of a temperature of 40° C. and a relative humidity (RH) of 40% were measured by the method of JIS K 6300.

The curable compositions were subjected to press vulcanization molding at 180° C. for 8 minutes to perform primary vulcanization and then further subjected to secondary vulcanization at 175° C. for 4 hours to cure them. Properties of the primary vulcanization products and the secondary vulcanization products are set forth in Table 13, Table 14 and Table 15.

TABLE 10

(Composition)

| | Ex. 8 | Ex. 9 | Ex. 10 | Ex. 11 | Ex. 12 | Ex. 13 | Ex. 14 | Ex. 15 | Comp. Ex. 6 |
|---|---|---|---|---|---|---|---|---|---|
| Acrylic rubber*1 | 100 | 100 | 100 | 100 | 100 | 100 | 100 | 100 | 100 |
| Stearic acid | 1 | 1 | 1 | 1 | 1 | 1 | 1 | 1 | 1 |
| 4,4'-Bis(α,α-dimethylbenzyl)diphenylamine | 2 | 2 | 2 | | 2 | 2 | 2 | 2 | 2 |
| MAF (N550) carbon | 50 | 50 | 50 | 50 | 50 | 50 | 50 | 50 | 50 |
| SRF (N774) carbon | 35 | 35 | 35 | 35 | 35 | 35 | 35 | 35 | 35 |
| Thiol compound derivative B | 1 | 1 | 1 | 1 | 1 | 1 | 1 | 1 | |
| Sodium stearate | 3 | | | 3 | 3 | | 3 | 3 | |
| Potassium stearate | | 3 | | | | | | | |
| Calcium stearate | | | 3 | | | | | | |
| Barium stearate | | | | | | 3 | | | |
| Magnesium stearate | | | | | | 3 | | | |
| Zinc stearate | | | | | | | | 3 | |
| Aluminum stearate | | | | | | | | 3 | |
| 2,4,6-Trimercapto-S-triazine | | | | | | | | | 0.5 |
| Zinc dibutyldithiocarbamate | | | | | | | | | 2 |

Notes:
In the table, a unit for each numerical value is part by weight.
Acrylic rubber*1: acrylic rubber of ethyl acrylate/butyl acrylate/methoxyethyl acrylate/vinyl chloroacetate (40/40/20/2)

TABLE 11

(Composition)

| | Ex. 16 | Ex. 17 | Ex. 18 | Ex. 19 | Ex. 20 | Ex. 21 | Ex. 22 | Ex. 23 | Ex. 24 | Ex. 25 |
|---|---|---|---|---|---|---|---|---|---|---|
| Acrylic rubber*1 | 100 | 100 | 100 | 100 | 100 | 100 | 100 | 100 | 100 | 100 |
| Stearic acid | 1 | 1 | 1 | 1 | 1 | 1 | 1 | 1 | 1 | 1 |
| 4,4'-Bis(α,α-dimethylbenzyl)diphenylamine | 2 | 2 | 2 | 2 | | 2 | 2 | 2 | 2 | 2 |
| MAF (N550) carbon | 50 | 50 | 50 | 50 | 50 | 50 | 50 | 50 | 50 | 50 |
| SRF (N774) carbon | 35 | 35 | 35 | 35 | 35 | 35 | 35 | 35 | 35 | 35 |
| Thiol compound derivative B | 1 | 1 | 1 | 1 | 1 | 1 | 1 | 1 | 1 | 1 |
| Sodium stearate | 3 | 3 | 3 | 3 | 3 | 3 | 3 | 3 | 3 | 3 |
| Cetylmethylammonium bromide | 0.005 | 0.05 | 0.5 | | | | | | | |
| Magnesium oxide | | | | | 2 | | | | | |
| Calcium hydroxide | | | | | | 2 | | | | |
| Calcium carbonate | | | | | | | 2 | | | |
| Zinc oxide | | | | | | | | 2 | | |
| Lead oxide | | | | | | | | | 2 | |
| Hydrotalcite DHT-4A | | | | | | | | | | 2 |

Notes:
In the table, a unit for each numerical value is part by weight.
Acrylic rubber*1: acrylic rubber of ethyl acrylate/butyl acrylate/methoxyethyl acrylate/vinyl chloroacetate (40/40/20/2)

TABLE 12

| (Composition) | | | | | | | | |
|---|---|---|---|---|---|---|---|---|
| | Ex. 26 | Ex. 27, | Ex. 28 | Ex. 29 | Ex. 30 | Ex. 31 | Ex. 32 | Ex. 33 |
| Acrylic rubber*[1] | 100 | 100 | 100 | 100 | 100 | 100 | 100 | 100 |
| Stearic acid | 1 | 1 | 1 | 1 | 1 | 1 | 1 | 1 |
| 4,4'-Bis(α,α-dimethylbenzyl)diphenylamine | 2 | 2 | 2 | | 2 | 2 | 2 | 2 |
| MAF (N550) carbon | 50 | 50 | 50 | 50 | 50 | 50 | 50 | 50 |
| SRF (N774) carbon | 35 | 35 | 35 | 35 | 35 | 35 | 35 | 35 |
| Thiol compound derivative B | 1 | 1 | 1 | 1 | 1 | 1 | 1 | 1 |
| Sodium stearate | 3 | 3 | 3 | 3 | 3 | 3 | 3 | 3 |
| NOCRAC CD*[2] | 2 | 2 | 2 | | | | | |
| NOCRAC 400*[3] | | | | 2 | | | | |
| NOCRAC TNP*[4] | | | | | 2 | | | |
| NOCRAC MB*[5] | | | | | | 2 | | |
| NOCRAC NEC*[6] | | | | | | | 2 | |
| NOCRAC NS-10-N*[7] | | | | | | | | 2 |

Notes:
In the table, a unit for each numerical value is part by weight.
*[1]Acrylic rubber: acrylic rubber of ethyl acrylate/butyl acrylate/methoxyethyl acrylate/vinyl chloroacetate (40/40/20/2)
*NOCRAC: available from Ouchi Shinko Kagaku Kogyo K.K., anti-aging agent
*[2]NOCRAC CD: amine type anti-aging agent (4,4'-bis(α,α-dimethylbenzyl)diphenylamine)
*[3]NOCRAC 400: thioether type anti-aging agent (dilauryl thiopropionate)
*[4]NOCRAC TNP: phosphorus type anti-aging agent (tri(nonylphenyl) phosphite)
*[5]NOCRAC MB: imidazole type anti-aging agent (2-mercaptobenzoimidazole)
*[6]NOCRAC NEC: carbamate type anti-aging agent (nickel diethyldithiocarbamate)
*[7]NOCRAC NS-10-N: thiourea type anti-aging agent (1,3-bis(dimethylaminopropyl)-2-thiourea)

TABLE 13

| (Properties) | | | | | | | | | |
|---|---|---|---|---|---|---|---|---|---|
| | Ex. 8 | Ex. 9 | Ex. 10 | Ex. 11 | Ex. 12 | Ex. 13 | Ex. 14 | Ex. 15, | Comp. Ex. 6 |
| Properties in unvulcanized state (stability) | | | | | | | | | |
| Mooney scorch 125° C. (initial value) | | | | | | | | | |
| ML1 + 4 | 51 | 60 | 51 | 52 | 51 | 48 | 50 | 48 | 62 |
| t5 (min) | 5.9 | 5.9 | 10.1 | 10.6 | 15.3 | >30 | >30 | >30 | 5.2 |
| Mooney scorch 125° C. (after storage of 40° C., 40% RH and 7 days) | | | | | | | | | |
| ML1 + 4 | 48 | 71 | 49 | 47 | 45 | | | | immeasurable |
| t5 (min) | 5.5 | 4.9 | 7.7 | 7.6 | 10.7 | | | | immeasurable |
| Properties after primary vulcanization (primary vulcanization conditions: 180° C./8 min) | | | | | | | | | |
| Hardness (Pts) (JIS K 6253) | 66 | 64 | 60 | 68 | | — | — | — | |
| Tensile strength (MPa) (JIS K 6251) | 8.0 | 8.7 | 6.9 | 7.5 | | — | — | — | |
| Elongation at break (%) (JIS K 6251) | 250 | 240 | 540 | 300 | | — | — | — | |
| Compression set (JIS K 6262) 25% compression, 150° C./70 hrs | 22 | 17 | 73 | 30 | | — | — | — | |
| Properties after secondary vulcanization (primary vulcanization conditions: 180° C./8 min, secondary vulcanization conditions: 170° C./4 hrs) | | | | | | | | | |
| Hardness (Pts) (JIS K 6253) | 69 | 66 | 68 | 70 | 69 | — | — | — | 64 |
| Tensile strength (MPa) (JIS K 6251) | 9.4 | 10.0 | 9.5 | 9.1 | 7.6 | — | — | — | 10.1 |
| Elongation at break (%) (JIS K 6251) | 210 | 190 | 310 | 230 | 370 | — | — | — | 220 |
| Compression set (JIS K 6262) 25% compression, 150° C./70 hrs | 12 | 10 | 31 | 15 | 42 | — | — | — | 11 |

Notes:
In Examples 13, 14 and 15, vulcanization reaction did not proceed under the above conditions, and vulcanization molding of the composition was impossible.

TABLE 14

| (Properties) | | | | | | | | | | |
|---|---|---|---|---|---|---|---|---|---|---|
| | Ex. 16 | Ex. 17 | Ex. 18 | Ex. 19 | Ex. 20 | Ex. 21 | Ex. 22 | Ex. 23 | Ex. 24 | Ex. 25 |
| Properties in unvulcanized state (stability) | | | | | | | | | | |
| Mooney scorch 125° C. (initial value) | | | | | | | | | | |
| ML1 + 4 | 48 | 54 | | 51 | 62 | 61 | 49 | 55 | 56 | 47 |
| t5 (min) | 5.7 | 4.7 | | 5.9 | 4.8 | 5.6 | 7.8 | 6.3 | 7.4 | 9.0 |
| Mooney scorch 125° C. (after storage of 40° C., 40% RH and 7 days) | | | | | | | | | | |
| ML1 + 4 | 44 | 55 | | 48 | 74 | 86 | 47 | 74 | 72 | 41 |
| t5 (min) | 5.1 | 4.0 | | 5.5 | 5.2 | 4.1 | 6.8 | 5.6 | 4.9 | 8.9 |
| Properties after primary vulcanization (primary vulcanization conditions: 180° C./8 min) | | | | | | | | | | |
| Hardness (Pts) (JIS K 6253) | 65 | 65 | 66 | 66 | 71 | 71 | 67 | 69 | 56 | 70 |
| Tensile strength (MPa) (JIS K 6251) | 7.8 | 8.1 | 9.3 | 8.0 | 8.1 | 8.0 | 7.8 | 7.5 | 5.9 | 8.2 |
| Elongation at break (%) (JIS K 6251) | 250 | 230 | 150 | 250 | 260 | 230 | 250 | 290 | 580 | 240 |
| Compression set (JIS K 6262) 25% compression, 150° C./70 hrs | 22 | 21 | 14 | 22 | 51 | 39 | 24 | 38 | 82 | 38 |
| Properties after secondary vulcanization (primary vulcanization conditions: 180° C./8 min, secondary vulcanization conditions: 170° C./4 hrs) | | | | | | | | | | |
| Hardness (Pts) (JIS K 6253) | 68 | 68 | 68 | 69 | 75 | 73 | 69 | 72 | 60 | 70 |
| Tensile strength (MPa) (JIS K 6251) | 9.5 | 10.0 | 10.1 | 9.4 | 9.6 | 9.6 | 9.1 | 8.5 | 7.9 | 9.5 |
| Elongation at break (%) (JIS K 6251) | 190 | 180 | 160 | 210 | 200 | 200 | 200 | 230 | 370 | 220 |
| Compression set (JIS K 6262) 25% compression, 150° C./70 hrs | 12 | 13 | 10 | 12 | 36 | 25 | 14 | 31 | 40 | 25 |

TABLE 15

| (Properties) | | | | | | | | |
|---|---|---|---|---|---|---|---|---|
| | Ex. 26 | Ex. 27 | Ex. 28 | Ex. 29 | Ex. 30 | Ex. 31 | Ex. 32 | Ex. 33 |
| Properties in unvulcanized state (stability) | | | | | | | | |
| Mooney scorch 125° C. (initial value) | | | | | | | | |
| ML1 + 4 | 41 | 40 | 39 | 42 | 42 | 45 | 44 | 53 |
| t5 (min) | 9.7 | 6.5 | 10.2 | 10.7 | 5.2 | 3.6 | 10.2 | 2.3 |
| Mooney scorch 125° C. (after storage of 40° C., 40% RH and 7 days) | | | | | | | | |
| ML1 + 4 | 43 | 41 | 40 | 42 | 44 | 46 | 43 | 55 |
| t5 (min) | 9.2 | 6.4 | 10.0 | 9.9 | 4.8 | 3.7 | 9.8 | 2.1 |
| Properties after primary vulcanization (primary vulcanization conditions: 180° C./8 min) | | | | | | | | |
| Hardness (Pts) (JIS K 6253) | 64 | 63 | 64 | 64 | 63 | 59 | 68 | 67 |
| Tensile strength (MPa) (JIS K 6251) | 8.6 | 8.3 | 8.5 | 8.4 | 8.5 | 9.0 | 8.6 | 9.6 |
| Elongation at break (%) (JIS K 6251) | 200 | 240 | 220 | 220 | 240 | 310 | 210 | 210 |

TABLE 15-continued

| (Properties) | | | | | | | | |
|---|---|---|---|---|---|---|---|---|
|  | Ex. 26 | Ex. 27 | Ex. 28 | Ex. 29 | Ex. 30 | Ex. 31 | Ex. 32 | Ex. 33 |
| Compression set (JIS K 6262) 25% compression, 150° C./70 hrs | 19 | 20 | 28 | 30 | 29 | 61 | 32 | 30 |
| Properties after secondary vulcanization (primary vulcanization conditions: 180° C./8 min, secondary vulcanization conditions: 170° C./4 hrs) | | | | | | | | |
| Hardness (Pts) (JIS K 6253) | 70 | 69 | 69 | 70 | 69 | 67 | 71 | 74 |
| Tensile strength (MPa) (JIS K 6251) | 10.3 | 10.1 | 10.2 | 10.6 | 10.9 | 10.7 | 10.1 | 12.2 |
| Elongation at break (%) (JIS K 6251) | 180 | 190 | 180 | 180 | 190 | 230 | 180 | 140 |
| Compression set (JIS K 6262) 25% compression, 150° C./70 hrs | 12 | 13 | 13 | 14 | 15 | 18 | 19 | 25 |

As can be seen from Table 10 and Table 13, of the compositions containing the acrylic rubber (halogen-containing crosslinking polymer) and the specific thiol compound derivative, the compositions containing an organic acid alkali metal salt or an organic acid alkaline earth metal salt as the vulcanization accelerator readily underwent vulcanization reaction even in the case where the vulcanization molding was carried out under the same conditions, and the vulcanization molded products had excellent properties.

As can be seen from Table 11 and Table 14, when an organic acid metal salt was contained as the vulcanization accelerator and an onium compound was contained as the vulcanization supplement accelerator, even the primary vulcanization products showed excellent compression set also in the case where the vulcanization molding was carried out under the same conditions.

As can be seen from Table 12 and Table 15, when an amine type compound, a sulfur compound of thioether type or a phosphorus compound of phosphite type was used as the anti-aging agent, aging could be prevented. Moreover, the vulcanization products had excellent physical properties, and in particular, even the primary vulcanization products showed excellent compression set.

Example 34

In a four-necked flask equipped with a thermometer, a reflux condenser and a stirrer, 19.5 g (0.11 mol) of 1,3,5-triazine-2,4,6-trithiol, 200 g of acetone, 88.8 g (0.3 mol) of octadecyl vinyl ether and 0.3 g of acidic butyl phosphate ester (AP-4, available from Daihachi Kagaku Kogyo K. K.) were placed, and they were reacted at 65° C. for 16 hours. To the reaction solution, 200 g of toluene was added, and the insolubles were filtered. Then, the filtrate was concentrated to obtain 99.23 g of a light yellow waxy substance.

The waxy substance thus obtained was applied to a KRS-5 cell to measure an IR absorption spectrum. A chart of the measurement result is shown in FIG. 7.

As can be seen from FIG. 7, absorption at about 1620 cm$^{-1}$, that is absorption by the double bond of octadecyl vinyl ether, disappears. As can be seen from FIG. 7, further, absorption at about 1590 cm$^{-1}$, that is absorption by the SH bond (enol structure) or the C=S bond (keto structure) of the 1,3,5-triazine-2,4,6-trithiol and appears in FIG. 2, also disappears. From the results, it has been confirmed that the waxy substance, which was the resulting product, was an adduct of 1,3,5-triazine-2,4,6-trithiol with octadecyl vinyl ether, namely, a thiol compound derivative wherein the thiol group was added to the vinyl group. The yield of the product was 93% based on the octadecyl vinyl ether.

Example 35

In a four-necked flask equipped with a thermometer, a reflux condenser and a stirrer, 45 g (0.17 mol) of 6-dibutylamino-S-triazine-2,4-dithiol, 200 g of acetone, 36.6 g (0.367 mol) of n-butyl vinyl ether and 0.3 g of acid butyl phosphate (AP-4, available from Daihachi Kagaku Kogyo K. K.) were placed, and they were reacted at 60° C. for 12 hours. The reaction solution was concentrated to obtain 74.05 g of a white paste.

The paste thus obtained was applied to a KRS-5 cell to measure an IR absorption spectrum. A chart of the measurement result is shown in FIG. 8. An IR absorption spectrum of 6-dibutylamino-S-triazine-2,4-dithiol which was a starting material was also measured by the KBr tablet method. A chart of the measurement result is shown in FIG. 9.

As can be seen from FIG. 8, absorption at about 1619 cm$^{-1}$, that is absorption by the double bond of n-butyl vinyl ether, disappears. As can be seen from FIG. 8, further, absorption at about 1600 cm$^{-1}$, that is absorption by the SH bond (enol structure) or the C=S bond (keto structure) of the 6-dibutylamino-S-triazine-2,4-dithiol and appears in FIG. 9, also disappears. From the results, it has been confirmed that the paste, which was the resulting product, was an adduct of 6-dibutylamino-S-triazine-2,4-dithiol with n-butyl vinyl ether, namely, a thiol compound derivative wherein the thiol group was added to the vinyl group. The yield of the product was 95% based on the 6-dibutylamino-S-triazine-2,4-dithiol.

Example 36

A viscous yellow liquid of 79.9 g was obtained in the same manner as in Example 34, except that 61.9 g (0.72 mol) of isopropyl vinyl ether was used instead of 72.1 g (0.72 mol) of n-butyl vinyl ether.

The viscous yellow liquid thus obtained was applied to a KRS-5 cell to measure an IR absorption spectrum. A chart of the measurement result is shown in FIG. 10.

As can be seen from FIG. 10, absorption at about 1620 cm$^{-1}$, that is absorption by the double bond of isopropyl vinyl ether, disappears. As can be seen from FIG. 10, further, absorption at about 1590 cm$^{-1}$, that is absorption by the SH bond (enol structure) or the C=S bond (keto structure) of the 1,3,5-triazine-2,4,6-trithiol and appears in FIG. 2, also disappears. From the results, it has been confirmed that the viscous yellow liquid, which was the resulting product, was an adduct of 1,3,5-triazine-2,4,6-trithiol with isopropyl vinyl ether, namely, a thiol compound derivative wherein the thiol group was added to the vinyl group. The yield of the product was 92% based on the 1,3,5-triazine-2,4,6-trithiol.

Example 37

A viscous yellow liquid of 85.9 g was obtained in the same manner as in Example 34, except that 68.0 g (0.54 mol) of cyclohexyl vinyl ether was used instead of 72.1 g (0.72 mol) of n-butyl vinyl ether.

The viscous yellow liquid thus obtained was applied to a KRS-5 cell to measure an IR absorption spectrum. A chart of the measurement result is shown in FIG. 11.

As can be seen from FIG. 11, absorption at about 1620 cm$^{-1}$, that is absorption by the double bond of cyclohexyl vinyl ether, disappears. As can be seen from FIG. 11, further, absorption at about 1590 cm$^{-1}$, that is absorption by the SH bond (enol structure) or the C=S bond (keto structure) of the 1,3,5-triazine-2,4,6-trithiol and appears in FIG. 2, also disappears. From the results, it has been confirmed that the viscous yellow liquid, which was the resulting product, was an adduct of 1,3,5-triazine-2,4,6-trithiol with cyclohexyl vinyl ether, namely, a thiol compound derivative wherein the thiol group was added to the vinyl group. The yield of the product was 86% based on the cyclohexyl vinyl ether.

Example 38

A viscous yellow liquid of 40.2 g was obtained in the same manner as in Example 34, except that 68.0 g (0.59 mol) of 4-hydroxybutyl vinyl ether was used instead of 72.1 g (0.72 mol) of n-butyl vinyl ether.

The viscous yellow liquid thus obtained was applied to a KRS-5 cell to measure an IR absorption spectrum. A chart of the measurement result is shown in FIG. 12.

As can be seen from FIG. 12, absorption at about 1620 cm$^{-1}$, that is absorption by the double bond of 4-hydroxybutyl vinyl ether, disappears. As can be seen from FIG. 12, further, absorption at about 1590 cm$^{-1}$, that is absorption by the SH bond (enol structure) or the C=S bond (keto structure) of the 1,3,5-triazine-2,4,6-trithiol and appears in FIG. 2, also disappears. From the results, it has been confirmed that the viscous yellow liquid, which was the resulting product, was an adduct of 1,3,5-triazine-2,4,6-trithiol with 4-hydroxybutyl vinyl ether, namely, a thiol compound derivative wherein the thiol group was added to the vinyl group. The yield of the product was 39% based on the 4-hydroxybutyl vinyl ether.

Example 39

In a four-necked flask equipped with a thermometer, a reflux condenser and a stirrer, 35.46 g (0.2 mol) of 1,3,5-triazine-2,4,6-trithiol, 0.3 g of acid butyl phosphate (AP-4, available from Daihachi Kagaku Kogyo K. K.), 72.1 g (0.72 mol) of isobutyl vinyl ether and 190 g of acetone were placed, and they were reacted at 65° C. for 16 hours. After the reaction was completed, the insolubles were filtered, and the filtrate was concentrated to obtain 91 g of a viscous yellow liquid.

The viscous yellow liquid thus obtained was applied to a KRS-5 cell to measure an IR absorption spectrum. A chart of the measurement result is shown in FIG. 13.

As can be seen from FIG. 13, absorption at about 1621 cm$^{-1}$, that is absorption by the double bond of isobutyl vinyl ether, disappears. As can be seen from FIG. 13, further, absorption at about 1590 cm$^{-1}$, that is absorption by the SH bond (enol structure) or the C=S bond (keto structure) of the 1,3,5-triazine-2,4,6-trithiol and appears in FIG. 2, also disappears. From the results, it has been confirmed that the resulting product was an adduct of 1,3,5-triazine-2,4,6-trithiol with isobutyl vinyl ether, namely, a thiol compound derivative wherein the thiol group was added to the vinyl group. The yield of the product was 93% based on the 1,3,5-triazine-2,4,6-trithiol.

The viscous yellow liquid, which was the resulting product, was applied in a thickness of about 1 mm to a slide glass and allowed to stand for 70 days in the atmosphere at a temperature of 23±2° C. and a humidity of 50±5%. As a result, the liquid became a solid. When an IR absorption spectrum of the yellow solid was measured by the KBr tablet method using the aforesaid infrared spectrophotometer, a result shown in FIG. 14 was obtained. As can be seen from FIG. 14, there is absorption at about 1590 cm$^{-1}$ assigned to the 1,3,5-triazine-2,4,6-trithiol which was a starting material, and it was proved that the product had been decomposed.

Example 40

In a four-necked flask equipped with a thermometer, a reflux condenser and a stirrer, 35.46 g (0.2 mol) of 1,3,5-triazine-2,4,6-trithiol, 0.3 g of acid butyl phosphate (AP-4, available from Daihachi Kagaku Kogyo K. K.), 72.1 g (0.72 mol) of isobutyl vinyl ether and 190 g of acetone were placed, and they were reacted at 65° C. for 16 hours. After the reaction was completed, 4.0 g of hydrotalcite (Kyoward 500SH, available from Kyowa Kagaku Kogyo K. K.) was added, and they were stirred at 40° C. for 10 hours. Then, the mixture was filtered, and the filtrate was concentrated to obtain 80 g of a viscous yellow liquid.

The viscous yellow liquid thus obtained was applied to a KRS-5 cell to measure an IR absorption spectrum. A chart of the measurement result is shown in FIG. 15.

As can be seen from FIG. 15, absorption at about 1621 cm$^{-1}$, that is absorption by the double bond of isobutyl vinyl ether, disappears. As can be seen from FIG. 15, further, absorption at about 1590 cm$^{-1}$, that is absorption by the SH bond (enol structure) or the C=S bond (keto structure) of the 1,3,5-triazine-2,4,6-trithiol and appears in FIG. 2, also disappears. From the results, it has been confirmed that the resulting product was an adduct of 1,3,5-triazine-2,4,6-trithiol with isobutyl vinyl ether, namely, a thiol compound derivative wherein the thiol group was added to the vinyl group. The yield of the product was 84% based on the 1,3,5-triazine-2,4,6-trithiol.

The viscous yellow liquid, which was the resulting product, was applied in a thickness of about 1 mm to a slide glass and allowed to stand for 70 days in the atmosphere at a temperature of 23±2° C. and a humidity of 50±5%. As a result, there was no change of appearance such as turbidity. When the viscous yellow liquid having been allowed to stand for 70 days was applied to a KRS-cell to measure an IR absorption spectrum, a result shown in FIG. 16 was obtained.

As can be seen from FIG. 16, there is no absorption at about 1590 cm$^{-1}$ assigned to the 1,3,5-triazine-2,4,6-trithiol which was a starting material, and decomposition of the product was not confirmed.

Example 41

In a four-necked flask equipped with a thermometer, a reflux condenser and a stirrer, 35.46 g (0.2 mol) of 1,3,5-triazine-2,4,6-trithiol, 0.3 g of acid butyl phosphate (AP-4, available from Daihachi Kagaku Kogyo K. K.), 72.1 g (0.72 mol) of isobutyl vinyl ether and 190 g of acetone were placed, and they were reacted at 65° C. for 16 hours. After the reaction was completed, 1.0 g of tetra(2-ethylhexyl) titanate (Orgatics TA-30, available from Matsumoto Seiyaku Kogyo K. K.) was added, and the mixture was concentrated to obtain 90 g of a viscous brown liquid.

The viscous brown liquid thus obtained was applied to a KRS-5 cell to measure an IR absorption spectrum. A chart of the measurement result is shown in FIG. 17.

As can be seen from FIG. 17, absorption at about 1621 cm$^{-1}$, that is absorption by the double bond of isobutyl vinyl ether, disappears. As can be seen from FIG. 17, further, absorption at about 1590 cm$^{-1}$, that is absorption by the SH bond (enol structure) or the C=S bond (keto structure) of the 1,3,5-triazine-2,4,6-trithiol and appears in FIG. 2, also disappears. From the results, it has been confirmed that the resulting product was an adduct of 1,3,5-triazine-2,4,6-trithiol with isobutyl vinyl ether, namely, a thiol compound derivative wherein the thiol group was added to the vinyl group. The yield of the product was 93% based on the 1,3,5-triazine-2, 4,6-trithiol.

The viscous brown liquid, which was the resulting product, was applied in a thickness of about 1 mm to a slide glass and allowed to stand for 70 days in the atmosphere at a temperature of 23±2° C. and a humidity of 50±5%. As a result, the viscous brown liquid had no change of appearance such as turbidity. When the viscous brown liquid having been allowed to stand for 70 days was applied to a KRS-cell to measure an IR absorption spectrum, a result shown in FIG. 18 was obtained. As can be seen from FIG. 18, there is no absorption at about 1590 cm$^{-1}$ assigned to the 1,3,5-triazine-2,4,6-trithiol which was a starting material, and decomposition of the product was not confirmed.

What is claimed is:

1. A thiol compound derivative selected from the group consisting of compounds represented by formula (1), formula (8), formula (9), formula (10), formula (15) and formula (16):

(1)

(8)

(9)

(10)

(15)

(16)

wherein $X^1$, $X^2$ and $X^3$ may be the same or different and are each a group represented by the following formula (2), M is an alkali metal or an alkaline earth metal, and $R^5$ is a group selected from the following groups (g) to (k), (2)

wherein A is an oxygen atom or a sulfur atom, $R^1$ is a hydrogen atom, an alkyl group or a phenyl group, $R^2$ is a group selected from the group consisting of the following groups (a) to (f), when R1 and R2 are each an alkyl group, R1 and R2 may form a ring, $R^3$ is a hydrogen atom, an alkyl group or a phenyl group;

(a) a group selected from an alkyl group, a halogenated alkyl group, an alkyl group having at least one hydroxyl group, an alkenyl group, an alkynyl group and an aralkyl group, (b) a residue wherein a hydroxyl group is removed from a hydroxyl group-containing compound selected from alkylene glycol, dialkylene glycol, trialkylene glycol, tetraalkylene glycol, allyl alcohols, ketooximes, alkanolamines, dialkanolamines, trialkanolamines, trialkylsilanol, alicyclic alcohol and naphthyl alcohols, (c) a group represented by the following formula (3):

—CHY—CH$_2$X (3)

wherein X is any one of a halogen atom, an alkoxy group, an alkoxyalkoxy group, a dialkylamino group, a trialkylsilyl group, an acetoxy group and a piperidino group, and Y is a hydrogen atom or a halogen atom, (d) a group represented by the following formula (4):

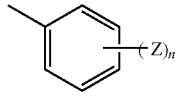  (4)

wherein Z is any one of a hydrogen atom, a halogen atom, a nitro group, an amino group, an alkoxy group, an alkylamino group, a dialkylamino group, an alkyl group and an acyl group, and n is an integer of 1 to 3 and is a number of substituents Z bonded to the phenyl group skeleton in the formula (4), (e) a group represented by $-CH_2-C_6H_5$ or $-CHCH_3-C_6H_5$, and (f) a group represented by the following formula (5) or (6):

  (5)

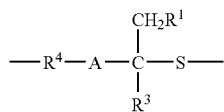  (6)

wherein $R^1$ and $R^3$ are the same as $R^1$ and $R^3$ in the formula (2), A is an oxygen atom or a sulfur atom, and $R^4$ is any one of $-CH_2-$, $-CH_2CH_2-$, $-CH_2CH_2CH_2-$, $-CH_2CH_2CH_2CH_2-$, $-CH_2CH_2OCH_2CH_2-$, $-CH_2CH_2OCH_2CH_2OCH_2CH_2-$,

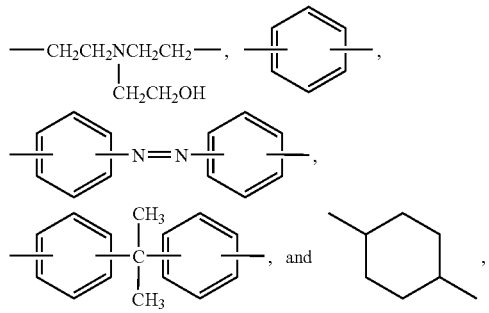

(g) a group selected from a hydrogen atom, an alkyl group, an alkenyl group, an alkynyl group, a phenyl group, an aralkyl group and $-NH_2$, (h) a dialkylamino group represented by the following formula (11):

  (11)

wherein $R^6$ and $R^7$ are each a group selected from an alkyl group, an alkenyl group, an alkynyl group, an aralkyl group, a benzyl group, an allyl group, a cycloalkyl group, a fluoroalkyl group and a phenyl group, and $R^6$ and $R^7$ may be the same or different, (i) a monoalkylamino group represented by the following formula (12):

  (12)

wherein $R^8$ is a group selected from an alkyl group, an alkenyl group, an alkynyl group, an aralkyl group, a benzyl group, an allyl group, a cycloalkyl group, a fluoroalkyl group, an anilino group, a hydroxyanilino group and a phenyl group, (j) a group represented by the following formula (13):

  (13)

wherein $R^9$ is a group selected from an alkyl group, an alkenyl group, an aralkyl group, a halogenophenyl group, a naphthyl group, a cycloalkyl group and a phenyl group, and (k) a group represented by the following formula (14):

  (14)

wherein $R^{10}$ is a group selected from an alkyl group, an alkenyl group, an alkynyl group, a phenyl group, an aralkyl group, a halogenophenyl group, a naphthyl group and a cycloalkyl group.

2. The thiol compound derivative as represented by formula (1) of claim 1, wherein in the formula (2), A is an oxygen atom, $R^1$ is a hydrogen atom, $R^2$ is an alkyl group or a residue wherein a hydroxyl group is removed from (poly)alkylene glycol, and $R^3$ is a hydrogen atom.

3. The thiol compound derivative as represented by formula (1) of claim 1, wherein the formula (2) is represented by the following formula (7):

  (7)

wherein n is 3 or 4.

4. The thiol compound derivative as represented by formula (10) of claim 1, wherein in the formula (2), A is an oxygen atom, $R^1$ is a hydrogen atom, $R^2$ is an alkyl group or a residue wherein a hydroxyl group is removed from (poly)alkylene glycol, and $R^3$ is a hydrogen atom.

5. The thiol compound derivative as represented by formula (10) of claim 1, wherein the formula (2) is represented by the following formula (7):

  (7)

wherein n is 3 or 4.

* * * * *